(12) United States Patent
Park et al.

(10) Patent No.: US 11,236,061 B2
(45) Date of Patent: Feb. 1, 2022

(54) XANTHENE-BASED COMPOUND AND PHOTOSENSITIVE RESIN COMPOSITION COMPRISING SAME

(71) Applicant: LG CHEM, LTD., Seoul (KR)

(72) Inventors: Jongho Park, Daejeon (KR); Dami Lee, Daejeon (KR); Seung Jin Yang, Daejeon (KR); Jihye Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/801,724

(22) Filed: Feb. 26, 2020

(65) Prior Publication Data

US 2020/0262807 A1 Aug. 20, 2020

Related U.S. Application Data

(63) Continuation-in-part of application No. PCT/KR2018/006632, filed on Jun. 12, 2018.

(30) Foreign Application Priority Data

Dec. 26, 2017 (KR) .................. 10-2017-0179533

(51) Int. Cl.
*C07D 311/82* (2006.01)
*G02F 1/1335* (2006.01)

(52) U.S. Cl.
CPC ...... *C07D 311/82* (2013.01); *G02F 1/133514* (2013.01)

(58) Field of Classification Search
CPC .................................................. C07D 311/82
See application file for complete search history.

(56) References Cited

U.S. PATENT DOCUMENTS

| 6,248,904 | B1 * | 6/2001 | Zhang | C07K 7/06 435/15 |
| 10,227,491 | B2 | 3/2019 | Grund et al. | |
| 10,294,240 | B2 * | 5/2019 | Urano | C07D 493/10 |

FOREIGN PATENT DOCUMENTS

| CN | 107488159 A | 12/2017 | |
| JP | H09-241553 A | 9/1997 | |
| JP | 2017-125122 A | 7/2017 | |
| KR | 10-2001-0009058 A | 2/2001 | |
| KR | 10-2014-0122183 A | 10/2014 | |
| KR | 10-2017-0034767 A | 3/2017 | |
| TW | 201443164 A | 11/2014 | |
| TW | 201539133 A | 10/2015 | |
| WO | 2015-158574 A1 | 10/2015 | |
| WO | WO-2016137004 A1 * | 9/2016 | ............... C12Q 1/37 |

OTHER PUBLICATIONS

Hirayama "Synthesis of a new bifunctionalised fluorescent label and physical properties of the bound form on model peptide of troponin C." Organic & Biomolecular Chemistry, 2007, 5(13), 2040-2045.*
International Search Report issued for International Application No. PCT/KR2018/006632 dated Mar. 4, 2019, 2 pages.

* cited by examiner

*Primary Examiner* — David K O'Dell
(74) *Attorney, Agent, or Firm* — Rothwell, Figg, Ernst & Manbeck, P.C.

(57) ABSTRACT

The present specification provides a compound represented by Chemical Formula 1, a colorant composition, a resin composition, a photosensitive material, a color filter and a display device comprising the same.

15 Claims, 1 Drawing Sheet

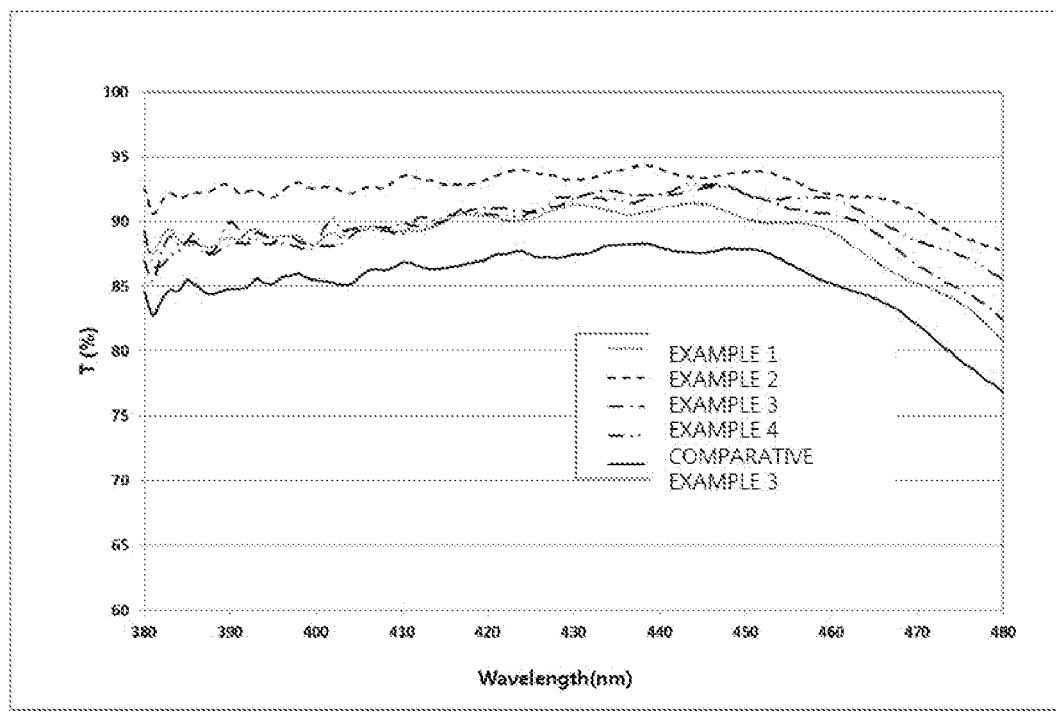

XANTHENE-BASED COMPOUND AND PHOTOSENSITIVE RESIN COMPOSITION COMPRISING SAME

CROSS-REFERENCE TO RELATED APPLICATIONS

This application is a Continuation-in-part of International Application No. PCT/KR2018/006632, filed on Jun. 12, 2018, designating the United States and which claims priority to and the benefits of Korean Patent Application No. 10-2017-0179533, filed with the Korean Intellectual Property Office on Dec. 26, 2017, the entire contents of which are incorporated herein by reference.

The present specification relates to a xanthene-based compound and a photosensitive resin composition comprising the same. In addition, the present specification relates to a color filter manufactured using the photosensitive resin composition, and a display device comprising the same.

BACKGROUND OF THE INVENTION

Recently, performance of high luminance and high contrast ratio has been required in color filters. In addition, one of main purposes of displaying a display element is differentiating display element performance through enhancing color purity and enhancing productivity in manufacturing processes.

Existing pigment types used as colorants of color filters are present in a particle dispersion state in a color photoresist, and therefore, have had difficulties in controlling luminance and contrast ratio depending on pigment particle sizes and distribution control. Pigment particles aggregate in a color filter reducing solubility and dispersibility, and multiple scattering of light occurs due to aggregated large particles. Such scattering of polarized light has been blamed as a main factor of a contrast ratio decrease. Efforts to enhance luminance and contrast ratio through ultra-atomization and dispersion stabilization of pigments have continued, however, a degree of freedom is limited in selecting a colorant for obtaining color coordinates for high color purity display devices. In addition, a pigment dispersion method using already-developed color materials, particularly pigments, has reached limit in enhancing color purity, luminance and contrast ratio of color filters using the same.

Accordingly, development of new colorants capable of enhancing color reproduction, luminance and contrast ratio by increasing color purity has been required.

BRIEF SUMMARY OF THE INVENTION

The present disclosure is directed to providing a novel-structured xanthene-based compound, a photosensitive resin composition comprising the same, a color filter manufactured using the same, and a display device comprising the same.

One embodiment of the present specification provides a compound represented by the following Chemical Formula 1.

[Chemical Formula 1]

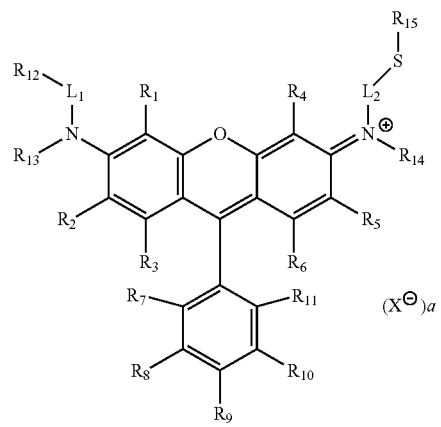

In Chemical Formula 1, $R_1$ to $R_6$ are each independently selected from the group consisting of hydrogen; deuterium; a halogen group; a nitro group; a substituted or unsubstituted linear or branched alkyl group having 1 to 30 carbon atoms; a substituted or unsubstituted alkoxy group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms, $R_7$ to $R_{11}$ are the same as or different from each other, and each independently selected from the group consisting of hydrogen; deuterium; —OH; —$SO_3^-$; —$SO_3H$; —$SO_3^-Z^+$; —$COO^-$; —COOH; —$COO^-Z^+$; —COORa; —$SO_3Rb$; —$SO_2NRcRd$; —CONRd; —$SO_2NHRe$; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms, $Z^+$ represents $^+N(Rf)_4$, $Na^+$ or $K^+$, Ra to Rf are each independently selected from the group consisting of a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms, Rc and Rd may bond to each other to form a monocyclic or polycyclic heteroring having 3 to 10 carbon atoms including a nitrogen atom, Rfs may be the same as or different from each other, at least one of $R_7$ to $R_{11}$ is —$SO_3^-$; —$SO_3H$; —$SO_3^-Z^+$; —$SO_3Rb$; —$SO_2NRcRd$; or —$SO_2NHRe$, $R_{12}$ to $R_{14}$ are the same as or different from each other, and each independently selected from the group consisting of hydrogen; deuterium; a substituted or unsubstituted linear or branched alkyl group having 1 to 30 carbon atoms; a substituted or unsubstituted monocyclic or polycyclic aryl group having 6 to 30 carbon atoms; a substituted or unsubstituted monocyclic or polycyclic heteroaryl group having 2 to 30 carbon atoms; and a substituted or unsubstituted sulfide group, $R_{13}$ and $L_1$ may bond to each other to form a monocyclic or polycyclic ring including a nitrogen atom, a is an integer of 0 or 1, X is an anionic group, $R_{15}$ is selected from the group consisting of hydrogen; deuterium; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms, $L_1$ and $L_2$ are selected from the group consisting of a direct bond; a substituted or unsubstituted linear or branched alkylene group having 1 to 30 carbon atoms; —NH—; —O—; —COO—; —OCO—; —NHCO—; —CONH—; —NR—; —NRCO—; -$L_3$-NH-$L_4$-; -$L_3$-O-$L_4$-; -$L_3$-COO-$L_4$-; -$L_3$-OCO-$L_4$-; -$L_3$-NHCO-$L_4$-; -$L_3$-CONH-$L_4$-; -$L_3$-NR-$L_4$-; and -$L_3$-NRCO-$L_4$-, $L_3$ and $L_4$ are a substituted or unsubstituted linear or branched alkylene group having 1 to 30 carbon atoms, R is selected from the group consisting of a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

One embodiment of the present specification provides a colorant composition comprising the compound of Chemical Formula 1.

One embodiment of the present specification provides a resin composition comprising the compound represented by Chemical Formula 1; a binder resin; a multifunctional monomer; a photoinitiator; and a solvent.

One embodiment of the present specification provides a photosensitive material prepared using the resin composition.

One embodiment of the present specification provides a color filter comprising the photosensitive material.

One embodiment of the present specification provides a display device comprising the color filter.

ADVANTAGEOUS EFFECTS

A xanthene-based compound according to one embodiment of the present specification can be used as a colorant in a photosensitive resin composition, and, compared to existing colorants, is capable of increasing color purity through a balance between a spectrum coming out of a light source and an absorption and transmission spectrum of a color filter.

In addition, a xanthene-based compound according to one embodiment of the present specification can be used as a color material to enhance color reproduction, luminance and contrast ratio.

DESCRIPTION OF DRAWINGS

FIG. 1 is a diagram presenting transmittance of resin compositions prepared in Examples 1 to 4 and Comparative Example 3 of the present specification.

DETAILED DESCRIPTION OF THE INVENTION

Hereinafter, the present specification will be described in more detail.

In the present specification, a description of a certain part "comprising" certain constituents means capable of further comprising other constituents, and does not exclude other constituents unless particularly stated on the contrary.

One embodiment of the present specification provides a compound represented by Chemical Formula 1.

When $L_1$ or $L_2$ linked to the nitrogen of Chemical Formula 1 is an alkylene group and sulfur (S) substitutes the alkylene group, the intermolecular interaction (n-n interaction) is relatively small, and more superior performance may be exhibited by enhancing heat resistance and reducing absorption in a short wavelength region. In addition, compared to compounds including triarylmethane (triphenylmethane), the compound represented by Chemical Formula 1 has an increased intermolecular interaction due to an increase in aromaticity caused by oxygen (O), and the xanthene-based compound represented by Chemical Formula 1 may exhibit more superior heat resistance.

Meanwhile, when $R_{13}$ or $R_{14}$ linked to the nitrogen of Chemical Formula 1 is an aryl group and sulfur directly substitutes the aryl group, heat resistance may decrease as the intermolecular interaction (π-π interaction) decreases by a steric hindrance effect. Besides, the sulfur directly substituting the aryl group may affect overlap movements of a chromophore and n electrons. In other words, the steric hindrance effect may produce absorption in a short wavelength region by affecting a conjugation angle with a chromophore and a spectrum caused by a n electron overlap. Due to the effect on the spectrum, an absorption spectrum of approximately 380 nm to 480 nm may be produced in a short wavelength, and this may induce a decrease in the luminance of a blue color filter.

Examples of the substituents of the compound represented by Chemical Formula 1 are described below, however, the substituents are not limited thereto.

The term "substituted or unsubstituted" in the present specification means being substituted with one or more substituents selected from the group consisting of deuterium; a halogen group; an alkyl group; an alkenyl group; an alkoxy group; a cycloalkyl group; a silyl group; an arylalkenyl group; an aryl group; an aryloxy group; an aralkyl group; an aralkenyl group; an alkylthioxy group; an alkylsulfoxy group; an arylsulfoxy group; a boron group; an alkylamine group; an aralkylamine group; an arylamine group; a heteroaryl group; a carbazole group; an acryloyl group; an acrylate group; an ether group; a nitrile group; a nitro group; a hydroxyl group; a cyano group; a heterocyclic group including one or more of N, O, S or P atom; and an anionic group, or having no substituents.

In the present specification, the alkyl group may be linear or branched, and although not particularly limited thereto, the number of carbon atoms is preferably from 1 to 30. In one embodiment, the number of carbon atoms may be from 1 to 20. In another embodiment, the number of carbon atoms may be from 1 to 10. Specific examples thereof may include a methyl group, an ethyl group, a propyl group, an isopropyl group, a butyl group, a t-butyl group, a pentyl group, a hexyl group, a heptyl group and the like, but are not limited thereto.

In the present specification, the alkenyl group may be linear or branched, and although not particularly limited thereto, the number of carbon atoms is preferably from 2 to 30. Specific examples thereof preferably include an alkenyl group substituted with an aryl group such as a stylbenyl group or a styrenyl group, but are not limited thereto.

In the present specification, the alkoxy group may be linear or branched, and although not particularly limited thereto, the number of carbon atoms is preferably from 1 to 30. In one embodiment, the number of carbon atoms may be from 1 to 20. In another embodiment, the number of carbon atoms of the alkoxy group may be from 1 to 10.

In the present specification, the alkenyloxy group may be linear or branched, and although not particularly limited thereto, the number of carbon atoms is preferably from 2 to 30.

In the present specification, the cycloalkyl group is not particularly limited, but preferably has 3 to 20 carbon atoms, and particularly, a cyclopentyl group or a cyclohexyl group is preferred.

In the present specification, examples of the halogen group may include fluorine, chlorine, bromine or iodine.

In the present specification, the phenoxy group is not particularly limited, but preferably has 3 to 20 carbon atoms.

In the present specification, the carboxyl group is not particularly limited, but preferably has 1 to 30 carbon atoms.

In the present specification, the carboxylic acid ester group is not particularly limited, but may have 2 to 30 carbon atoms. Specific examples thereof may include methyl carboxylic acid, ethyl carboxylic acid, isopropyl carboxylic acid, benzyl carboxylic acid and the like, but are not limited thereto.

In the present specification, the carboxylate group and the sulfonate group are each a salt with a monovalent cation, and the monovalent cation may be any one selected from the group consisting of $Na^+$, $K^+$ and a quaternary ammonium cation, but is not limited thereto. Specific examples of the quaternary ammonium cation may include a tetraalkylammonium cation such as a tetramethylammonium cation, an ethyltrimethylammonium cation or a tetrapropylammonium cation, and the like, but are not limited thereto.

In the present specification, the alkoxycarbonyl group is not particularly limited, but may have 1 to 30 carbon atoms. Specific examples of the alkyl group in the alkoxycarbonyl group may include the same examples as in the descriptions of the alkyl group. Specific examples thereof may include an alkoxycarbonyl group having the alkyl group described in the specific examples of the alkyl group, but are not limited thereto.

In the present specification, the sulfonic acid group is not particularly limited, but may have 1 to 30 carbon atoms.

In the present specification, specific examples of the sulfonic acid ester group may include alkylsulfonyl having 1 to 4 carbon atoms such as methanesulfonyl, ethanesulfonyl or hexanesulfonyl, but are not limited thereto.

In the present specification, in the aralkyl group, the number of carbon atoms of the aryl part is from 6 to 30, and the number of carbon atoms of the alkyl part is from 1 to 30 in the aralkyl group. Specific examples thereof may include a benzyl group, a p-methylbenzyl group, an m-methylbenzyl group, a p-ethylbenzyl group, an m-ethylbenzyl group, a 3,5-dimethylbenzyl group, an α-methylbenzyl group, an α,α-dimethylbenzyl group, an α,α-methylphenylbenzyl group, a 1-naphthylbenzyl group, a 2-naphthylbenzyl group, a p-fluorobenzyl group, a 3,5-difluorobenzyl group, an α,α-ditrifluoromethylbenzyl group, a p-methoxybenzyl group, an m-methoxybenzyl group, an α-phenoxybenzyl group, an α-benzyloxybenzyl group, a naphthylmethyl group, a naphthylethyl group, a naphthylisopropyl group, a pyrrolylmethyl group, a pyrrolylethyl group, an aminobenzyl group, a nitrobenzyl group, a cyanobenzyl group, a 1-hydroxy-2-phenylisopropyl group, a 1-chloro-2-phenylisopropyl group and the like, but are not limited thereto.

In the present specification, descriptions on aryl provided below may be applied to the aryl part of the aralkenyl group, and descriptions on the alkenyl group provided above may be applied to the alkenyl part.

In the present specification, the aryl group may be a monocyclic aryl group or a polycyclic aryl group.

When the aryl group is a monocyclic aryl group, the number of carbon atoms is not particularly limited, but is preferably from 6 to 30. In another embodiment, the number of carbon atoms may be from 6 to 20. In another embodiment, the number of carbon atoms may be from 6 to 12. Specific examples of the monocyclic aryl group may include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may include a naphthyl group, an anthryl group, a phenanthryl group, a pyrenyl group, a perylenyl group, a chrysenyl group, a fluorenyl group and the like, but are not limited thereto.

In the present specification, the fluorenyl group may have substituents, and the substituents may bond to form a Spiro structure. Examples of the fluorenyl group may include

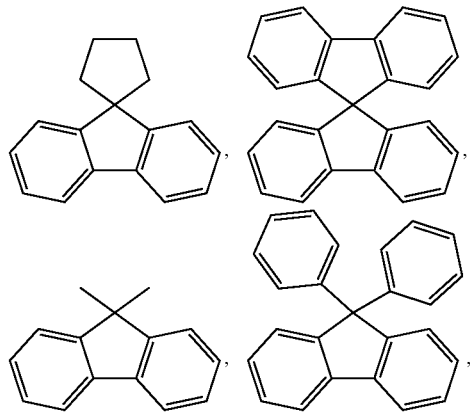

or the like.

In the present specification, the heterocyclic group is a heterocyclic group including O, N or S as a heteroatom, and although not particularly limited thereto, the number of carbon atoms is preferably from 2 to 30. In one embodiment, the number of carbon atoms may be from 2 to 20. In another embodiment, the number of carbon atoms may be from 2 to 10. Examples of the heterocyclic group may include a thiophene group, a furan group, a pyrrole group, an imidazole group, a triazole group, an oxazole group, an oxadiazole group, a triazole group, a pyridyl group, a bipyridyl group, a triazine group, an acridyl group, a pyridazine group, a quinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a dibenzofuran group and the like, but are not limited thereto.

In the present specification, the alkylene group means having two bonding sites in alkane. The alkylene group may be linear, branched or cyclic. The number of carbon atoms of the alkylene group is not particularly limited, but, for example, is from 1 to 30.

In the present specification, the alkenylene group means having two bonding sites in alkene. The alkenylene group may be linear, branched or cyclic. The number of carbon atoms of the alkenylene group is not particularly limited, but, for example, is from 2 to 30.

In the present specification, the sulfide group may be represented by —SRz, and Rz is a substituted or unsubstituted linear or branched alkyl group having 1 to 30 carbon atoms; a substituted or unsubstituted monocyclic or polycyclic aryl group having 6 to 30 carbon atoms; or a substituted or unsubstituted monocyclic or polycyclic heteroaryl group having 2 to 30 carbon atoms.

In the present specification, the anionic group is not particularly limited, and for example, anions described in U.S. Pat. No. 7,939,644, Japanese Patent Application Laid-Open Publication No. 2006-003080, Japanese Patent Application Laid-Open Publication No. 2006-001917, Japanese Patent Application Laid-Open Publication No. 2005-159926, Japanese Patent Application Laid-Open Publication No. 2007-7028897, Japanese Patent Application Laid-Open Publication No. 2005-071680, Korean Patent Application Laid-Open Publication No. 2007-7000693, Japanese Patent Application Laid-Open Publication No. 2005-111696, Japanese Patent Application Laid-Open Publication No. 2008-249663 and Japanese Patent Application Laid-Open Publication No. 2014-199436 may be used. Specific examples of the anionic group may include a trifluoromethanesulfonic acid anion, a bis(trifluoromethylsulfonyl)amide anion, a bistrifluoromethanesulfonimide anion, a bisperfluoroethylsulfonimide anion, a tetraphenylborate anion, tetrakis(4-fluorophenyl)borate, tetrakis(pentafluorophenyl)borate, tris-trifluoromethanesulfonylmethide, a halogen group such as a fluorine group, an iodine group or a chlorine group, and the like, but are not limited thereto.

In the present specification, the anionic group may have anions by itself, or may be present in a complex form with other cations. Accordingly, depending on the number of the substituted anionic groups, a sum of total charges of the compound molecule of the present disclosure may vary. Since the compound of the present disclosure has a cation in one amine group, the sum of total charges of the molecule may have a value from an anion corresponding to a value subtracting 1 from the number of substituted anionic groups to 0.

In the description of "may form a ring" in the present specification, the "ring" means a hydrocarbon ring or a heteroring, and although not particularly limited thereto, the hydrocarbon ring may have 6 to 30 carbon atoms, specifically 6 to 20 carbon atoms and more specifically 6 to 12 carbon atoms. The heteroring may have 2 to 30 carbon atoms, specifically 2 to 20 carbon atoms and more specifically 2 to 10 carbon atoms.

One embodiment of the present specification provides a compound represented by the following Chemical Formula 1.

[Chemical Formula 1]

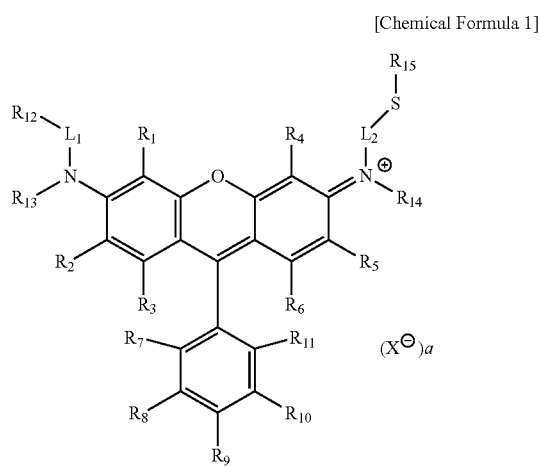

In Chemical Formula 1, $R_1$ to $R_6$ are each independently selected from the group consisting of hydrogen; deuterium; a halogen group; a nitro group; a substituted or unsubstituted linear or branched alkyl group having 1 to 30 carbon atoms; a substituted or unsubstituted alkoxy group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms, $R_7$ to $R_{11}$ are the same as or different from each other, and each independently selected from the group consisting of hydrogen; deuterium; —OH; —$SO_3^-$; —$SO_3H$; —$SO_3^-Z^+$; —$COO^-$; —COOH; —$COO^-Z^+$; —COORa; —$SO_3Rb$; —$SO_2NRcRd$; —CONRd; —$SO_2NHRe$; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms, $Z^+$ represents $^+N(Rf)_4$, $Na^+$ or $K^+$, Ra to Rf are each independently selected from the group consisting of a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms, Rc and Rd may bond to each other to form a monocyclic or polycyclic heteroring having 3 to 10 carbon atoms including a nitrogen atom, Rfs may be the same as or different from each other, at least one of $R_7$ to $R_{11}$ is —$SO_3^-$; —$SO_3H$; —$SO_3^-Z^+$; —$SO_3Rb$; —$SO_2NRcRd$; or —$SO_2NHRe$, $R_{12}$ to $R_{14}$ are the same as or different from each other, and each independently selected from the group consisting of hydrogen; deuterium; a substituted or unsubstituted linear or branched alkyl group having 1 to 30 carbon atoms; a substituted or unsubstituted monocyclic or polycyclic aryl group having 6 to 30 carbon atoms; a substituted or unsubstituted monocyclic or polycyclic heteroaryl group having 2 to 30 carbon atoms; and a substituted or unsubstituted sulfide group, $R_{13}$ and $L_1$ may bond to each other to form a monocyclic or polycyclic ring including a nitrogen atom, a is an integer of 0 or 1, X is an anionic group, $R_{15}$ is selected from the group consisting of hydrogen; deuterium; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms, $L_1$ and $L_2$ are selected from the group consisting of a direct bond; a substituted or unsubstituted linear or branched alkylene group having 1 to 30 carbon atoms; —NH—; —O—; —COO—; —OCO—; —NHCO—; —CONH—; —NR—; —NRCO—; -$L_3$-NH-$L_4$-; -$L_3$-O-$L_4$-; -$L_3$-COO-$L_4$-; -$L_3$-OCO-$L_4$-; -$L_3$-NHCO-$L_4$-; -$L_3$-CONH-$L_4$-; -$L_3$-NR-$L_4$-; and -$L_3$-NRCO-$L_4$-, $L_3$ and $L_4$ are a substituted or unsubstituted linear or branched alkylene group having 1 to 30 carbon atoms, and R is selected from the group consisting of a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

According to one embodiment of the present specification, in Chemical Formula 1, $R_1$ to $R_6$ may be each independently selected from the group consisting of hydrogen; deuterium; a halogen group; a nitro group; a substituted or unsubstituted linear or branched alkyl group having 1 to 30 carbon atoms; a substituted or unsubstituted alkoxy group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

According to another embodiment of the present specification, $R_1$ to $R_6$ may be each independently selected from the group consisting of hydrogen; deuterium; a halogen group; a nitro group; a substituted or unsubstituted linear or branched alkyl group having 1 to 20 carbon atoms; a substituted or unsubstituted alkoxy group having 1 to 20 carbon atoms; and a substituted or unsubstituted monocyclic or polycyclic aryl group having 6 to 20 carbon atoms; and a substituted or unsubstituted monocyclic or polycyclic heteroaryl group having 2 to 20 carbon atoms.

According to another embodiment of the present specification, $R_1$ to $R_6$ may be each independently selected from the group consisting of hydrogen; deuterium; a halogen group; a nitro group; a substituted or unsubstituted linear or branched alkyl group having 1 to 10 carbon atoms; a substituted or unsubstituted alkoxy group having 1 to 10 carbon atoms; and a substituted or unsubstituted monocyclic or polycyclic aryl group having 6 to 12 carbon atoms; and a substituted or unsubstituted monocyclic or polycyclic heteroaryl group having 2 to 10 carbon atoms.

According to another embodiment of the present specification, $R_1$ to $R_6$ may be each independently hydrogen.

In addition, $R_7$ to $R_{11}$ are the same as or different from each other, and each independently selected from the group consisting of hydrogen; deuterium; —OH; —$SO_3^-$; —$SO_3H$; —$SO_3^-Z^+$; —$COO^-$; —COOH; —$COO^-Z^+$; —COORa; —$SO_3Rb$; —$SO_2NRcRd$; —CONRd; —$SO_2NHRe$; a substituted or unsubstituted linear or branched alkyl group having 1 to 20 carbon atoms; a substituted or unsubstituted monocyclic or polycyclic aryl group having 6 to 20 carbon atoms; and a substituted or unsubstituted monocyclic or polycyclic heteroaryl group having 2 to 20 carbon atoms, $Z^+$ represents $^+N(Rf)_4$, $Na^+$ or $K^+$, Ra to Rf are each independently selected from the group consisting of a substituted or unsubstituted linear or branched alkyl group having 1 to 20 carbon atoms; a substituted or unsubstituted monocyclic or polycyclic aryl group having 6 to 20 carbon atoms; and a substituted or unsubstituted monocyclic or polycyclic heteroaryl group having 2 to 20 carbon atoms, Rc and Rd may bond to each other to form a monocyclic or polycyclic heteroring having 3 to 10 carbon atoms including a nitrogen atom, Rfs may be the same as or different from each other, and at least one of $R_7$ to $R_{11}$ may be —$SO_3^-$; —$SO_3H$; —$SO_3^-Z^+$; —$SO_3Rb$; —$SO_2NRcRd$; or —$SO_2NHRe$.

According to another embodiment of the present specification, $R_7$ to $R_{11}$ are the same as or different from each other, and each independently selected from the group consisting of hydrogen; deuterium; —OH; —$SO_3^-$; —$SO_3H$; —$SO_3^-Z^+$; —$COO^-$; —COOH; —$COO^-Z^+$; —COORa; —$SO_3Rb$; —$SO_2NRcRd$; —CONRd; —$SO_2NHRe$; a substituted or unsubstituted linear or branched alkyl group having 1 to 10 carbon atoms; a substituted or unsubstituted monocyclic or polycyclic aryl group having 6 to 12 carbon atoms; and a substituted or unsubstituted monocyclic or polycyclic heteroaryl group having 2 to 10 carbon atoms, $Z^+$ represents $^+N(Rf)_4$, $Na^+$ or $K^+$, Ra to Rf are each independently selected from the group consisting of a substituted or unsubstituted linear or branched alkyl group having 1 to 10 carbon atoms; a substituted or unsubstituted monocyclic or polycyclic aryl group having 6 to 12 carbon atoms; and a substituted or unsubstituted monocyclic or polycyclic heteroaryl group having 2 to 10 carbon atoms, Rc and Rd may bond to each other to form a monocyclic or polycyclic heteroring having 3 to 10 carbon atoms including a nitrogen atom, Rfs may be the same as or different from each other, and at least one of $R_7$ to $R_{11}$ may be —$SO_3^-$; —$SO_3H$; —$SO_3^-Z^+$; —$SO_3Rb$; —$SO_2NRcRd$; or —$SO_2NHRe$.

In another embodiment of the present specification, $R_7$ to $R_{11}$ are the same as or different from each other, and may be each independently hydrogen; deuterium; —$SO_3^-$; —$SO_3H$; —$SO_3^-Z^+$; —$SO_3Rb$; —$SO_2NRcRd$; or —$SO_2NHRe$, $Z^+$ represents $^+N(Rf)_4$, $Na^+$ or $K^+$, Ra to Rf are each independently selected from the group consisting of a substituted or unsubstituted linear or branched alkyl group having 1 to 10 carbon atoms; a substituted or unsubstituted monocyclic or polycyclic aryl group having 6 to 12 carbon atoms; and a substituted or unsubstituted monocyclic or polycyclic heteroaryl group having 2 to 10 carbon atoms, Rc and Rd may bond to each other to form a monocyclic or polycyclic heteroring having 3 to 10 carbon atoms including a nitrogen atom, and Rfs may be the same as or different from each other.

In another embodiment of the present specification, $R_7$ to $R_{11}$ are the same as or different from each other and may be each independently hydrogen; —$SO_3^-$; —$SO_3H$; —$SO_3^-Na^+$; —$SO_3^-K^+$; —$SO_2NRcRd$; or —$SO_2NHRe$, and Rc to Re may be linear or branched alkyl group having 1 to 30 carbon atoms.

In another embodiment of the present specification, $R_7$ to $R_{11}$ are the same as or different from each other and may be each independently hydrogen; —$SO_3^-$; —$SO_3H$; —$SO_3^-Na^+$; —$SO_3^-K^+$; —$SO_2NRcRd$; or —$SO_2NHRe$, and Rc to Re may be a linear or branched alkyl group having 1 to 20 carbon atoms.

In another embodiment of the present specification, $R_7$ to $R_{11}$ are the same as or different from each other and may be each independently hydrogen; —$SO_3^-$; —$SO_3H$; —$SO_3^-Na^+$; —$SO_3^-K^+$; —$SO_2NRcRd$; or —$SO_2NHRe$, and Rc to Re may be a linear or branched alkyl group having 1 to 10 carbon atoms.

In addition, $R_{12}$s are the same as or different from each other, and may be each independently selected from the group consisting of hydrogen; deuterium; a substituted or unsubstituted linear or branched alkyl group having 1 to 30 carbon atoms; a substituted or unsubstituted monocyclic or polycyclic aryl group having 6 to 30 carbon atoms; a substituted or unsubstituted monocyclic or polycyclic heteroaryl group having 2 to 30 carbon atoms; and a substituted or unsubstituted sulfide group.

According to another embodiment of the present specification, $R_{12}$s are the same as or different from each other, and may be each independently selected from the group consisting of hydrogen; deuterium; a substituted or unsubstituted linear or branched alkyl group having 1 to 20 carbon atoms; a substituted or unsubstituted monocyclic or polycyclic aryl group having 6 to 20 carbon atoms; a substituted or unsubstituted monocyclic or polycyclic heteroaryl group having 2 to 20 carbon atoms; and a substituted or unsubstituted sulfide group.

According to another embodiment of the present specification, $R_{12}$s are the same as or different from each other, and may be each independently selected from the group consisting of hydrogen; deuterium; a substituted or unsubstituted linear or branched alkyl group having 1 to 10 carbon atoms; a substituted or unsubstituted monocyclic or polycyclic aryl group having 6 to 12 carbon atoms; a substituted or unsubstituted monocyclic or polycyclic heteroaryl group having 2 to 10 carbon atoms; and a substituted or unsubstituted sulfide group.

According to another embodiment of the present specification, $R_{12}$ may be a substituted or unsubstituted sulfide group.

According to another embodiment of the present specification, $R_{12}$ may be a sulfide group substituted with a phenyl group.

According to another embodiment of the present specification, $R_{12}$ may be an ethyl group.

$R_{13}$ and $R_{14}$ are the same as or different from each other, and may be each independently selected from the group consisting of hydrogen; deuterium; a substituted or unsubstituted linear or branched alkyl group having 1 to 30 carbon atoms; a substituted or unsubstituted monocyclic or polycyclic aryl group having 6 to 30 carbon atoms; a substituted or unsubstituted monocyclic or polycyclic heteroaryl group having 2 to 30 carbon atoms; and a substituted or unsubstituted sulfide group.

In one embodiment of the present specification, $R_{13}$ and $R_{14}$ are the same as or different from each other, and may be each independently selected from the group consisting of hydrogen; deuterium; a substituted or unsubstituted linear or branched alkyl group having 1 to 20 carbon atoms; a substituted or unsubstituted monocyclic or polycyclic aryl group having 6 to 20 carbon atoms; a substituted or unsubstituted monocyclic or polycyclic heteroaryl group having 2 to 20 carbon atoms; and a substituted or unsubstituted sulfide group.

In one embodiment of the present specification, $R_{13}$ and $R_{14}$ are the same as or different from each other, and may be each independently selected from the group consisting of hydrogen; deuterium; a substituted or unsubstituted linear or branched alkyl group having 1 to 10 carbon atoms; a substituted or unsubstituted monocyclic or polycyclic aryl group having 6 to 12 carbon atoms; a substituted or unsubstituted monocyclic or polycyclic heteroaryl group having 2 to 10 carbon atoms; and a substituted or unsubstituted sulfide group.

In one embodiment of the present specification, $R_{13}$ and $R_{14}$ are the same as or different from each other, and each independently a substituted or unsubstituted methyl group; a substituted or unsubstituted ethyl group; a substituted or unsubstituted propyl group; or a substituted or unsubstituted phenyl group.

In one embodiment of the present specification, $R_{13}$ and $R_{14}$ are the same as or different from each other, and may be each independently a methyl group; an ethyl group unsubstituted or substituted with a hydroxyl group or an amine group; a propyl group; or a phenyl group unsubstituted or substituted with a methyl group, an ethyl group, a propyl group, an isopropyl group, a butyl group, a methoxy group, a hydroxyl group, $—SO_3^-$, $—SO_3H$, $—SO_3^-Na^+$, $—SO_3^-K^+$ or $—SO_2NHRe$, and Re may be a linear or branched alkyl group having 1 to 30 carbon atoms.

In addition, $R_{15}$ may be selected from the group consisting of hydrogen; deuterium; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In one embodiment of the present specification, $R_{15}$ may be selected from the group consisting of hydrogen; deuterium; a substituted or unsubstituted linear or branched alkyl group having 1 to 20 carbon atoms; a substituted or unsubstituted monocyclic or polycyclic aryl group having 6 to 20 carbon atoms; and a substituted or unsubstituted monocyclic or polycyclic heteroaryl group having 2 to 20 carbon atoms.

In one embodiment of the present specification, $R_{15}$ may be selected from the group consisting of hydrogen; deuterium; a substituted or unsubstituted linear or branched alkyl group having 1 to 10 carbon atoms; a substituted or unsubstituted monocyclic or polycyclic aryl group having 6 to 12 carbon atoms; and a substituted or unsubstituted monocyclic or polycyclic heteroaryl group having 2 to 10 carbon atoms.

In one embodiment of the present specification, $R_{15}$ may be hydrogen; or a substituted or unsubstituted monocyclic or polycyclic aryl group having 6 to 12 carbon atoms.

In one embodiment of the present specification, $R_{15}$ may be a substituted or unsubstituted phenyl group.

In one embodiment of the present specification, $R_{15}$ may be a phenyl group.

$L_1$ is selected from the group consisting of a direct bond; a substituted or unsubstituted linear or branched alkylene group having 1 to 30 carbon atoms; $—NH—$; $—O—$; $—COO—$; $—OCO—$; $—NHCO—$; $—CONH—$; $—NR—$; $—NRCO—$; $-L_3-NH-L_4-$; $-L_3-O-L_4-$; $-L_3-COO-L_4-$; $-L_3-OCO-L_4-$; $-L_3-NHCO-L_4-$; $-L_3-CONH-L_4-$; $-L_3-NR-L_4-$; and $-L_3-NRCO-L_4-$.

In another embodiment of the present specification, $L_1$ may be a direct bond; a substituted or unsubstituted linear or branched alkylene group having 1 to 30 carbon atoms; $-L_3-NH-L_4-$; or $-L_3-O-L_4-$.

In another embodiment of the present specification, $L_1$ may be a direct bond; a substituted or unsubstituted linear or branched alkylene group having 1 to 20 carbon atoms; $-L_3-NH-L_4-$; or $-L_3-O-L_4-$.

In another embodiment of the present specification, $L_1$ may be a direct bond; a substituted or unsubstituted linear or branched alkylene group having 1 to 10 carbon atoms; $-L_3-NH-L_4-$; or $-L_3-O-L_4-$.

In another embodiment of the present specification, $L_1$ may be a methylene group; an ethylene group; a propylene group; $-L_3-NH-L_4-$; or $-L_3-O-L_4-$.

In addition, $L_2$ is selected from the group consisting of a direct bond; a substituted or unsubstituted linear or branched alkylene group having 1 to 30 carbon atoms; $—NH—$; $—O—$; $—COO—$; $—OCO—$; $—NHCO—$; $—CONH—$; $—NR—$; $—NRCO—$; $-L_3-NH-L_4-$; $-L_3-O-L_4-$; $-L_3-COO-L_4-$; $-L_3-OCO-L_4-$; $-L_3-NHCO-L_4-$; $-L_3-CONH-L_4-$; $-L_3-NR-L_4-$; and $-L_3-NRCO-L_4-$.

In one embodiment of the present specification, $L_2$ may be a substituted or unsubstituted linear or branched alkylene group having 1 to 30 carbon atoms; $-L_3-NH-L_4-$; or $-L_3-O-L_4-$.

In one embodiment of the present specification, $L_2$ may be a substituted or unsubstituted linear or branched alkylene group having 1 to 20 carbon atoms; $-L_3-NH-L_4-$; or $-L_3-O-L_4-$.

In one embodiment of the present specification, $L_2$ may be a substituted or unsubstituted linear or branched alkylene group having 1 to 10 carbon atoms; $-L_3-NH-L_4-$; or $-L_3-O-L_4-$.

In one embodiment of the present specification, $L_2$ may be a methylene group; an ethylene group; a propylene group; $-L_3-NH-L_4-$; or $-L_3-O-L_4-$.

In one embodiment of the present specification, $L_3$ and $L_4$ are a substituted or unsubstituted linear or branched alkylene group having 1 to 30 carbon atoms.

In another embodiment of the present specification, $L_3$ and $L_4$ may be a substituted or unsubstituted linear or branched alkylene group having 1 to 20 carbon atoms.

In another embodiment of the present specification, $L_3$ and $L_4$ may be a substituted or unsubstituted linear or branched alkylene group having 1 to 10 carbon atoms.

In another embodiment of the present specification, $L_3$ and $L_4$ may be a substituted or unsubstituted ethylene group; or a substituted or unsubstituted propylene group.

In another embodiment of the present specification, $L_3$ and $L_4$ may be an ethylene group; or a propylene group.

R is selected from the group consisting of a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In one embodiment of the present specification, R is selected from the group consisting of a substituted or unsubstituted linear or branched alkyl group having 1 to 20 carbon atoms; a substituted or unsubstituted monocyclic or polycyclic aryl group having 6 to 20 carbon atoms; and a substituted or unsubstituted monocyclic or polycyclic heteroaryl group having 2 to 20 carbon atoms.

In another embodiment, R is selected from the group consisting of a substituted or unsubstituted linear or branched alkyl group having 1 to 10 carbon atoms; a substituted or unsubstituted monocyclic or polycyclic aryl group having 6 to 12 carbon atoms; and a substituted or unsubstituted monocyclic or polycyclic heteroaryl group having 2 to 10 carbon atoms.

In addition, X is selected from the group consisting of an anion of a compound containing oxygen and at least one element selected from the group consisting of tungsten, molybdenum, silicon and phosphorous; a trifluoromethanesulfonic acid anion; a bis(trifluoromethylsulfonyl)amide anion; a bistrifluoromethanesulfonimide anion; a bisperfluoroethylsulfonimide anion; a tetraphenylborate anion; tetrakis(4-fluorophenyl)borate; tetrakis(pentafluorophenyl)borate; tristrifluoromethanesulfonylmethide; and a halogen group.

In one embodiment of the present specification, X may be a bistrifluoromethanesulfonimide anion; or tristrifluoromethanesulfonylmethide.

In another embodiment of the present specification, a is 0.

In another embodiment of the present specification, a is 1.

According to another embodiment of the present specification, Chemical Formula 1 may provide a compound represented by the following Chemical Formula 2.

[Chemical Formula 2]

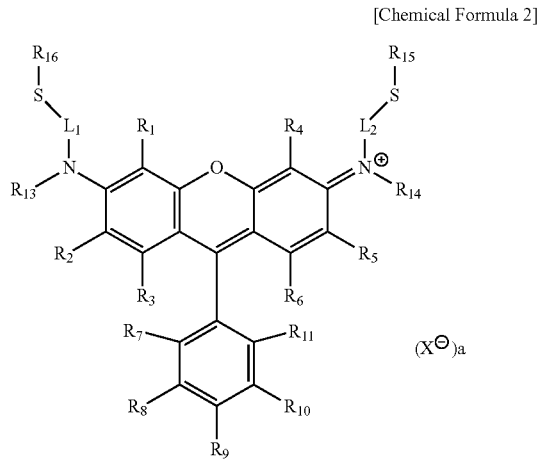

$(X^\ominus)_a$

In Chemical Formula 2, $R_1$ to $R_{11}$, $R_{13}$ to $R_{15}$, $L_1$, $L_2$, a and X have the same definitions as in Chemical Formula 1, and $R_{16}$ may be selected from the group consisting of hydrogen; deuterium; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In another embodiment of the present specification, $R_{16}$ may be selected from the group consisting of hydrogen; deuterium; a substituted or unsubstituted linear or branched alkyl group having 1 to 20 carbon atoms; a substituted or unsubstituted monocyclic or polycyclic aryl group having 6 to 20 carbon atoms; and a substituted or unsubstituted monocyclic or polycyclic heteroaryl group having 2 to 20 carbon atoms.

In another embodiment of the present specification, $R_{16}$ may be selected from the group consisting of hydrogen; deuterium; a substituted or unsubstituted linear or branched alkyl group having 1 to 10 carbon atoms; a substituted or unsubstituted monocyclic or polycyclic aryl group having 6 to 12 carbon atoms; and a substituted or unsubstituted monocyclic or polycyclic heteroaryl group having 2 to 10 carbon atoms.

In another embodiment of the present specification, $R_{16}$ may be selected from the group consisting of hydrogen; deuterium; a substituted or unsubstituted monocyclic or polycyclic aryl group having 6 to 30 carbon atoms; and a substituted or unsubstituted monocyclic or polycyclic heteroaryl group having 2 to 30 carbon atoms.

In another embodiment of the present specification, $R_{16}$ may be selected from the group consisting of hydrogen; deuterium; a substituted or unsubstituted monocyclic or polycyclic aryl group having 6 to 20 carbon atoms; and a substituted or unsubstituted monocyclic or polycyclic heteroaryl group having 2 to 20 carbon atoms.

In another embodiment of the present specification, $R_{16}$ may be selected from the group consisting of hydrogen; deuterium; a substituted or unsubstituted monocyclic or polycyclic aryl group having 6 to 12 carbon atoms; and a substituted or unsubstituted monocyclic or polycyclic heteroaryl group having 2 to 10 carbon atoms.

In another embodiment of the present specification, $R_{16}$ may be hydrogen; a substituted or unsubstituted monocyclic or polycyclic aryl group having 6 to 12 carbon atoms.

In another embodiment of the present specification, $R_{16}$ may be a substituted or unsubstituted phenyl group.

In another embodiment of the present specification, $R_{16}$ may be a phenyl group.

In one embodiment of the present specification, the compound represented by Chemical Formula 1 may be represented by any one of the following chemical formulae, but is not limited thereto.

15
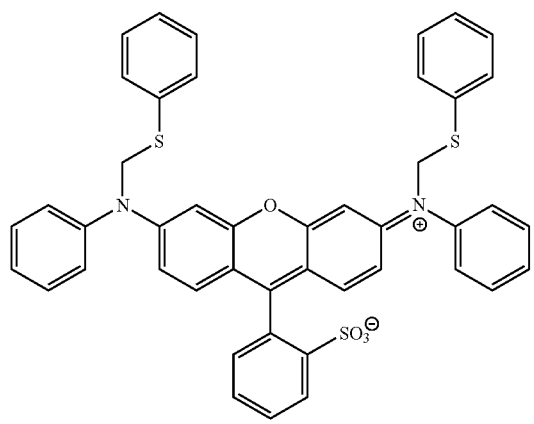
16
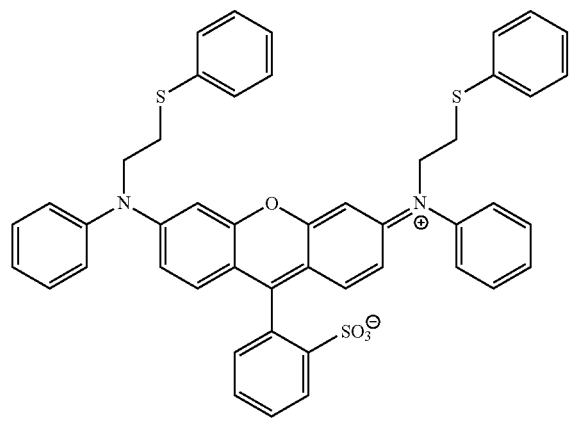
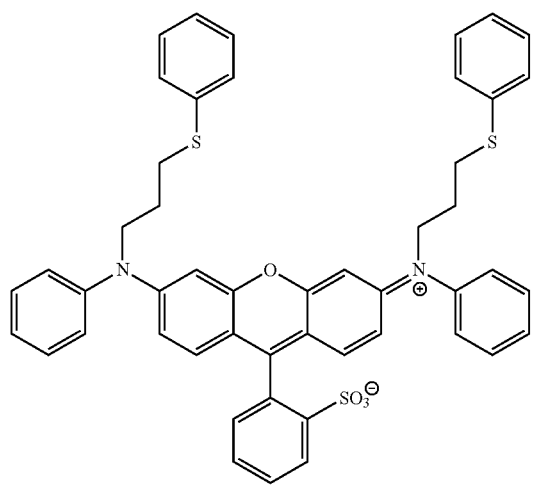
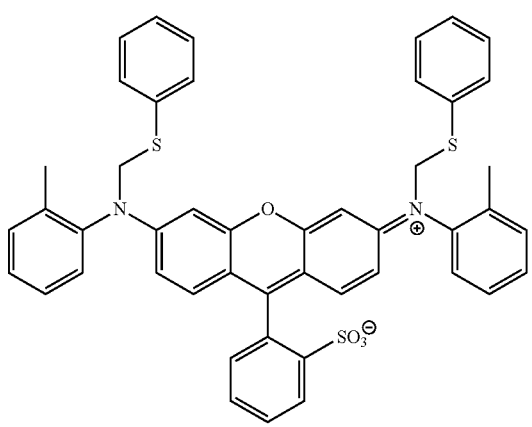
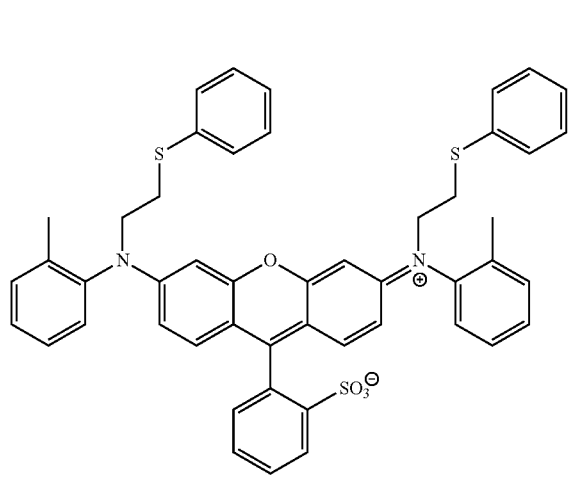

-continued
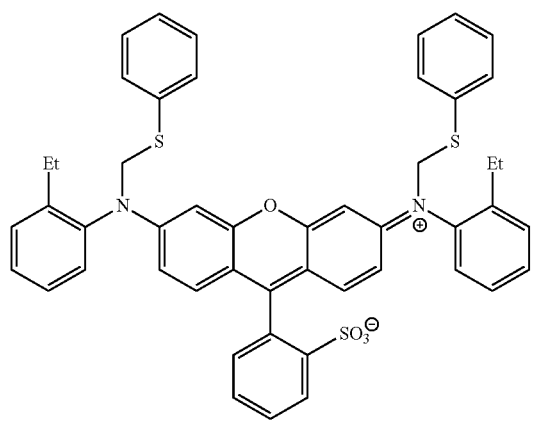
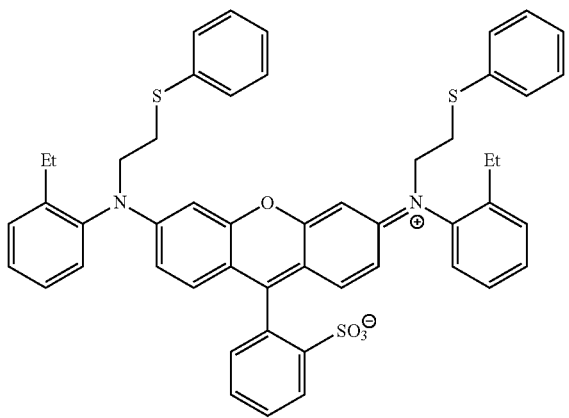
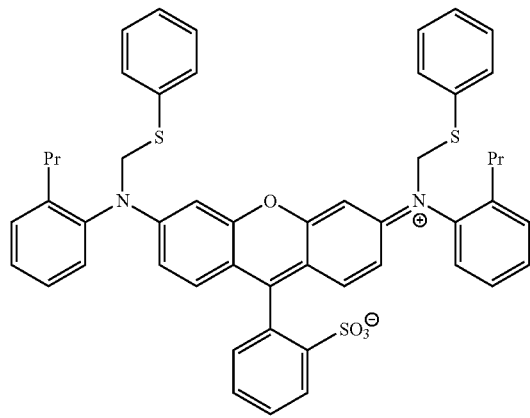
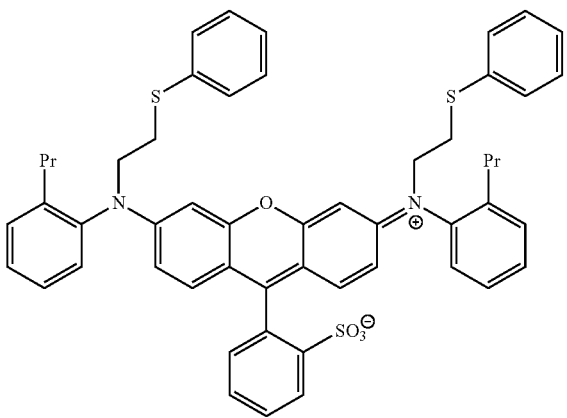
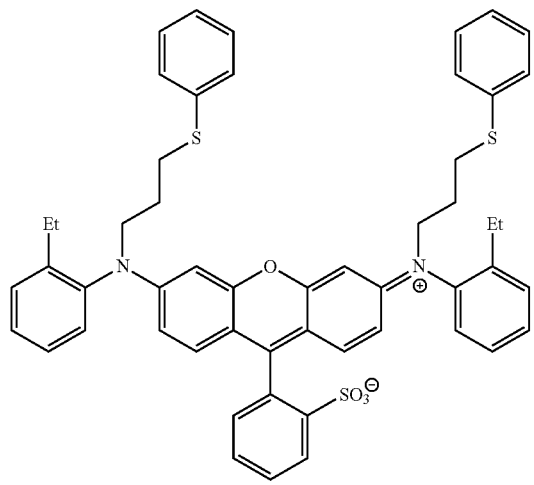
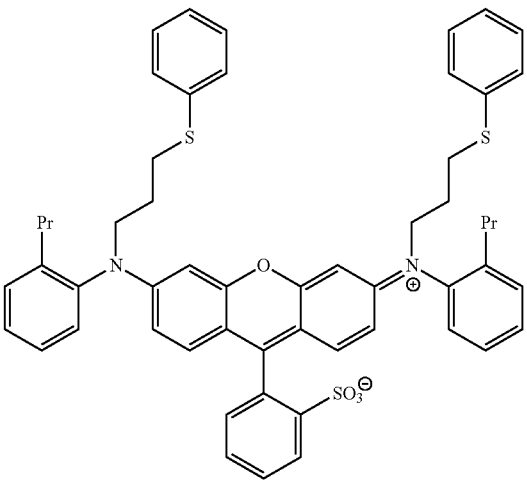

-continued
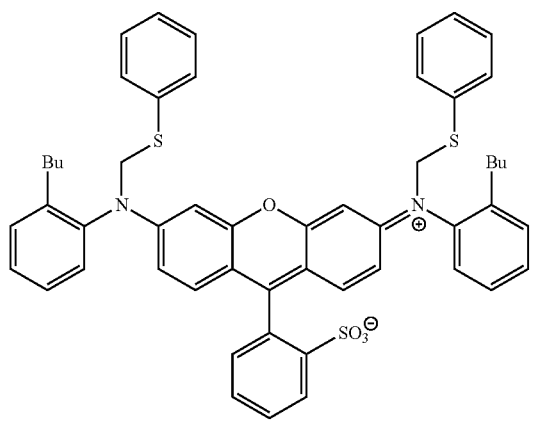
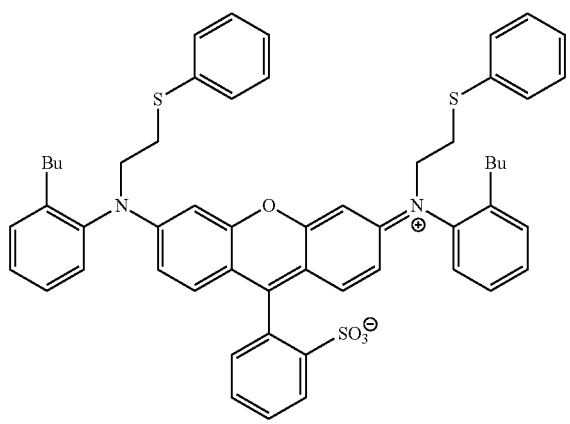
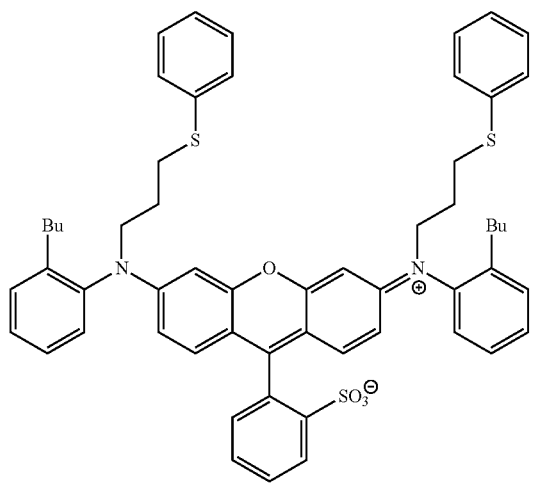
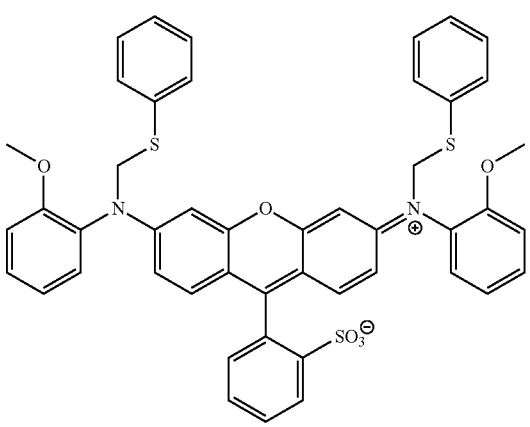
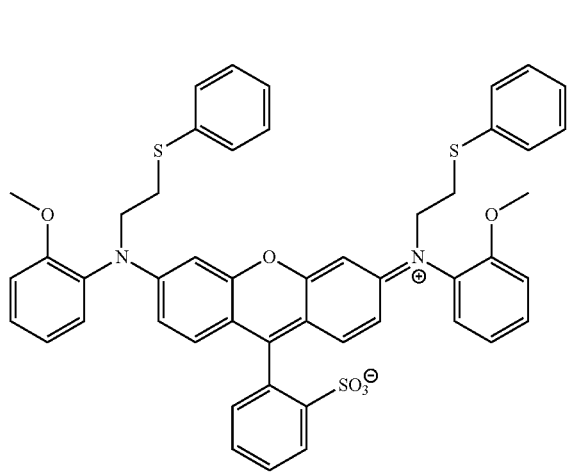
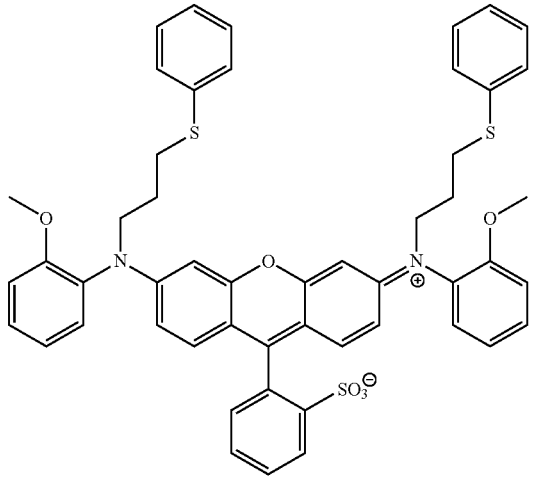

-continued
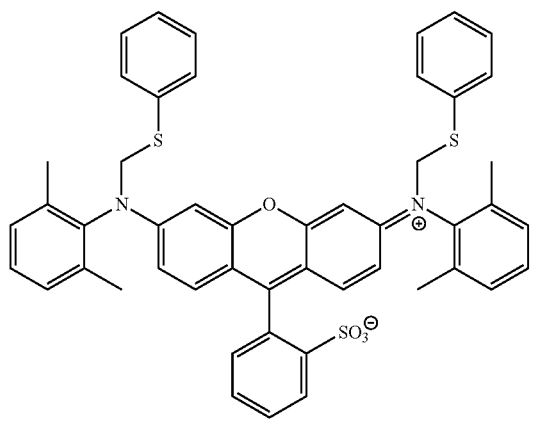
21
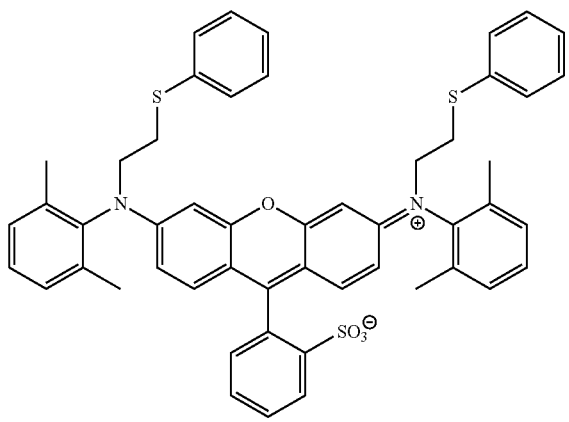
22
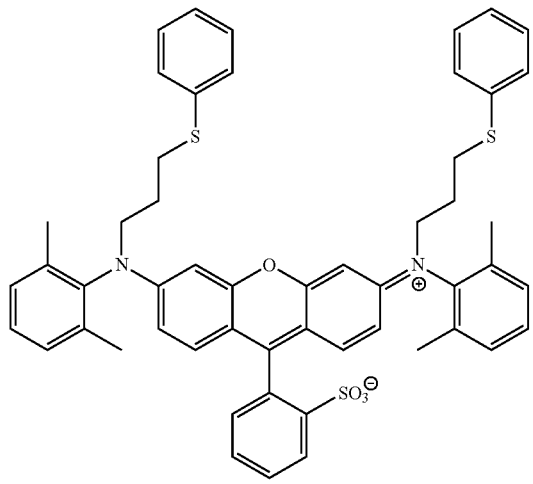
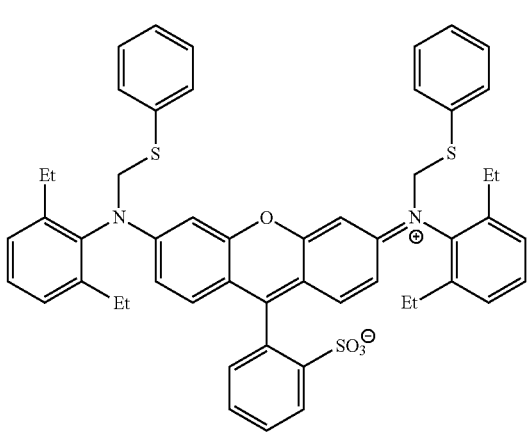
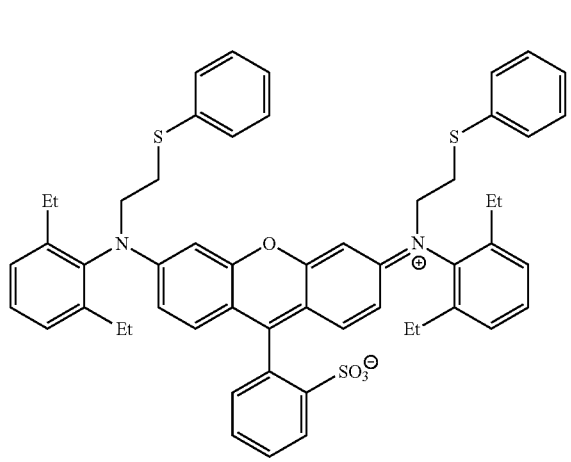
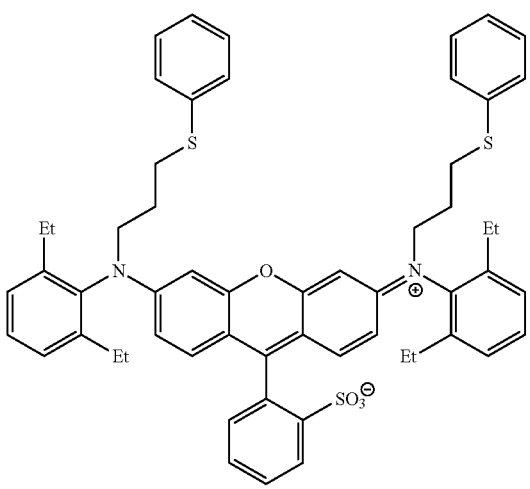

-continued
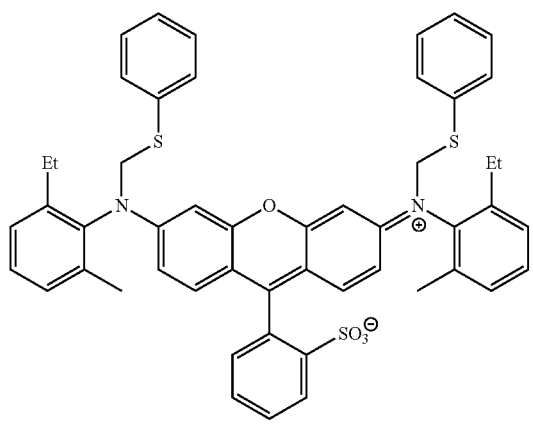
23
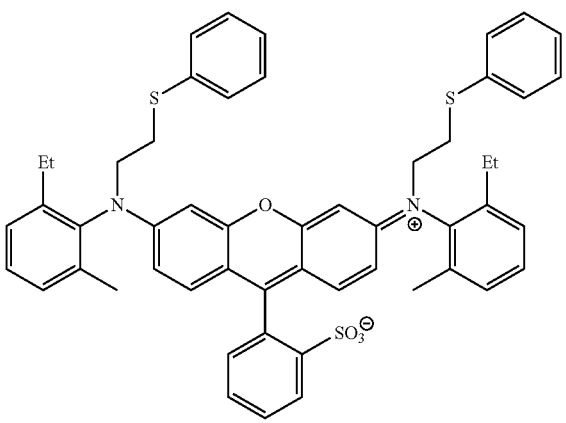
24
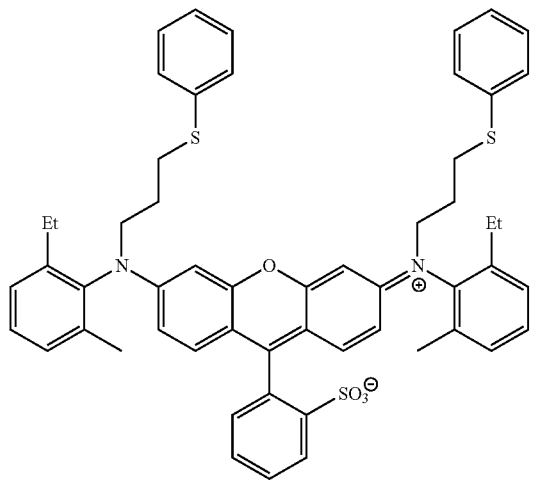
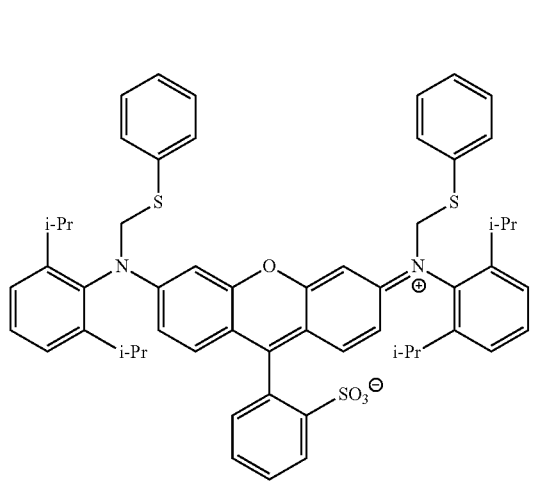

25 26
-continued
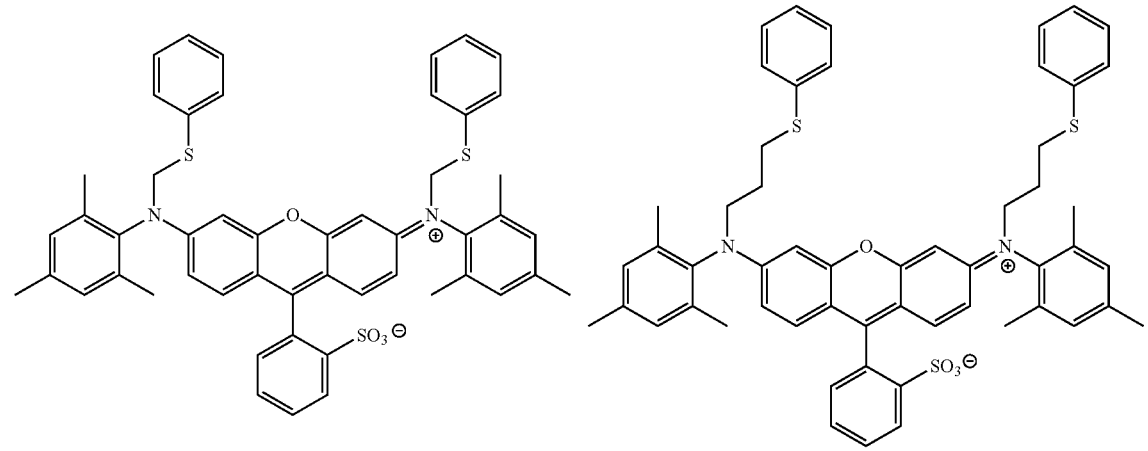
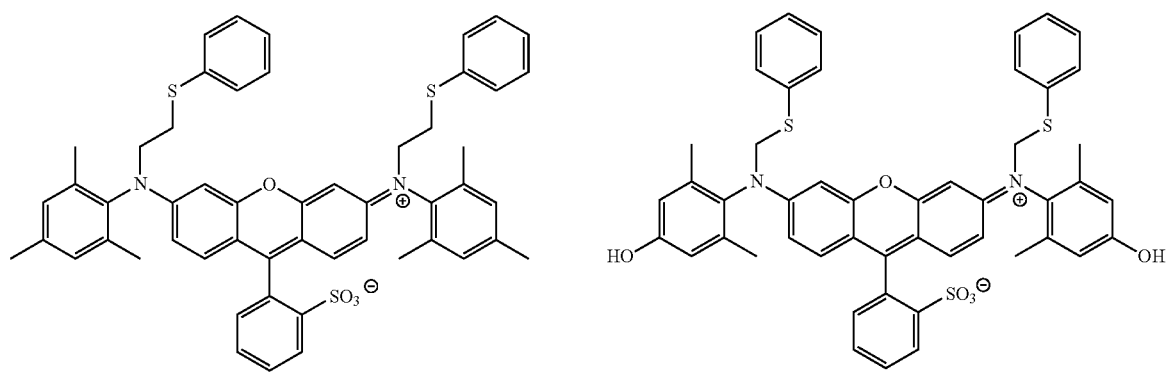
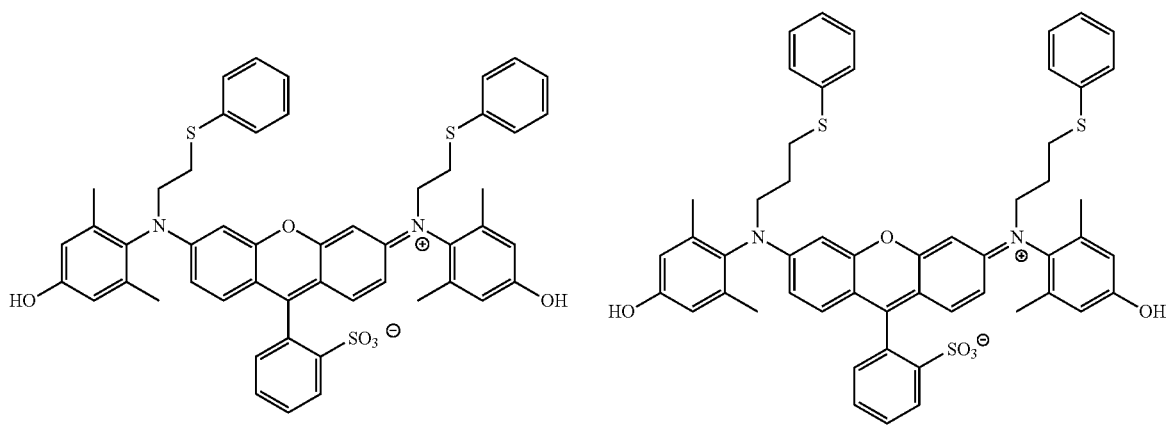
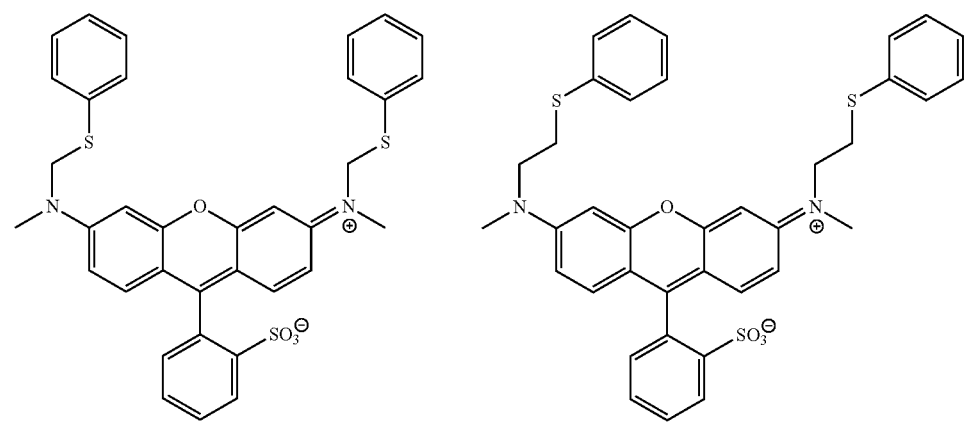

-continued
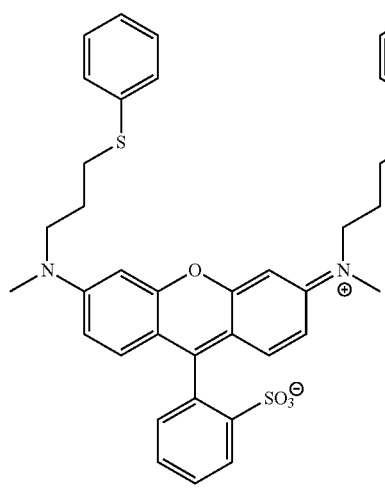
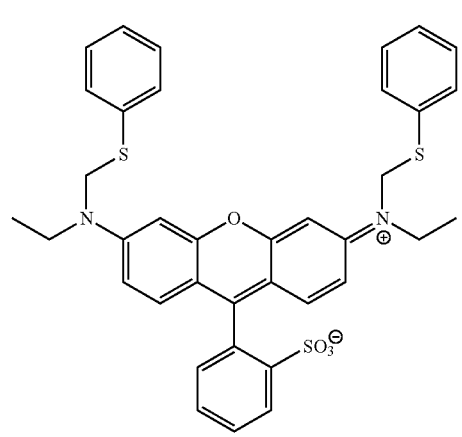
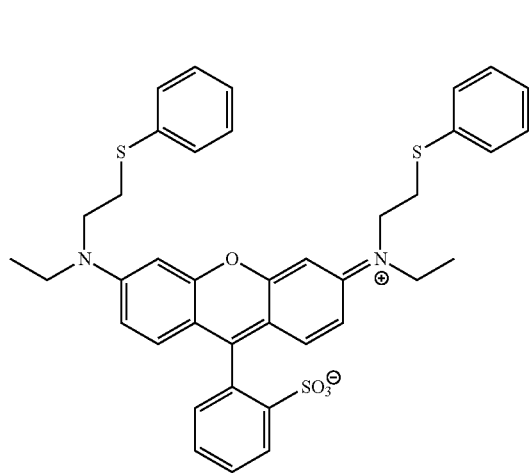
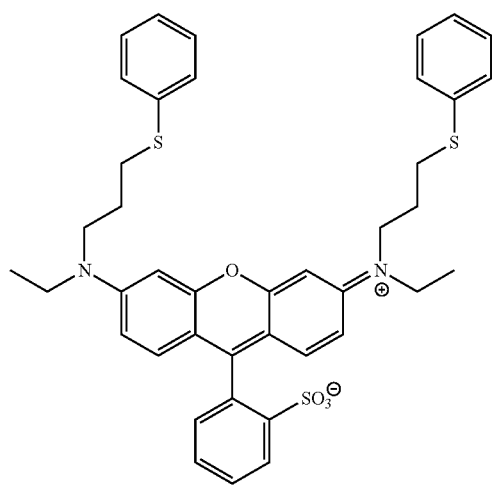
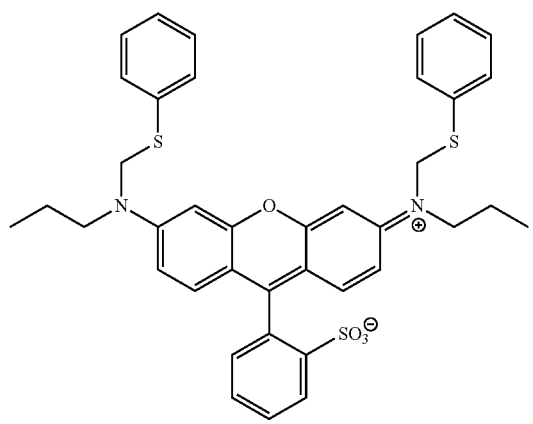
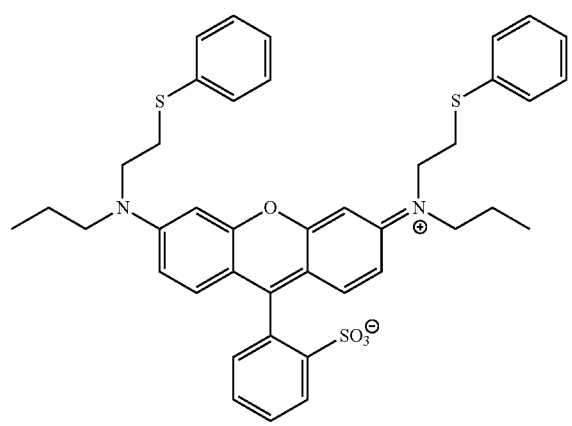

29
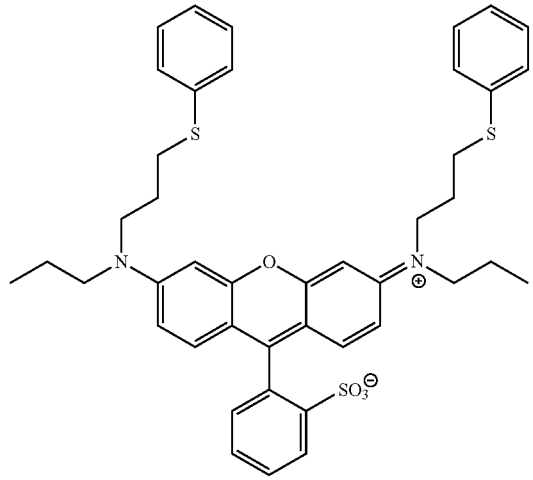
30
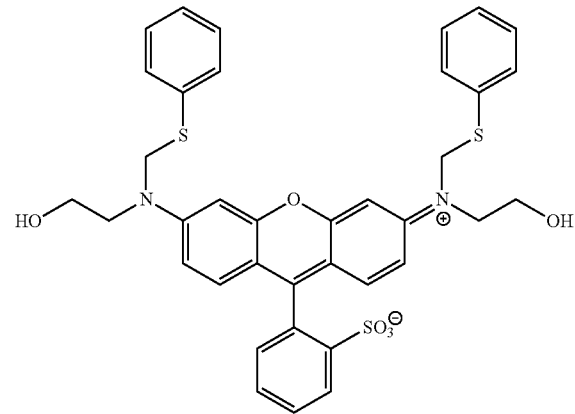
-continued
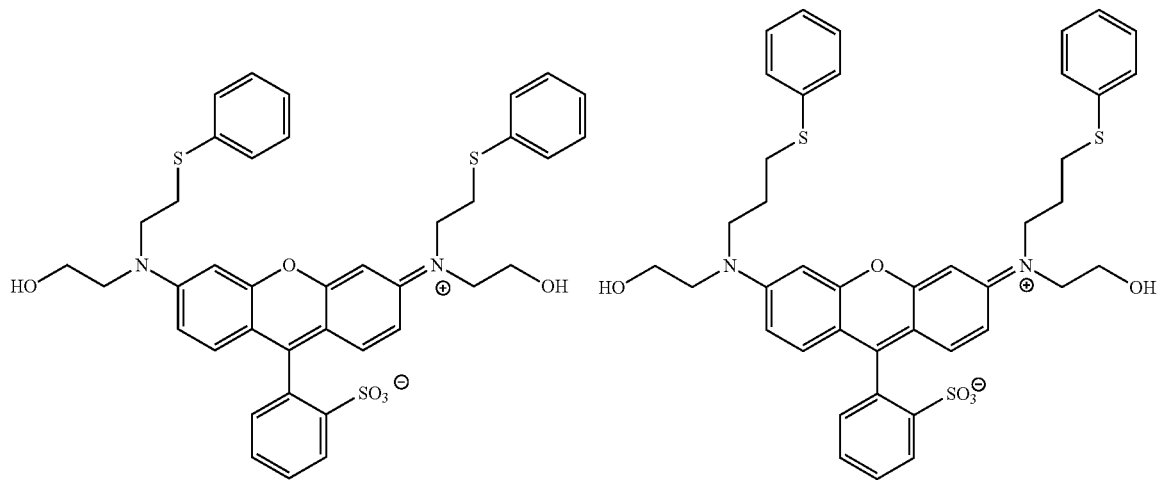
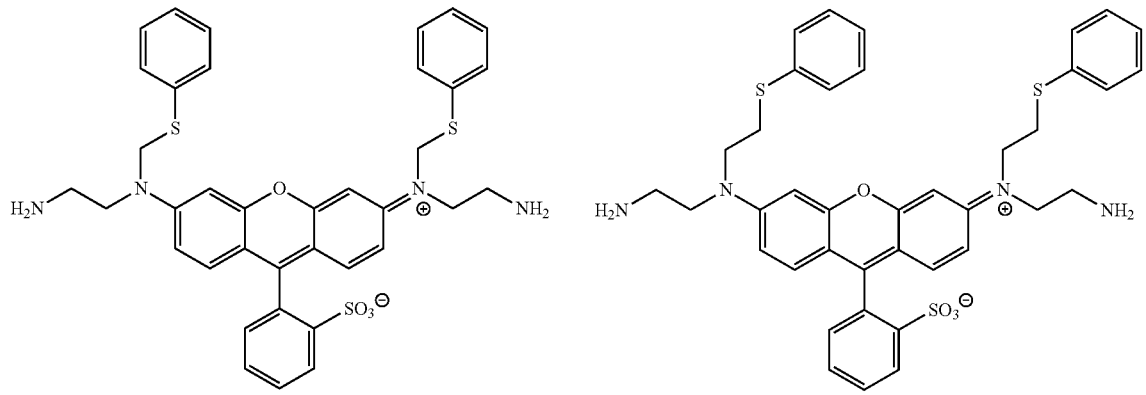

-continued
31
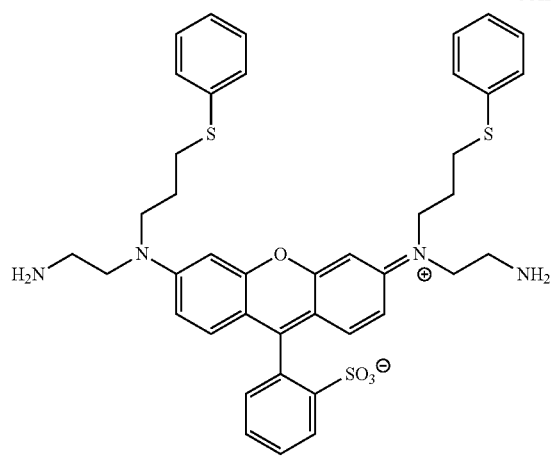
32
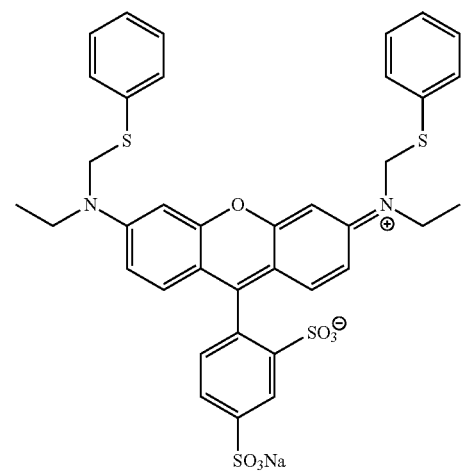
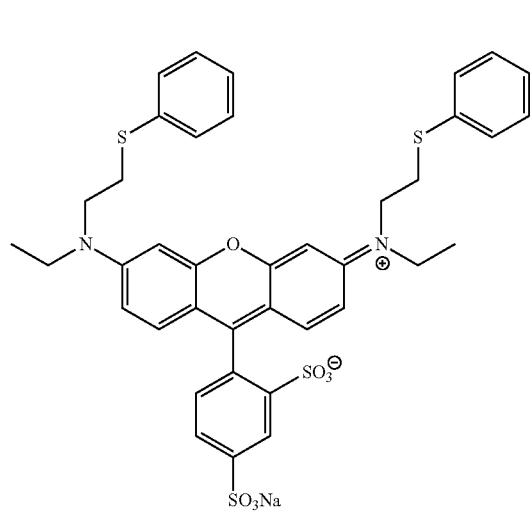
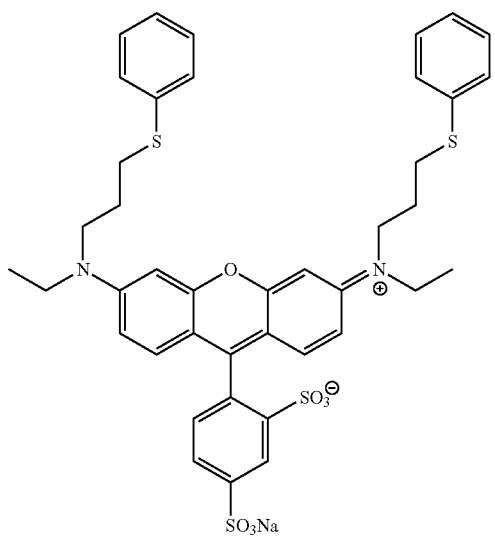
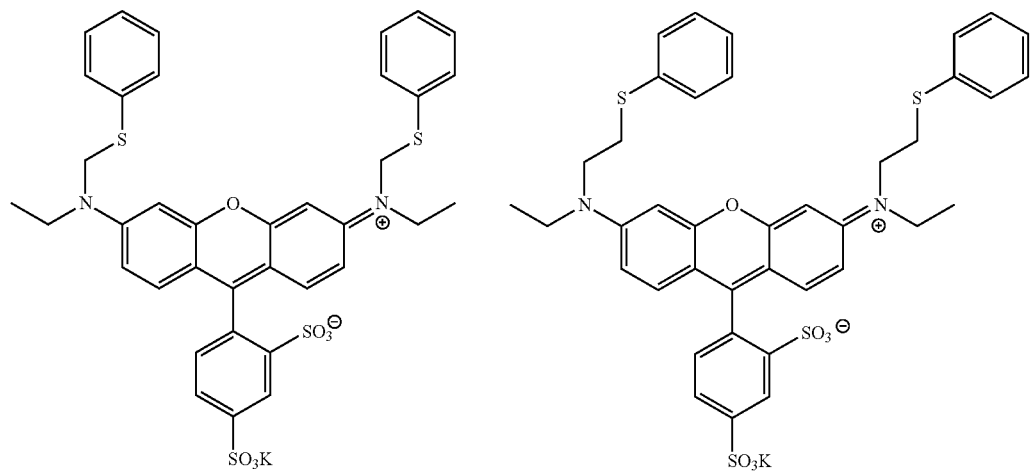

-continued
33
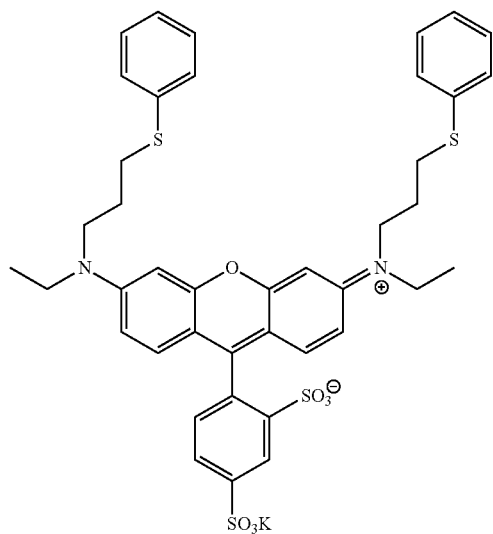
34
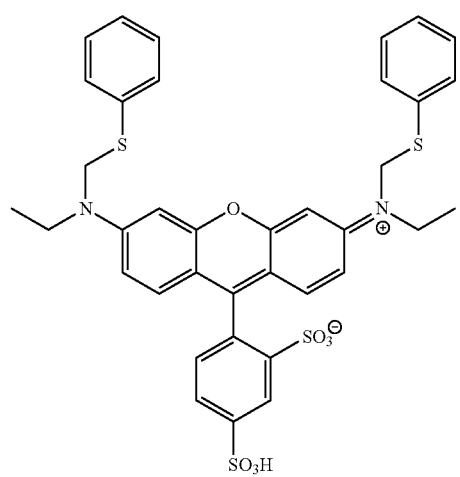
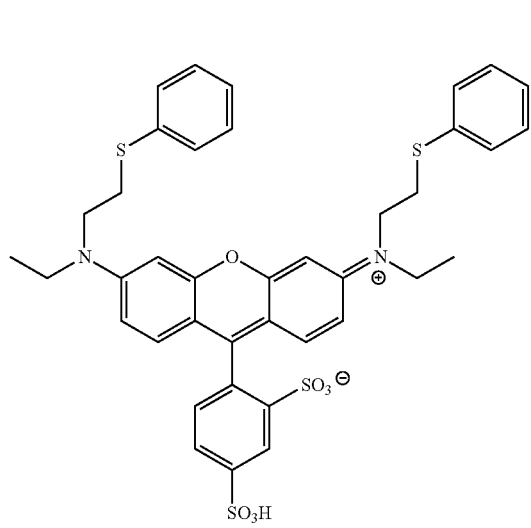
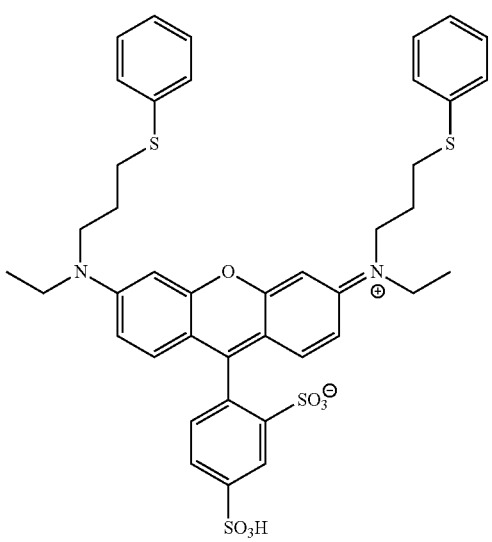
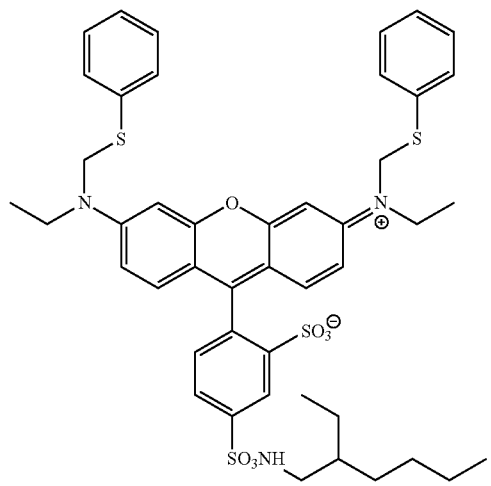

-continued
35
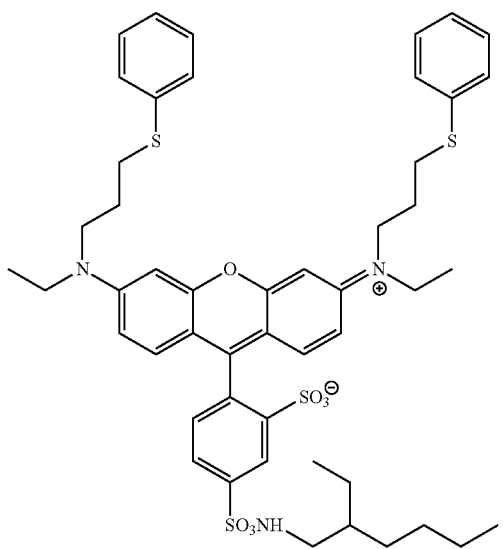
36
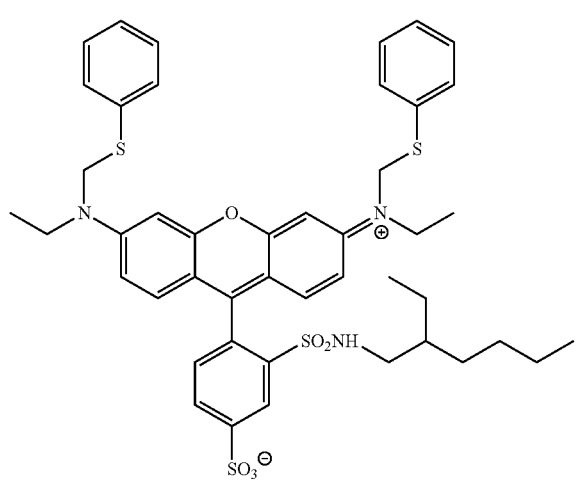
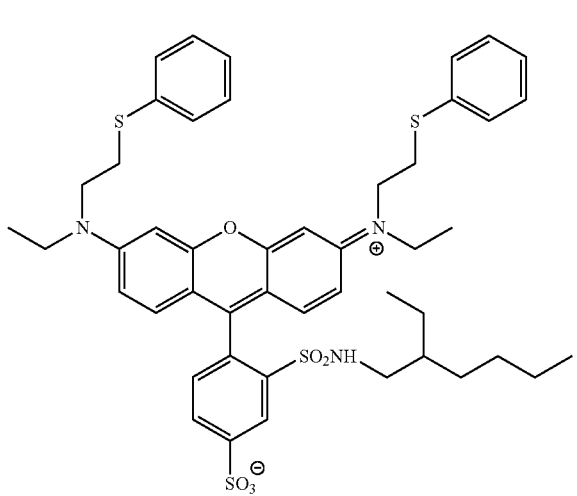
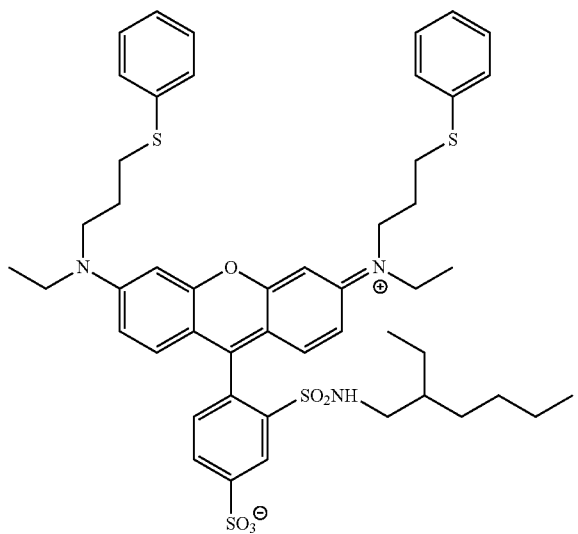
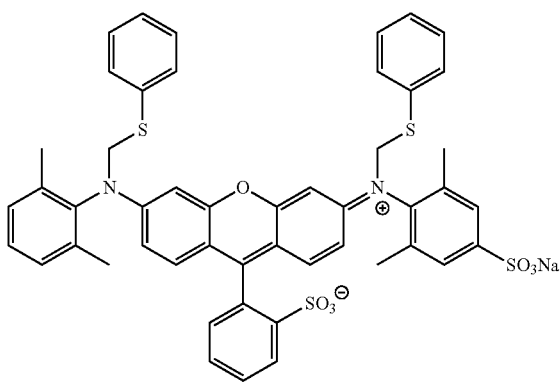
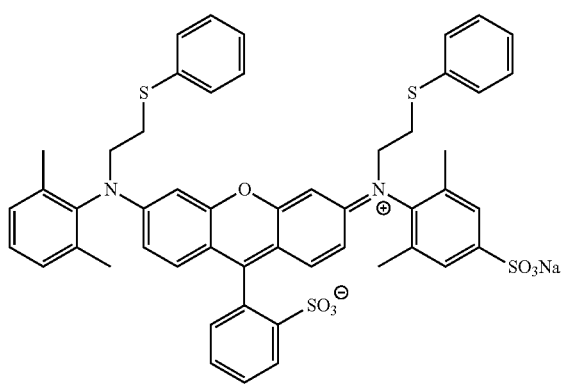

37 38
-continued
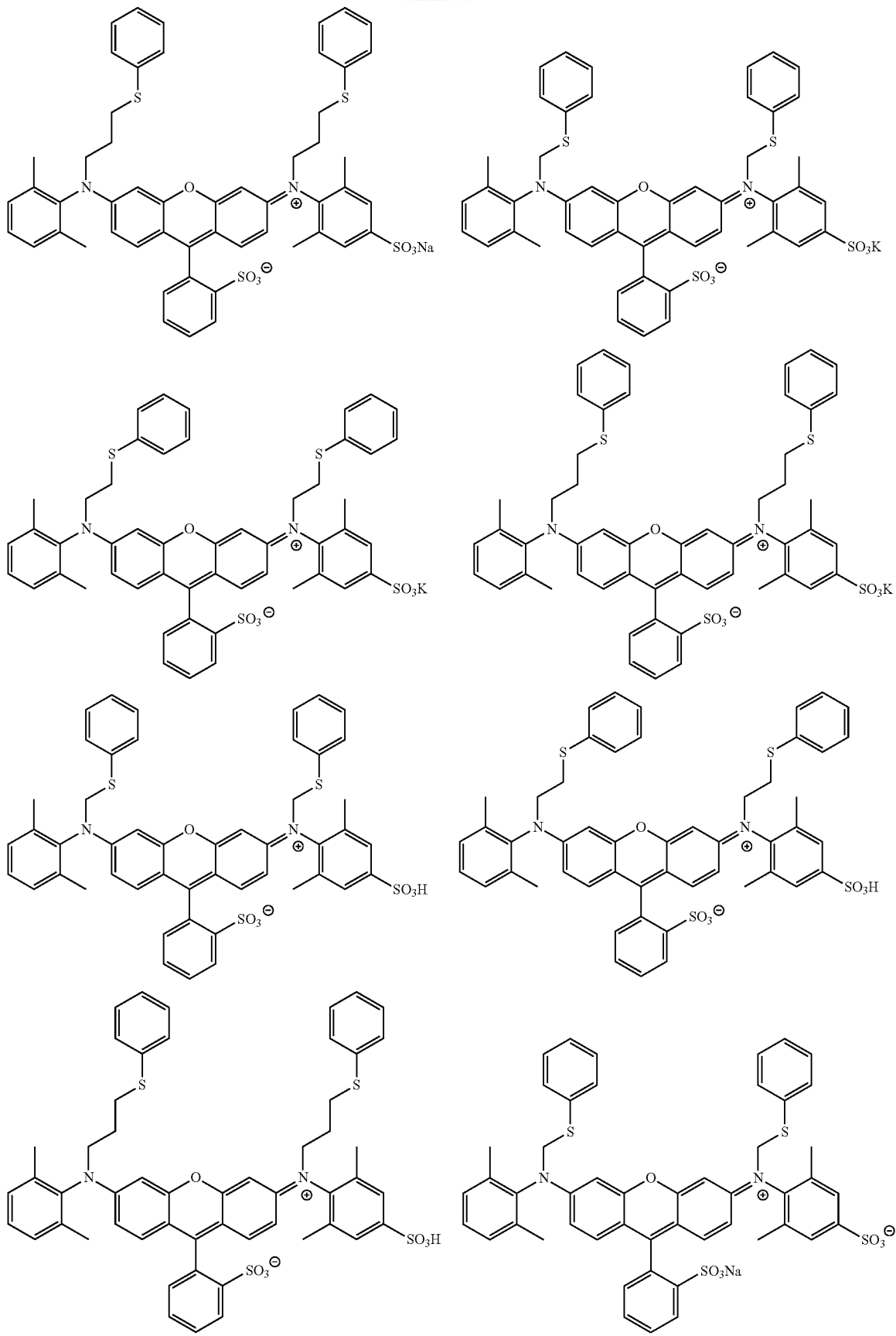

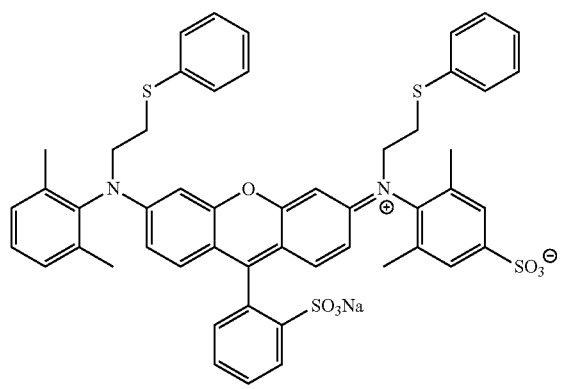
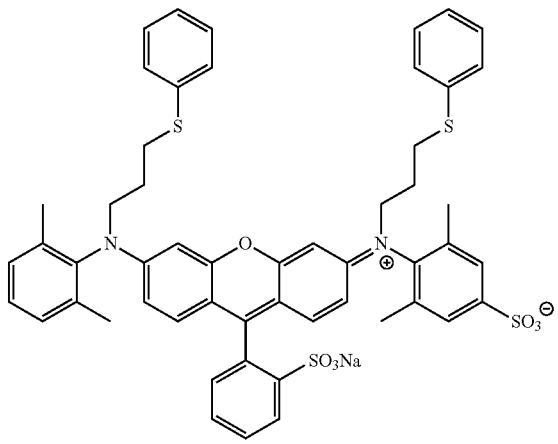
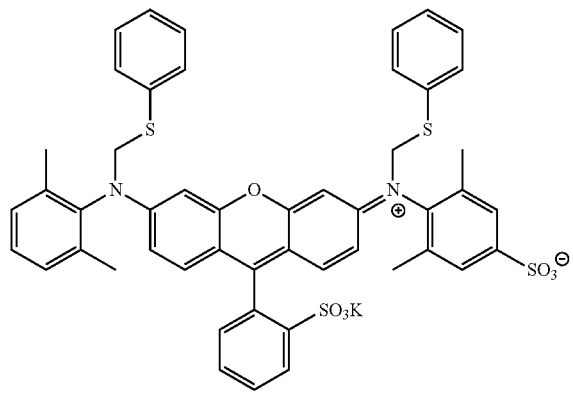
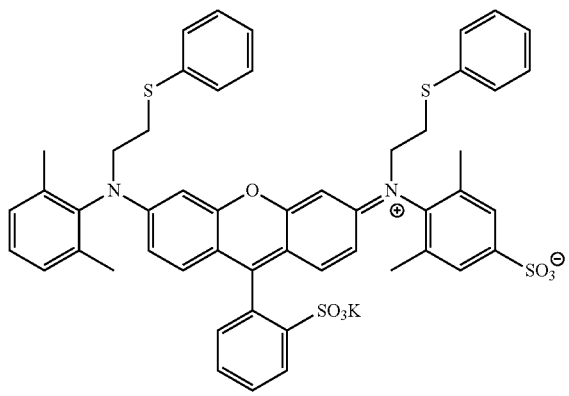
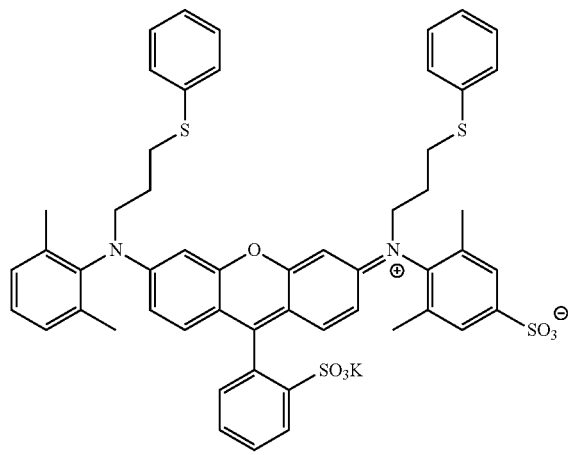
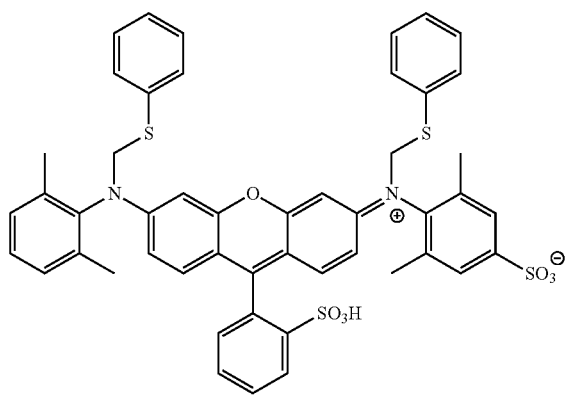

41
42
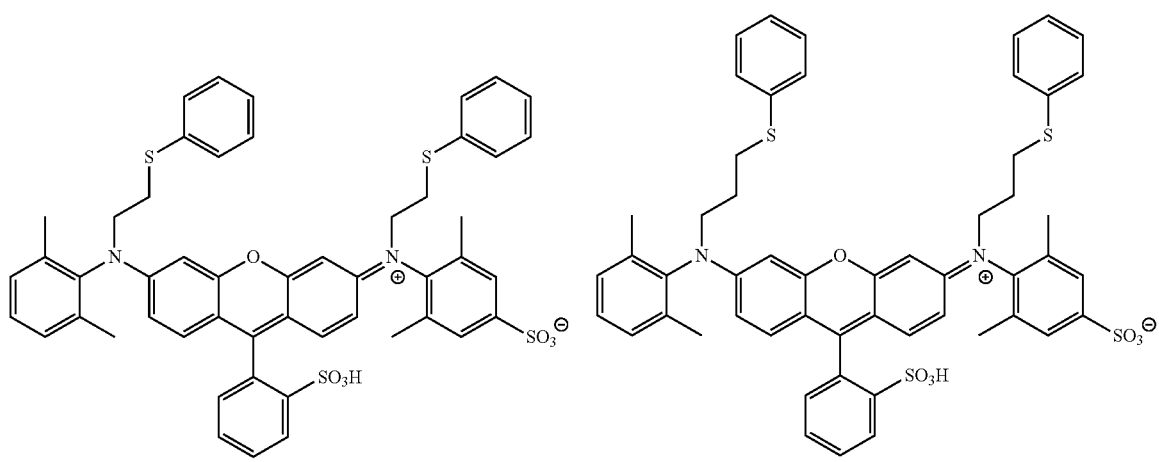
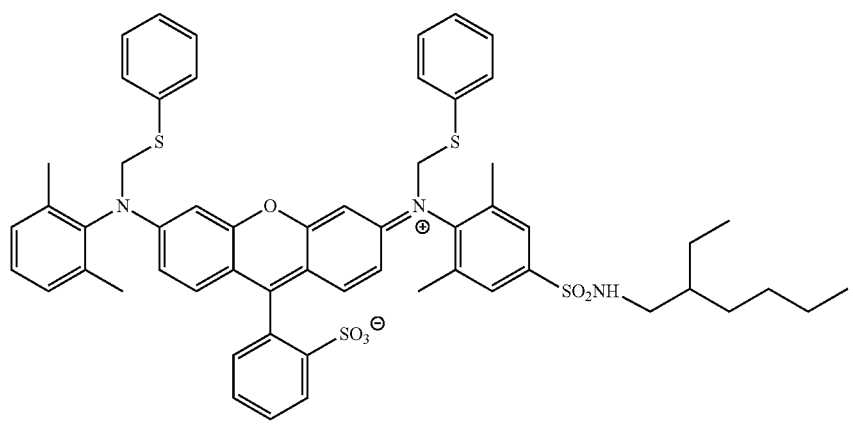
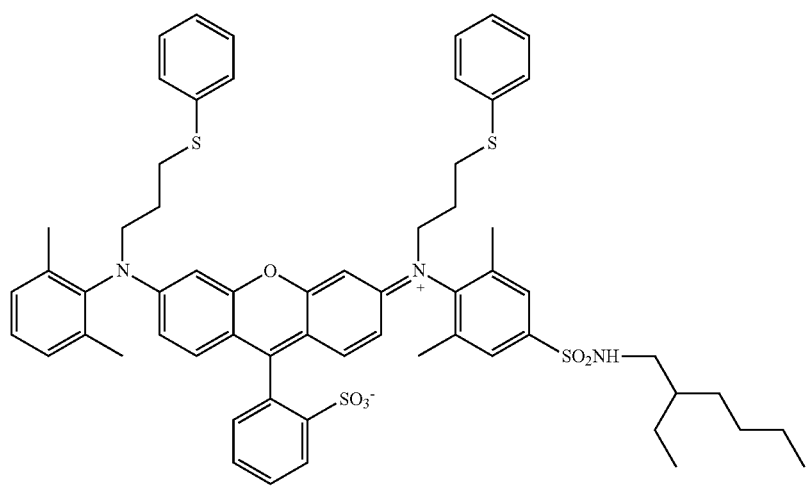

-continued
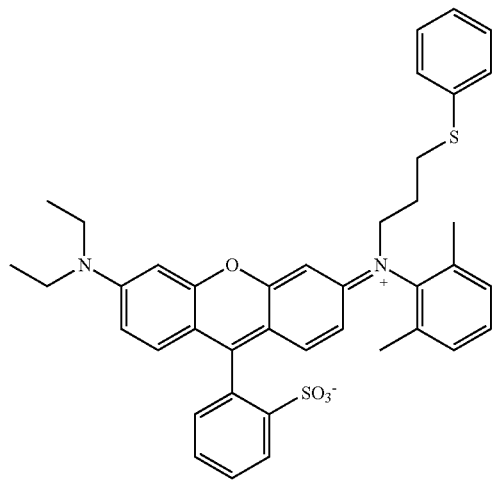
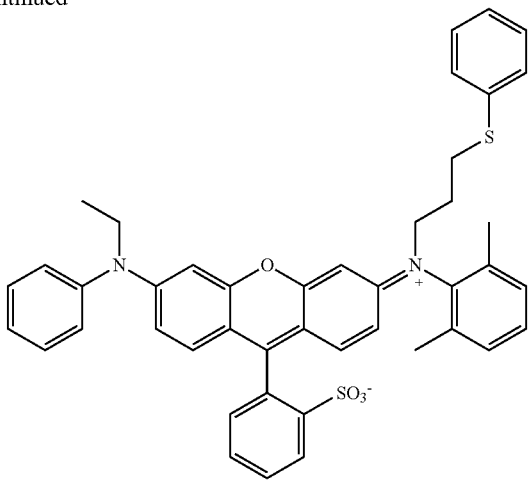
-continued
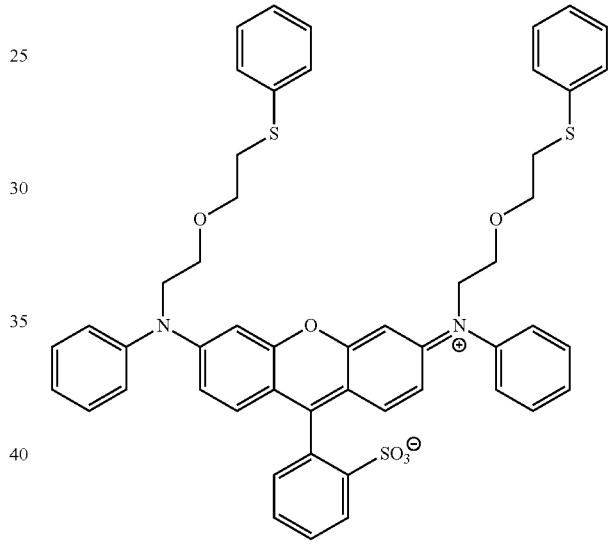
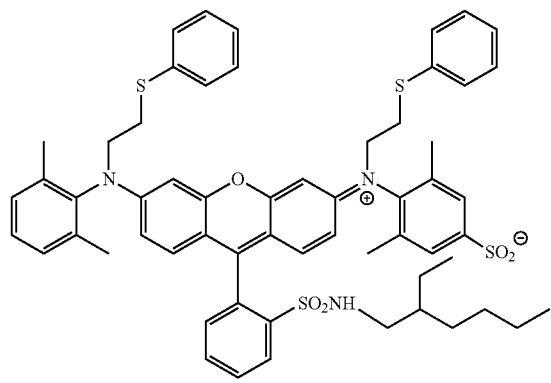
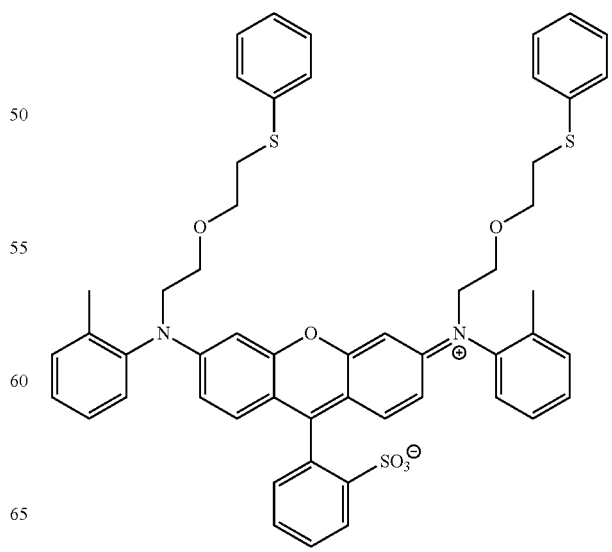

45
-continued
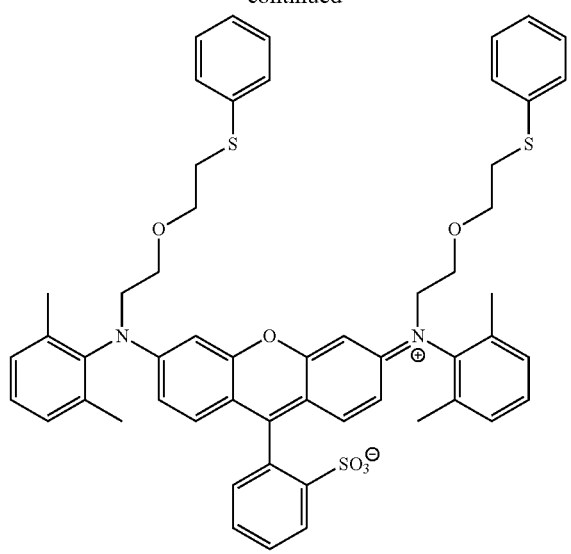
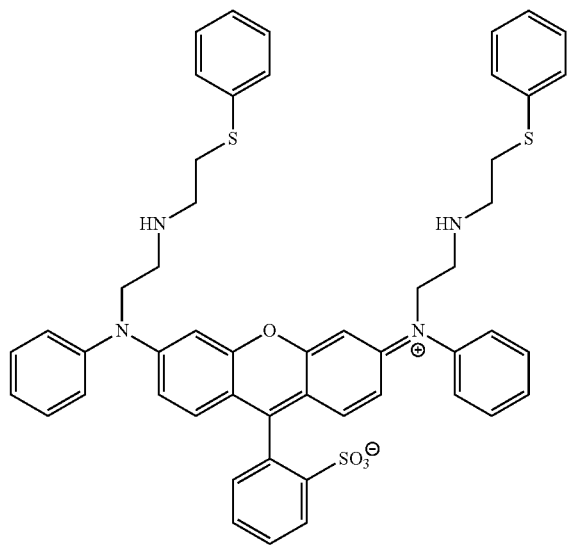
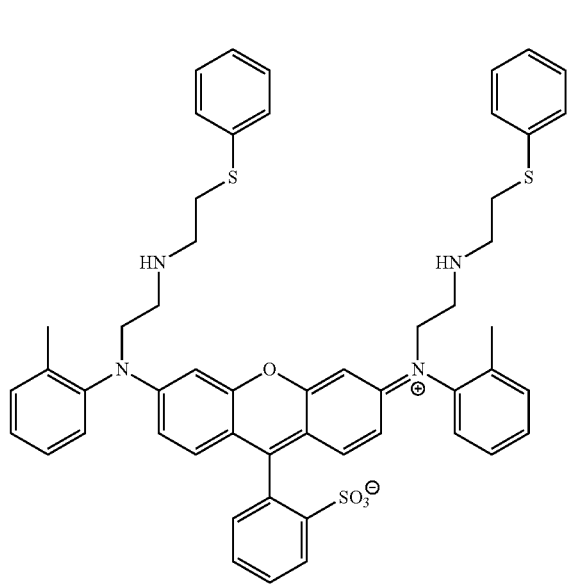
46
-continued
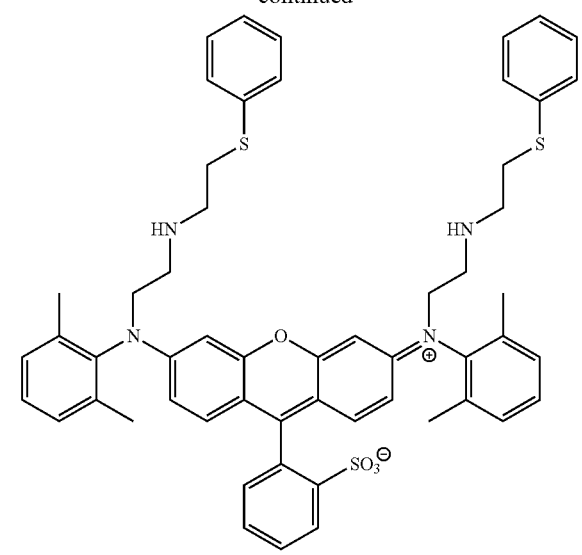
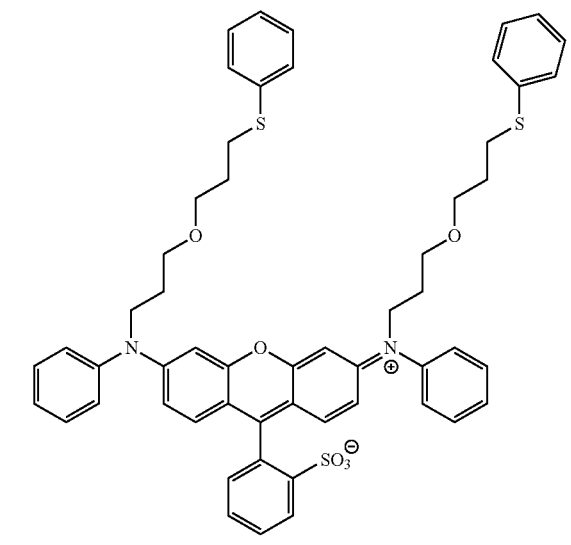
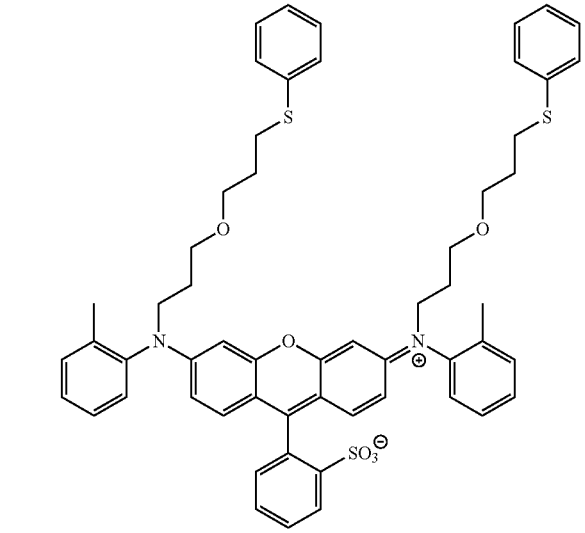

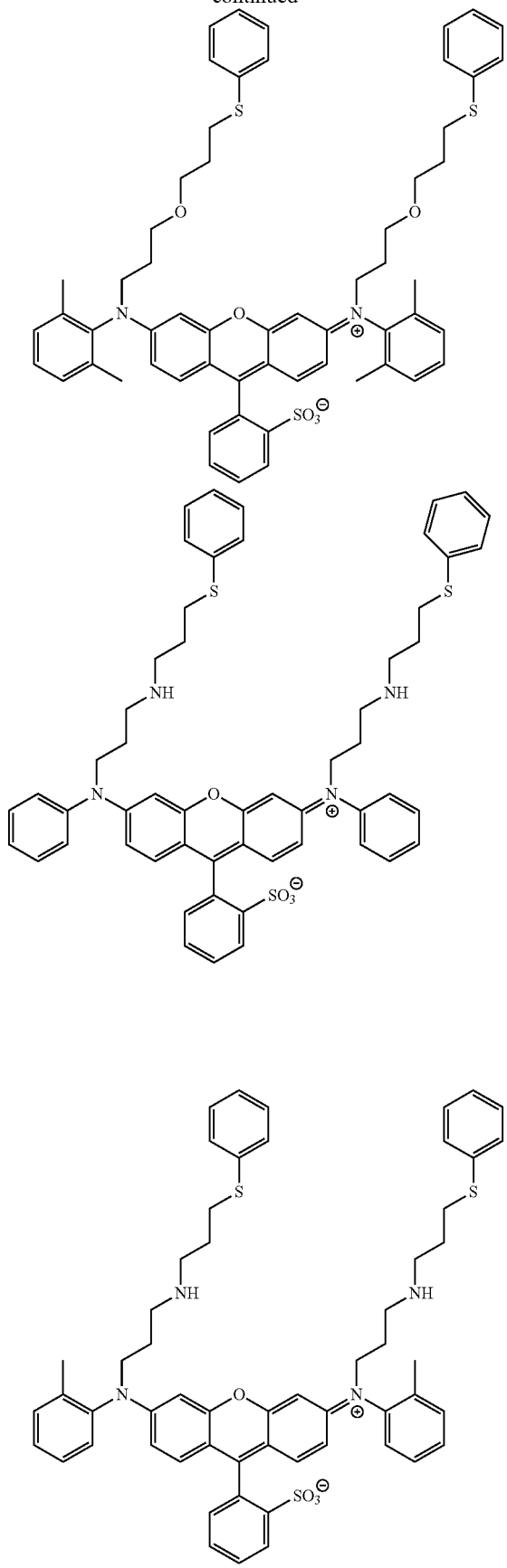
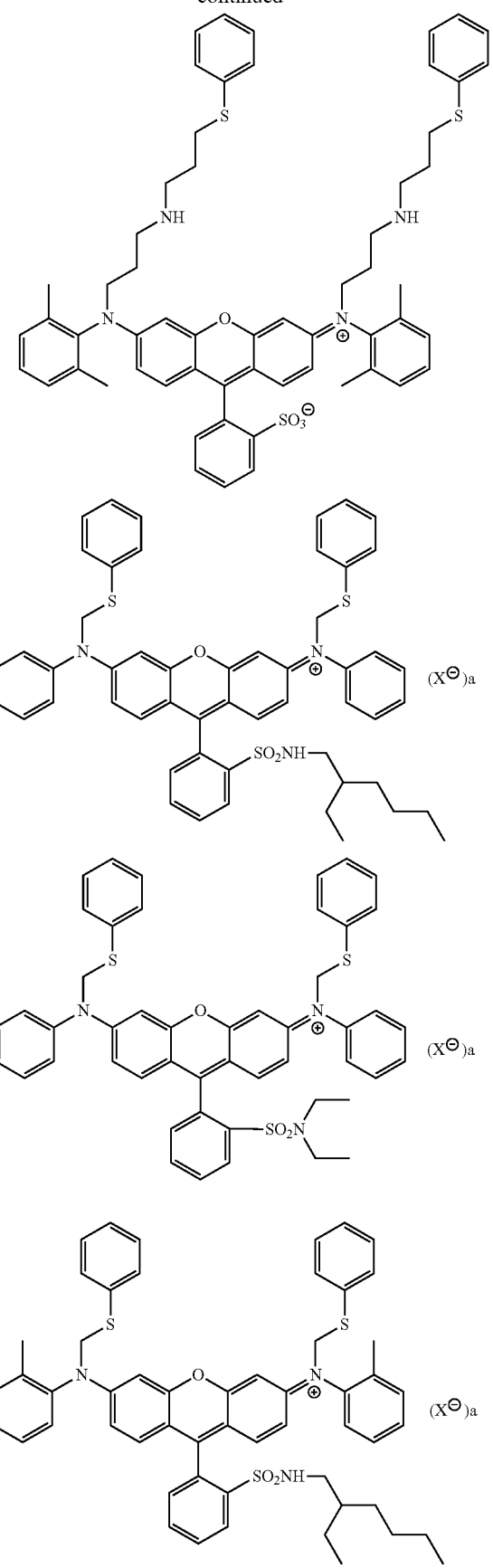

49
-continued
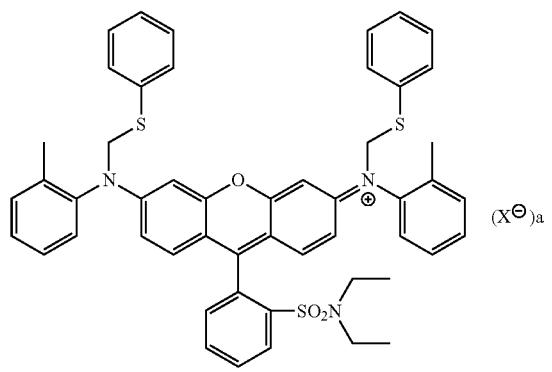
50
-continued
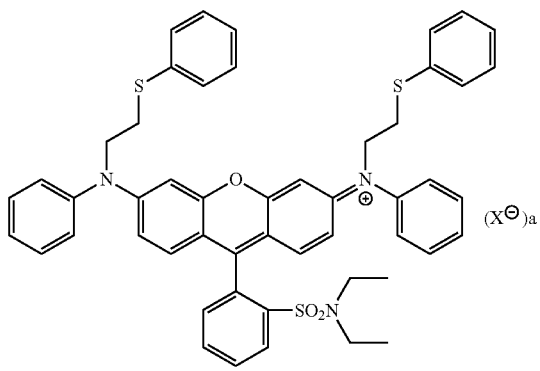
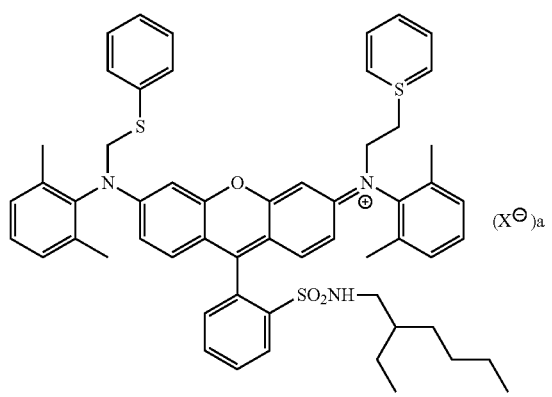
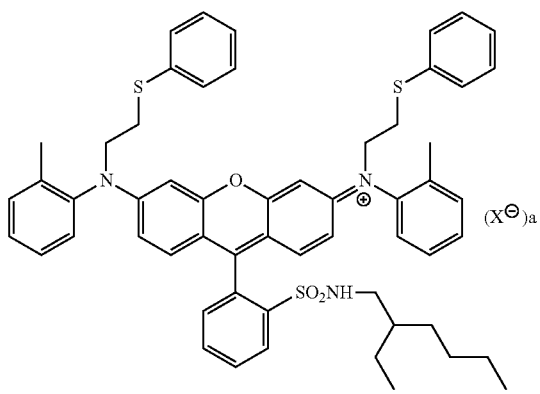
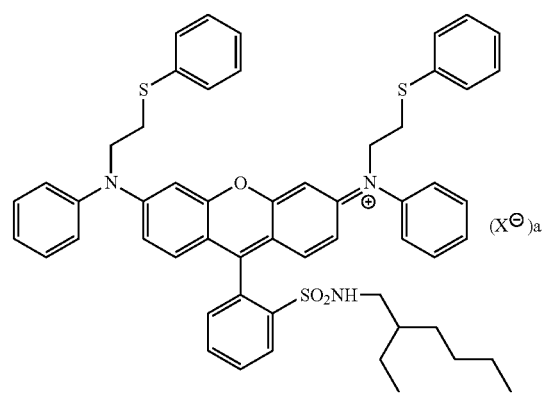
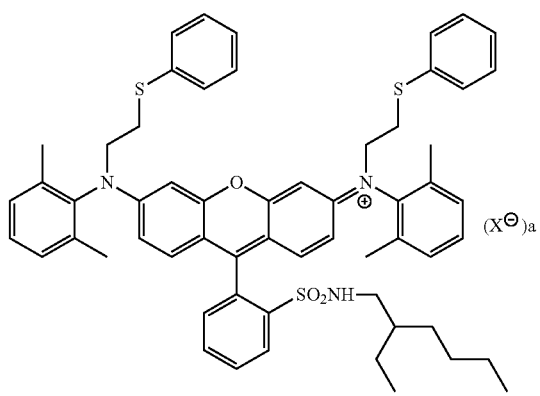

51
-continued
52
-continued
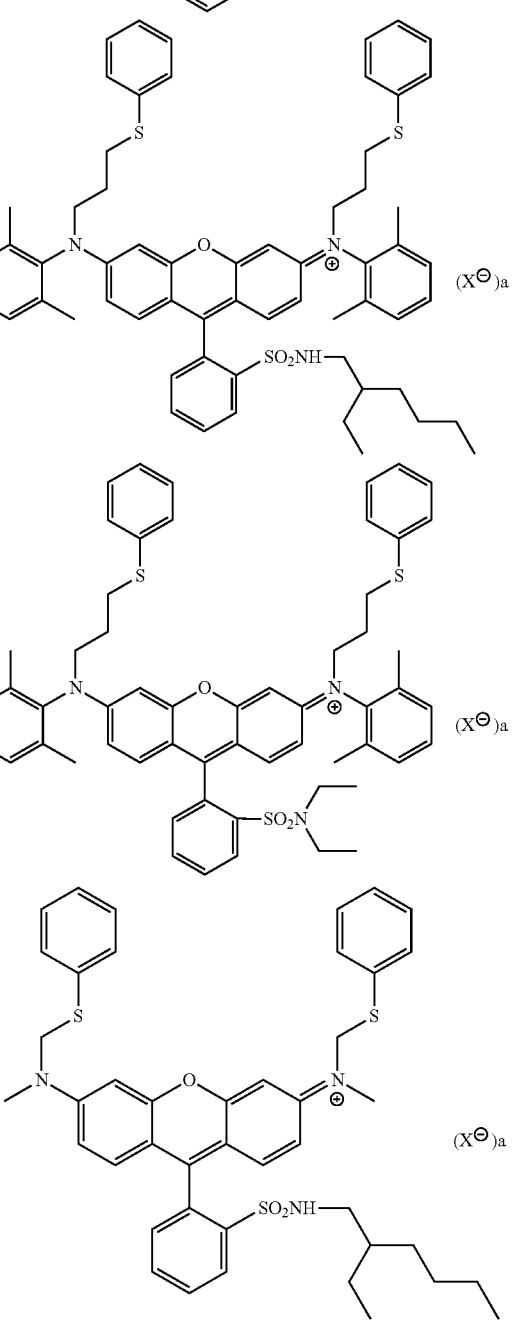

53
-continued
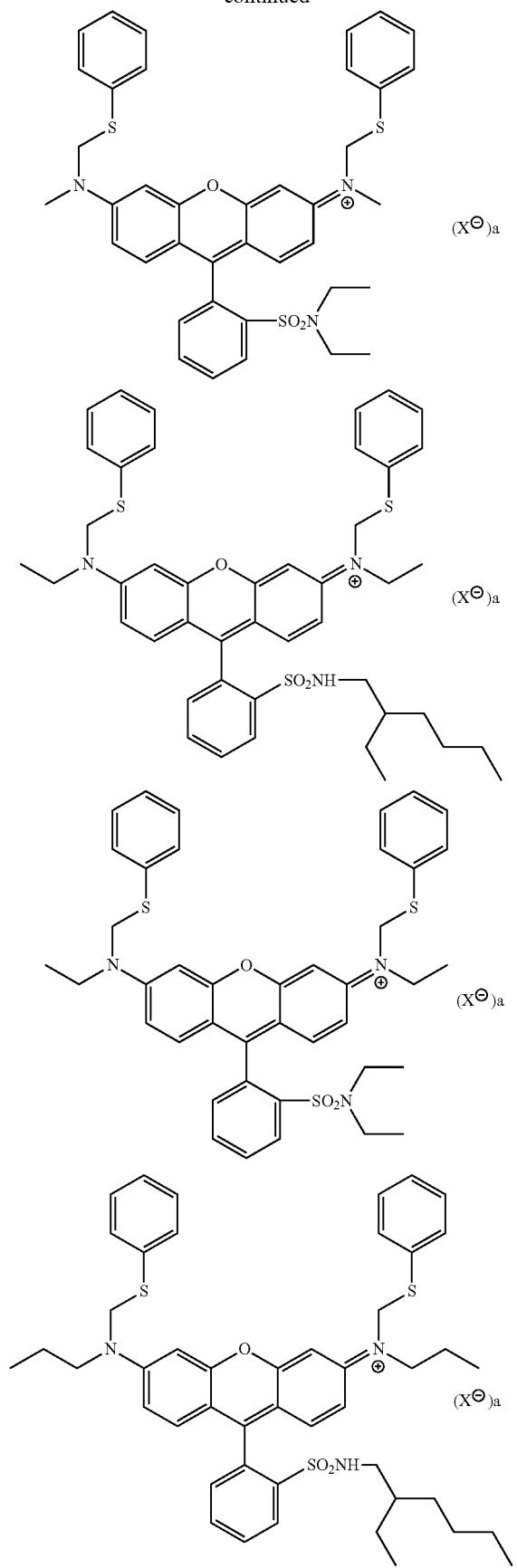
54
-continued
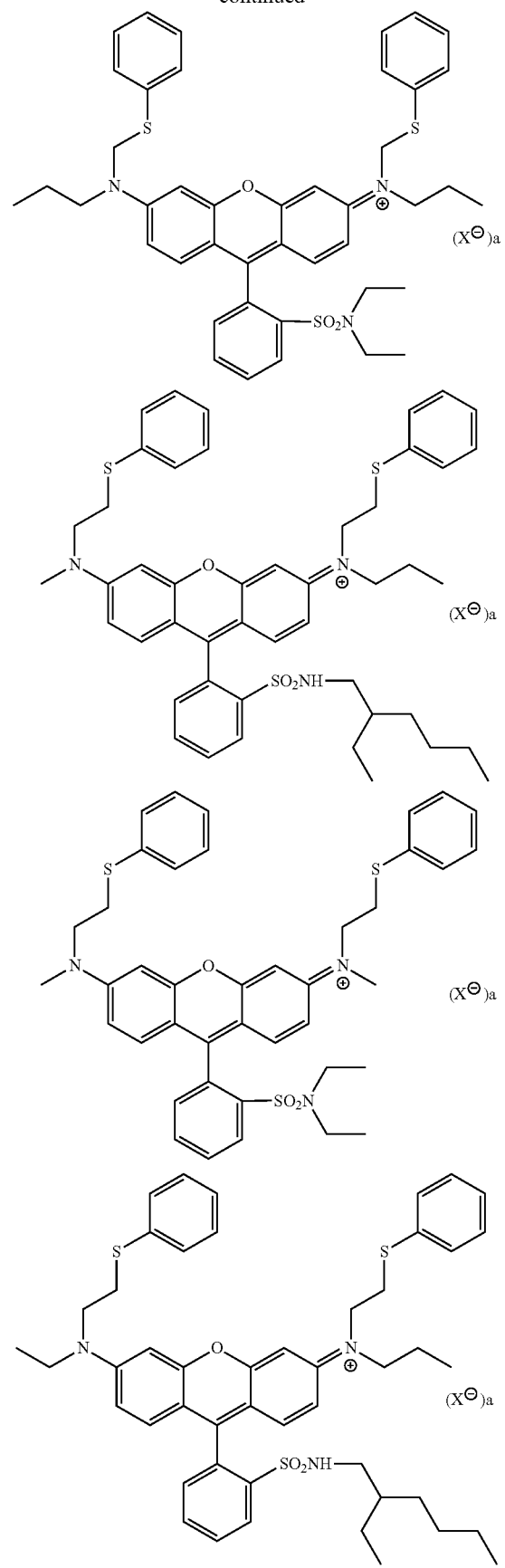

55
-continued
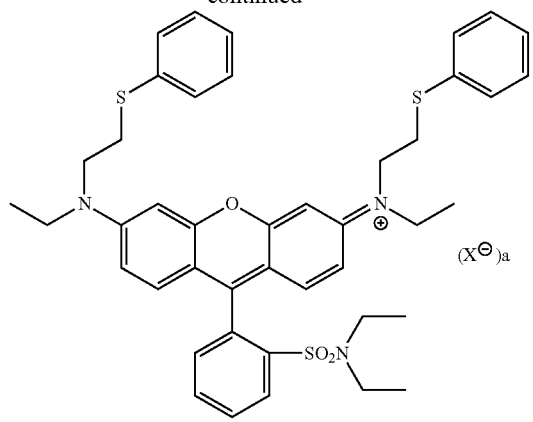
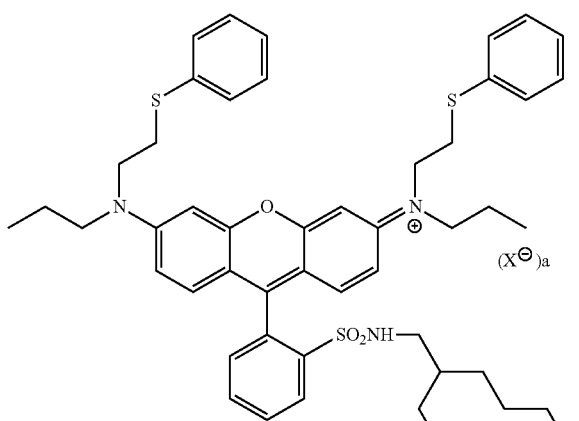
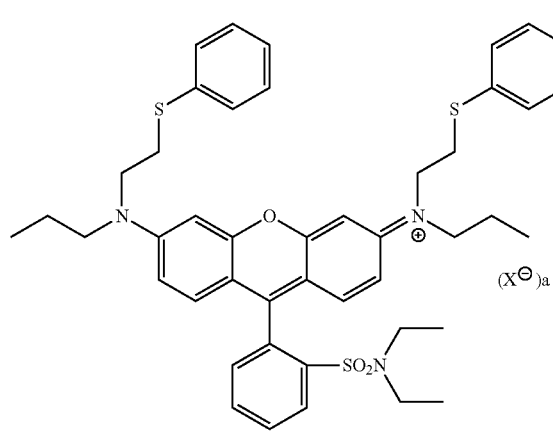
56
-continued
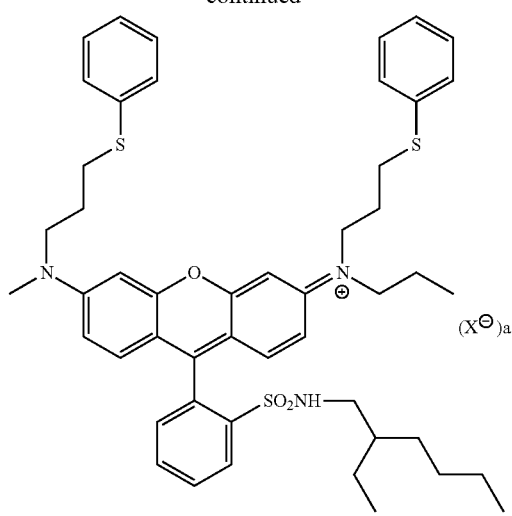
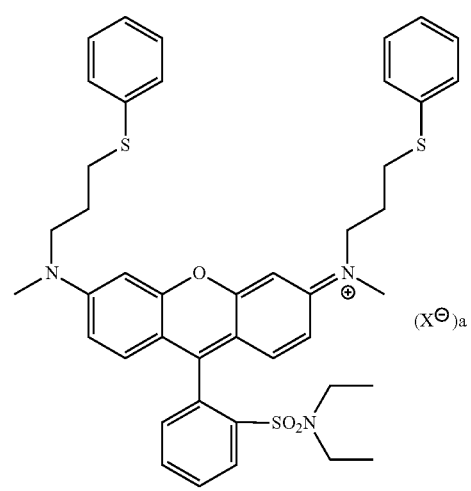
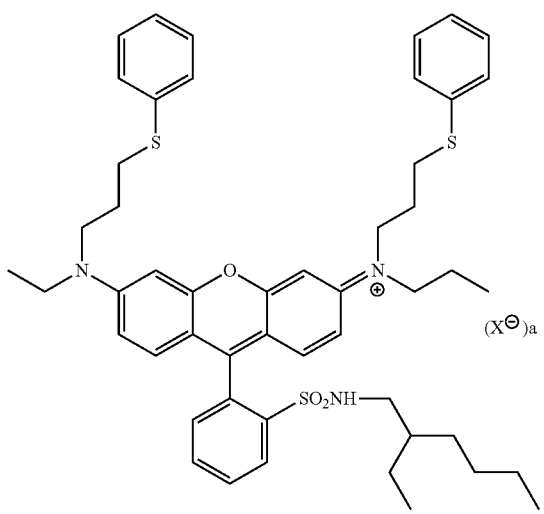

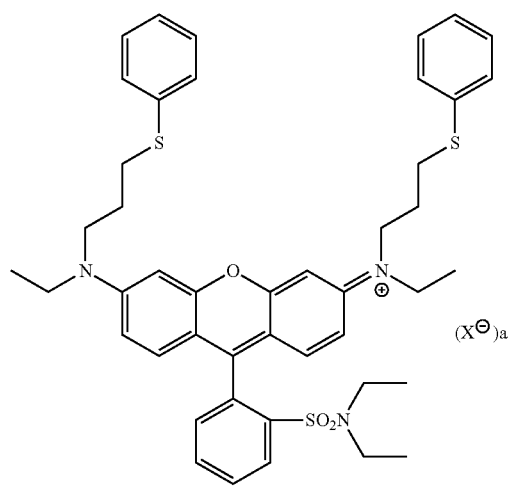

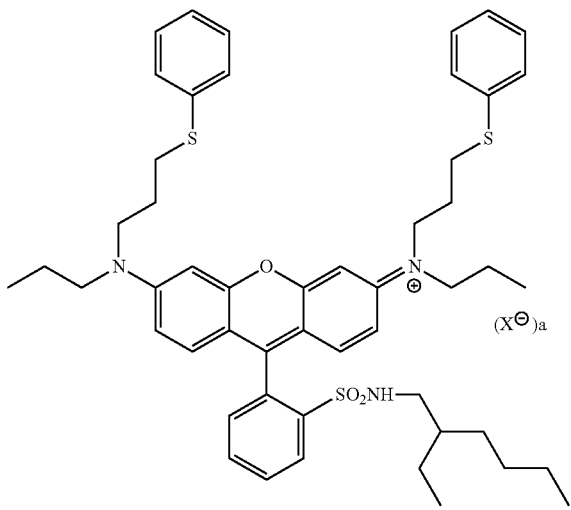

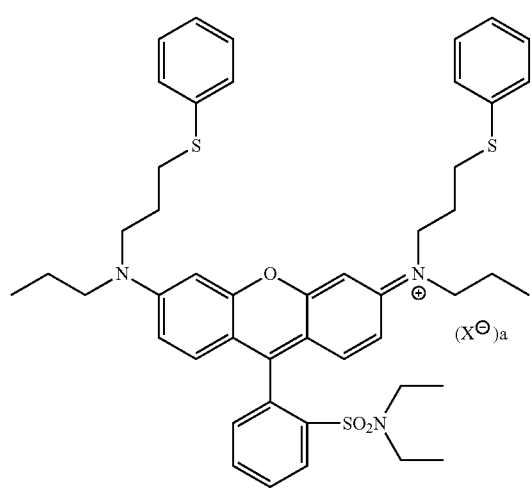

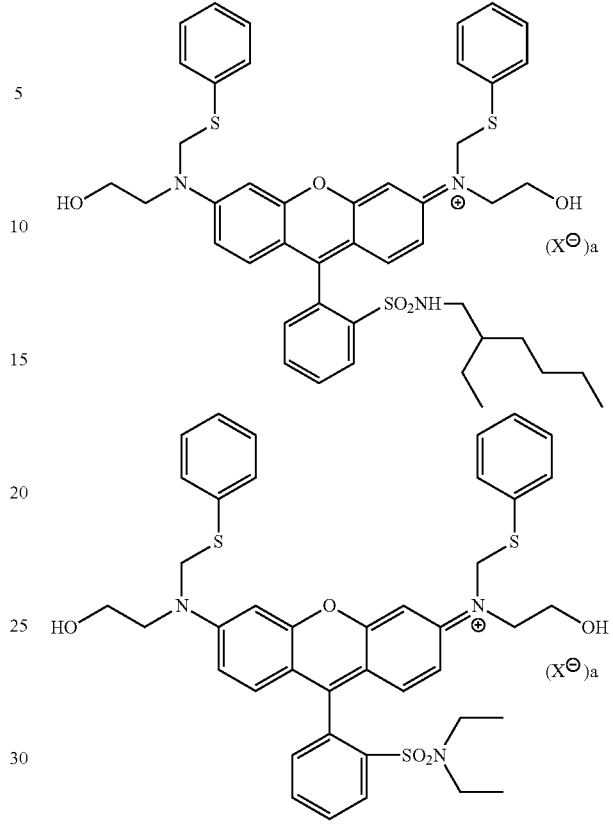

In the chemical formulae, a is an integer of 0 or 1, and X has the same definition as above.

Another embodiment of the present specification may provide a colorant composition comprising the compound.

The colorant composition may further comprise at least one type of dyes and pigments in addition to the compound of Chemical Formula 1. For example, the colorant composition may comprise only the compound of Chemical Formula 1, but may also comprise the compound of Chemical Formula 1 and one or more types of dyes, comprise the compound of Chemical Formula 1 and one or more types of pigments, or comprise the compound of Chemical Formula 1, one or more types of dyes and one or more types of pigments.

As the dye and the pigment, one or more types may be selected from the group consisting of metal-complex-based compounds; azo-based compounds; metal azo-based compounds; quinophthalone-based compounds; isoindoline-based compounds; methine-based compounds; phthalocyanine-based compounds; metal phthalocyanine-based compounds; porphyrin-based compounds; metal porphyrin-based compounds; tetra aza porphyrin-based compounds; metal tetra aza porphyrin-based compounds; cyanine-based compounds; xanthene-based compounds; metal dipyrromethane-based compounds; boron dipyrromethane-based compounds; anthraquinone-based compounds; diketopyrrolopyrrole-based compounds; triarylmethane-based compounds; and perylene-based compounds.

One embodiment of the present specification may provide a resin composition comprising the colorant composition.

According to one embodiment of the present specification, the resin composition may further comprise the compound represented by Chemical Formula 1; a binder resin; a multifunctional monomer; a photoinitiator; and a solvent.

The binder resin is not particularly limited as long as it is capable of exhibiting properties such as strength and developability of a film prepared with the resin composition.

As the binder resin, a copolymerized resin of a multifunctional monomer providing mechanical strength and a monomer providing alkali solubility may be used, and the binder resin may further include binders generally used in the art.

The multifunctional monomer providing mechanical strength of the film may be any one or more of unsaturated carboxylic acid esters; aromatic vinyls; unsaturated ethers; unsaturated imides; and acid anhydrides.

Specific examples of the unsaturated carboxylic acid esters may be selected from the group consisting of benzyl (meth)acrylate, methyl (meth)acrylate, ethyl (meth)acrylate, butyl (meth)acrylate, dimethylaminoethyl (meth)acrylate, isobutyl (meth)acrylate, t-butyl (meth)acrylate, cyclohexyl (meth)acrylate, isobornyl (meth)acrylate, ethylhexyl (meth) acrylate, 2-phenoxyethyl (meth)acrylate, tetrahydrofurfuryl (meth)acrylate, hydroxyethyl (meth)acrylate, 2-hydroxypropyl (meth)acrylate, 2-hydroxy-3-chloropropyl (meth)acrylate, 4-hydroxybutyl (meth)acrylate, acyloctyloxy-2-hydroxypropyl (meth)acrylate, glycerol (meth)acrylate, 2-methoxyethyl (meth)acrylate, 3-methoxybutyl (meth) acrylate, ethoxydiethylene glycol (meth)acrylate, methoxytriethylene glycol (meth)acrylate, methoxytripropylene glycol (meth)acrylate, polyethylene glycol) methyl ether (meth)acrylate, phenoxydiethylene glycol (meth)acrylate, p-nonylphenoxy polyethylene glycol (meth)acrylate, p-nonylphenoxy polypropylene glycol (meth)acrylate, glycidyl (meth)acrylate, tetrafluoropropyl (meth)acrylate, 1,1,1,3,3,3-hexafluoroisopropyl (meth)acrylate, octafluoropentyl (meth)acrylate, heptadecafluorodecyl (meth)acrylate, tribromophenyl (meth)acrylate, methyl α-hydroxymethyl acrylate, ethyl α-hydroxymethyl acrylate, propyl α-hydroxymethyl acrylate and butyl α-hydroxymethyl acrylate, but are not limited thereto.

Specific examples of the aromatic vinyl monomers may be selected from the group consisting of styrene, α-methylstyrene, (o,m,p)-vinyl toluene, (o,m,p)-methoxystyrene and (o,m,p)-chlorostyrene, but are not limited thereto.

Specific examples of the unsaturated ethers may be selected from the group consisting of vinyl methyl ether, vinyl ethyl ether and allyl glycidyl ether, but are not limited thereto.

Specific examples of the unsaturated imides may be selected from the group consisting of N-phenylmaleimide, N-(4-chlorophenyl)maleimide, N-(4-hydroxyphenyl)maleimide and N-cyclohexylmaleimide, but are not limited thereto.

Examples of the acid anhydride may include maleic anhydride, methyl maleic anhydride, tetrahydrophthalic anhydride and the like, but are not limited thereto.

The monomer providing alkali solubility is not particularly limited as long as it includes an acid group, and using one or more types selected from the group consisting of, for example, (meth)acrylic acid, crotonic acid, itaconic acid, maleic acid, fumaric acid, monomethyl maleic acid, 5-norbornene-2-carboxylic acid, mono-2-((meth)acryloyloxy) ethyl phthalate, mono-2-((meth)acryloyloxy)ethyl succinate and ω-carboxypolycarprolactone mono(meth)acrylate is preferred, however, the monomer is not limited thereto.

According to one embodiment of the present specification, the binder resin may have an acid value of 50 KOH mg/g to 130 KOH mg/g and a weight average molecular weight of 1,000 to 50,000.

The multifunctional monomer is a monomer performing a role of forming a photoresist phase by light, and specifically, may be one type or a mixture of two or more types selected from the group consisting of propylene glycol methacrylate, dipentaerythritol hexaacrylate, dipentaerythritol acrylate, neopentyl glycol diacrylate, 6-hexanediol diacrylate, 1,6-hexanediol acrylate, tetraethylene glycol methacrylate, bisphenoxy ethyl alcohol diacrylate, trishydroxyethyl isocyanurate trimethacrylate, trimethylpropane trimethacrylate, diphenylpentaerythritol hexaacrylate, pentaerythritol trimethacrylate, pentaerythritol tetramethacrylate and dipentaerythritol hexamethacrylate.

The photoinitiator is not particularly limited as long as it is an initiator generating radicals by light and prompting cross-linkage, and examples thereof may include one or more types selected from the group consisting of acetophenone-based compounds, biimidazole-based compounds, triazine-based compounds and oxime-based compounds.

Examples of the acetophenone-based compound may include 2-hydroxy-2-methyl-1-phenylpropan-1-one, 1-(4-isopropylphenyl)-2-hydroxy-2-methylpropan-1-one, 4-(2-hydroxyethoxy)-phenyl-(2-hydroxy-2-propyl)ketone, 1-hydroxycyclohexylphenyl ketone, benzoin methyl ether, benzoin ethyl ether, benzoin isobutyl ether, benzoin butyl ether, 2,2-dimethoxy-2-phenylacetophenone, 2-methyl-(4-methylthio)phenyl-2-morpholino-1-propan-1-one, 2-benzyl-2-dimethylamino-1-(4-morpholinophenyl)-butan-1-one, 2-(4-bromo-benzyl-2-dimethylamino-1-(4-morpholinophenyl)-butan-1-one, 2-methyl-1-[4-(methylthio)phenyl]-2-morpholinopropan-1-one or the like, but are not limited thereto.

Examples of the biimidazole-based compound may include 2,2-bis(2-chlorophenyl)-4,4',5,5'-tetraphenyl biimidazole, 2,2'-bis(o-chlorophenyl)-4,4',5,5'-tetrakis(3,4,5-trimethoxyphenyl)-1,2'-biimidazole, 2,2'-bis(2,3-dichlorophenyl)-4,4',5,5'-tetraphenyl biimidazole, 2,2'-bis(o-chlorophenyl)-4,4,5,5'-tetraphenyl-1,2'-biimidazole and the like, but are not limited thereto.

Examples of the triazine-based compound may include 3-{4-[2,4-bis(trichloromethyl)-s-triazin-6-yl]phenylthio} propionic acid, 1,1,1,3,3,3-hexafluoroisopropyl-3-{4-[2,4-bis(trichloromethyl)-s-triazin-6-yl]phenylthio}propionate, ethyl-2-{4-[2,4-bis(trichloromethyl)-s-triazin-6-yl]phenylthio}acetate, 2-epoxyethyl-2-{4-[2,4-bis(trichloromethyl)-s-triazin-6-yl]phenylthio}acetate, cyclohexyl-2-{4-[2,4-bis(trichloromethyl)-s-triazin-6-yl]phenylthio}acetate, benzyl-2-{4-[2,4-bis(trichloromethyl)-s-triazin-6-yl]phenylthio}acetate, 3-{chloro-4-[2,4-bis(trichloromethyl)-s-triazin-6-yl]phenylthio}propionic acid, 3-{4-[2,4-bis(trichloromethyl)-s-triazin-6-yl]phenylthio}propionamide, 2,4-bis(trichloromethyl)-6-p-methoxystyryl-s-triazine, 2,4-bis(trichloromethyl)-6-(1-p-dimethylaminophenyl)-1,3,-butadienyl-s-triazine, 2-trichloromethyl-4-amino-6-p-methoxystyryl-s-triazine and the like, but are not limited thereto.

Examples of the oxime-based compound may include 1,2-octadione-1-(4-phenylthio)phenyl-2-(o-benzoyloxime) (Ciba-Geigy, CGI 124), ethanone-1-(9-ethyl)-6-(2-methylbenzoyl-3-yl)-1-(o-acetyloxime) (CGI 242), N-1919 (Adeka Corporation) and the like, but are not limited thereto.

The solvent may be one or more types selected from the group consisting of acetone, methyl ethyl ketone, methyl isobutyl ketone, methyl cellosolve, ethyl cellosolve, tetrahydrofuran, 1,4-dioxane, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methyl ethyl ether, chloroform, methylene chloride, 1,2-dichloroethane, 1,1,1-trichloroethane, 1,1,2-trichloroethane, 1,1,2-trichloroethene, hexane, heptane, octane, cyclohexane, benzene, toluene, xylene, methanol, ethanol, isopropanol, propanol, butanol, t-butanol, 2-ethoxypropanol, 2-methoxypropanol, 3-methoxybutanol, cyclohexanone, cyclopentanone, propylene glycol methyl ether acetate, propylene glycol ethyl ether acetate, 3-methoxybutyl acetate, ethyl 3-ethoxypropionate, ethyl cellosolve acetate, methyl cellosolve acetate, butyl acetate, propylene glycol monomethyl ether and dipropylene glycol monomethyl ether, but is not limited thereto.

According to one embodiment of the present specification, a content of the compound represented by Chemical Formula 1 is from 5% by weight to 60% by weight, a content of the binder resin is from 1% by weight to 60% by weight, a content of the photoinitiator is from 0.1% by weight to 20% by weight, and a content of the multifunctional monomer is from 0.1% by weight to 50% by weight, based on a total weight of the solid content in the resin composition.

The total weight of the solid content means a sum of total weights of the components excluding the solvent in the resin composition. A standard of % by weight based on the solid content and the solid content of each component may be measured using general analysis means used in the art such as liquid chromatography or gas chromatography.

According to one embodiment of the present specification, the resin composition may further comprise an antioxidant.

According to one embodiment of the present specification, a content of the antioxidant may be from 0.1% by weight to 20% by weight based on a total weight of the solid content in the resin composition.

According to one embodiment of the present specification, the resin composition may further comprise one, two or more additives selected from the group consisting of a light crosslinking sensitizer, a curing accelerator, an adhesion accelerator, a surfactant, a thermal polymerization inhibitor, an ultraviolet absorbent, a dispersant and a leveling agent.

According to one embodiment of the present specification, a content of the additives is from 0.1% by weight to 20% by weight based on a total weight of the solid content in the resin composition.

As the light crosslinking sensitizer, one or more types selected from the group consisting of benzophenone-based compounds such as benzophenone, 4,4-bis(dimethylamino) benzophenone, 4,4-bis(diethylamino)benzophenone, 2,4,6-trimethylaminobenzophenone, methyl-o-benzoylbenzoate, 3,3-dimethyl-4-methoxybenzophenone and 3,3,4,4-tetra(t-butylperoxycarbonyl)benzophenone; fluorenone-based compounds such as 9-fluorenone, 2-chloro-9-fluorenone and 2-methyl-9-fluorenone; thioxanthone-based compounds such as thioxanthone, 2,4-diethylthioxanthone, 2-chlorothioxanthone, 1-chloro-4-propyloxythioxanthone, isopropylthioxanthone and diisopropylthioxanthone; xanthone-based compounds such as xanthone and 2-methylxanthone; anthraquinone-based compounds such as anthraquinone, 2-methylanthraquinone, 2-ethylanthraquinone, t-butylanthraquinone and 2,6-dichloro-9,10-anthraquinone; acridine-based compounds such as 9-phenylacridine, 1,7-bis(9-acridinyl)heptane, 1,5-bis(9-acridinylpentane) and 1,3-bis(9-acridinyl) propane; dicarbonyl compounds such as benzyl, 1,7,7-trimethyl-bicyclo[2,2,1]heptane-2,3-dione and 9,10-phenanthrenequinone; phosphine oxide-based compounds such as 2,4,6-trimethylbenzoyl diphenylphosphine oxide and bis (2,6-dimethoxybenzoyl)-2,4,4-trimethylpentyl phosphine oxide; benzoate-based compounds such as methyl-4-(dimethylamino)benzoate, ethyl-4-(dimethylamino)benzoate and 2-n-butoxyethyl-4-(dimethylamino)benzoate; amino synergists such as 2,5-bis(4-diethylaminobenzal)cyclopentanone, 2,6-bis(4-diethylaminobenzal)cyclohexanone and 2,6-bis(4-diethylaminobenzal)-4-methyl-cyclopentanone; coumarin-based compounds such as 3,3-carbonylvinyl-7-(diethylamino)coumarin, 3-(2-benzothiazolyl)-7-(diethylamino)coumarin, 3-benzoyl-7-(diethylamino)coumarin, 3-benzoyl-7-methoxy-coumarin and 10,10-carbonylbis[1,1,7,7-tetramethyl-2,3,6,7-tetrahydro-1H,5H,11H—C1]-benzopyrano[6,7,8-ij]-quinolizin-11-one; chalcone compounds such as 4-diethylamino chalcone and 4-azidebenzalacetophenone; 2-benzoylmethylene and 3-methyl-b-naphthothiazoline may be used.

The curing accelerator is used for enhancing curing and mechanical strength, and specifically, one or more types selected from the group consisting of 2-mercaptobenzimidazole, 2-mercaptobenzothiazole, 2-mercaptobenzoxazole, 2,5-dimercapto-1,3,4-thiadiazole, 2-mercapto-4,6-dimethylaminopyridine, pentaerythritol-tetrakis(3-mercaptopropionate), pentaerythritol-tris(3-mercaptopropionate), pentaerythritol-tetrakis(2-mercaptoacetate), pentaerythritol-tris (2-mercaptoacetate), trimethylolpropane-tris(2-mercaptoacetate) and trimethylolpropane-tris(3-mercaptopropionate) may be used.

As the adhesion accelerator used in the present specification, one or more types of methacryloyl silane coupling agents such as methacryloyloxy propyltrimethoxysilane, methacryloyloxy propyldimethoxysilane, methacryloyloxy propyltriethoxysilane and methacryloyloxy propyldimethoxysilane may be selected and used, and as alkyl trimethoxysilane, one or more types of octyltrimethoxysilane, dodecyltrimethoxysilane, octadecyltrimethoxysilane and the like may be selected and used.

The surfactant is a silicone-based surfactant or a fluorine-based surfactant, and specific examples of the silicone-based surfactant may include BYK-077, BYK-085, BYK-300, BYK-301, BYK-302, BYK-306, BYK-307, BYK-310, BYK-320, BYK-322, BYK-323, BYK-325, BYK-330, BYK-331, BYK-333, BYK-335, BYK-341v344, BYK-345v346, BYK-348, BYK-354, BYK-355, BYK-356, BYK-358, BYK-361, BYK-370, BYK-371, BYK-375, BYK-380, BYK-390 and the like of BYK-Chemie, and examples of the fluorine-based surfactant may include F-114, F-177, F-410, F-411, F-450, F-493, F-494, F-443, F-444, F-445, F-446, F-470, F-471, F-472SF, F-474, F-475, F-477, F-478, F-479, F-480SF, F-482, F-483, F-484, F-486, F-487, F-172D, MCF-350SF, TF-1025SF, TF-1117SF, TF-1026SF, TF-1128, TF-1127, TF-1129, TF-1126, TF-1130, TF-1116SF, TF-1131, TF1132, TF1027SF, TF-1441, TF-1442 and the like of DaiNippon Ink & Chemicals (DIC), however, the surfactant is not limited thereto.

The antioxidant may include one or more types selected from the group consisting of hindered phenol antioxidants, amine-based antioxidants, thio-based antioxidants and phosphine-based antioxidants, but is not limited thereto.

Specific examples of the antioxidant may include phosphoric acid-based thermal stabilizers such as phosphoric acid, trimethylphosphate or triethylphosphate; hindered phenol-based primary antioxidants such as 2,6-di-t-butyl-p-cresole, octadecyl-3-(4-hydroxy-3,5-di-t-butylphenyl)propionate, tetrabis[methylene-3-(3,5-di-t-butyl-4-hydroxyphenyl)propionate]methane, 1,3,5-trimethyl-2,4,6-tris(3,5-di-t-butyl-4-hydroxybenzyl)benzene, 3,5-di-t-butyl-4-hydroxybenzylphosphite diethyl ester, 2,2-thiobis(4-methyl-6-t-butylphenol), 2,6-g,t-butylphenol, 4,4'-butylidene-bis(3-methyl-6-t-butylphenol), 4,4'-thiobis(3-methyl-6-t-butylphenol) or bis[3,3-bis-(4'-hydroxy-3'-tert-butylphenyl)butanoic acid]glycol ester; amine-based secondary antioxidants such as phenyl-α-naphthylamine, phenyl-β-naphthylamine, N,N'-diphenyl-p-phenylenediamine or N,N'-di-β-naphthyl-p-phenylenediamine; thio-based secondary antioxidants such as dilauryl disulfide, dilauryl thiopropionate, distearyl thiopropionate, mercaptobenzothiazole or tetramethylthiuram disulfide tetrabis[methylene-3-(laurylthio)propionate]methane; or phosphite-based secondary antioxidants such as triphenyl phosphite, tris(nonylphenyl) phosphite, triisodecyl phosphite, bis(2,4-dibutylphenyl) pentaerythritol diphosphate or (1,1'-biphenyl)-4,4'-diyl-bisphosphonous acid tetrakis[2,4-bis(1,1-dimethylethyl) phenyl]ester.

As the ultraviolet absorbent, 2-(3-t-butyl-5-methyl-2-hydroxyphenyl)-5-chloro-benzotriazole, alkoxy benzophenone and the like may be used, however, those generally used in the art may all be used without being limited thereto.

The thermal polymerization inhibitor may include one or more types selected from the group consisting of p-anisole, hydroquinone, pyrocatechol, t-butyl catechol, N-nitrosophenylhydroxyamine ammonium salts, N-nitrosophenylhydroxyamine aluminum salts, p-methoxyphenol, di-t-butyl-p-cresole, pyrogallol, benzoquinone, 4,4-thiobis(3-methyl-6-t-butylphenol), 2,2-methylenebis(4-methyl-6-t-butylphenol), 2-mercaptoimidazole and phenothiazine, but is not limited thereto, and may include those generally known in the art.

The dispersant may be used in a manner of being added into a pigment in a form of surface treating the pigment in advance, or being added outside a pigment. As the dispersant, compound-type, non-ionic, anionic or cationic dispersants may be used, and fluorine-based, ester-based, cation-based, anion-based, non-ion-based, amphoteric surfactants and the like may be included. These may be used either alone or as a combination of two or more types.

Specifically, the dispersant may be one or more types selected from the group consisting of polyalkylene glycol and esters thereof, polyoxyalkylene polyalcohol, ester alkylene oxide adducts, alcohol alkylene oxide adducts, sulfonic acid ester, sulfonic acid salts, carboxylic acid ester, carboxylic acid salts, alkylamide alkylene oxide adducts and alkylamine, but is not limited thereto.

The leveling agent may be polymeric or non-polymeric. Specific examples of the polymeric leveling agent may include polyethyleneimine, polyamideamine, and reaction products of amine and epoxide, and specific examples of the non-polymeric leveling agent may include non-polymer sulfur-containing and non-polymer nitrogen-containing compounds, but are not limited thereto, and those generally used in the art may all be used.

One embodiment of the present specification provides a photosensitive material prepared using the resin composition.

More specifically, a photosensitive material in a thin film or a pattern form is formed by coating the resin composition of the present specification on a substrate using a proper method.

The coating method is not particularly limited, and a spray method, a roll coating method, a spin coating method and the like may be used, and generally, a spin coating method is widely used. In addition, after forming a coated film, some of the residual solvent may be removed under vacuum in some cases.

Examples of a light source for curing the resin composition according to the present specification include mercury vapor arc, carbon arc, Xe arc and the like releasing light in a wavelength of 250 nm to 450 nm, but are not limited thereto.

The resin composition according to the present specification may be used in a pigment dispersion-type photosensitive material for manufacturing a thin film transistor liquid crystal display (TFT LCD) color filter, a photosensitive material for forming a black matrix of a thin film transistor liquid crystal display (TFT LCD) or organic light emitting diode, a photosensitive material for forming an overcoat layer, a column spacer photosensitive material, a photocurable paint, a photocurable ink, a photocurable adhesive, a printing plate, a photosensitive material for a print wiring board, a photosensitive material for a plasma display panel (PDP), and the like, and the use is not particularly limited.

One embodiment of the present specification provides a color filter comprising the photosensitive material.

The color filter may be manufactured using the resin composition comprising the compound represented by Chemical Formula 1. The color filter may be formed by forming a coating film by coating the resin composition on a substrate, and exposing, developing and curing the coating film.

The resin composition according to one embodiment of the present specification has excellent heat resistance and experiences small color changes with heat treatment, and therefore, a color filter having high color gamut, and high luminance and contrast ratio may be provided even with a curing process in the manufacture of the color filter.

The substrate may be a glass plate, a silicon wafer, and a plate made of a plastic substrate such as polyethersulfone (PES) and polycarbonate (PC), and the type is not particularly limited.

The color filter may comprise a red pattern, a green pattern, a blue pattern and a black matrix.

According to another embodiment, the color filter may further comprise an overcoat layer.

With intent to enhance contrast, a grid black pattern referred to as a black matrix may be disposed between color pixels of the color filter. Chromium may be used as a material of the black matrix. In this case, a method of depositing chromium on a whole glass substrate and forming a pattern by etching treatment may be used. However, when considering high process costs, high reflectance of chromium, environmental contamination caused by chromium waste liquid, a resin black matrix using a pigment dispersion method capable of micromachining may be used.

The black matrix according to one embodiment of the present specification may use black pigments or black dyes as a colorant. For example, carbon black may be used alone, or carbon black and a coloring pigment may be mixed and used. Herein, since a coloring pigment lacking a lightproof property is mixed thereto, there is an advantage in that film strength or adhesion to a substrate does not decline even when the amount of the colorant relatively increases.

One embodiment of the present specification provides a display device comprising the color filter.

The display device may be any one of a plasma display panel (PDP), a light emitting diode (LED), an organic light emitting diode (OLED), a liquid crystal display (LCD), a thin film transistor-liquid crystal display (LCD-TFT) and a cathode ray tube (CRT).

Hereinafter, the present specification will be described in detail with reference to examples. However, the examples according to the present specification may be modified to various other forms, and the scope of the present specification is not to be construed as being limited to the examples described below. Examples of the present specification are provided in order to more fully describe the present specification to those having average knowledge in the art.

EXAMPLE

Synthesis Example of Colorant Compound

Synthesis Example 1: Synthesis of Compound 1

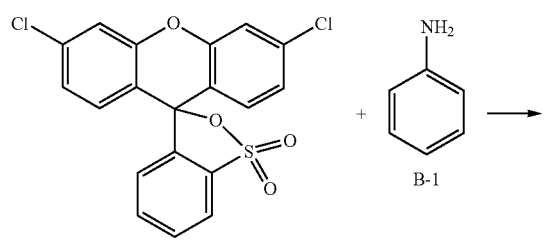

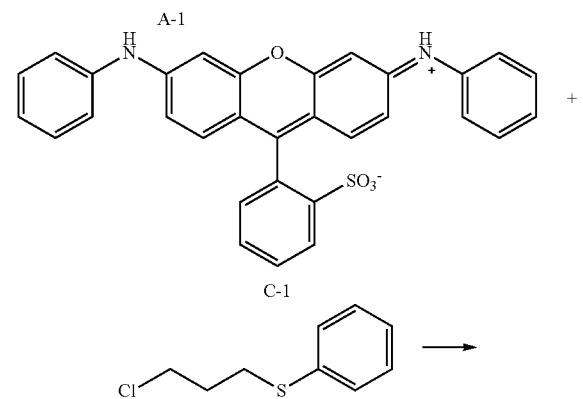

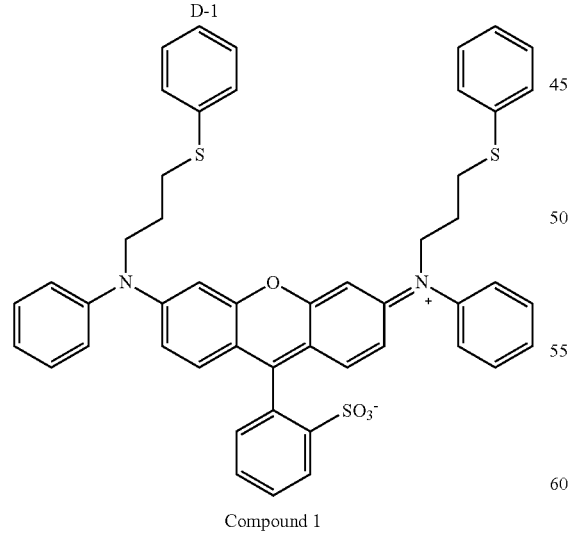

Compound 1

In a 1-neck 100 ml round bottom flask (RBF), A-1 (1 g, 2.468 mmol), methanol (MeOH) (40 ml), B-1 (2.298 g, 24.68 mmol) and N,N-diisopropylethylamine (DIPEA) (1.279 g, 9.871 mmol) were introduced and stirred. The result was reacted for 24 hours at 60° C., and the reaction solution was cooled to room temperature. The reaction solution was introduced to 1 M hydrochloric acid (HCl) (500 ml), the result was stirred for 30 minutes, and the precipitates were filtered under vacuum and washed. The precipitates were recrystallized with methanol (MeOH) to obtain C-1 (1.0347 g, 1.997 mmol), and the yield was 80%. In a 1-neck 100 ml round bottom flask (RBF), N-methyl-2-pyrrolidone (NMP) (30 ml), D-1 (1.151 g, 6.187 mmol) and sodium iodide (NaI) (0.921 g, 6.1887 mmol) were introduced, and stirred for 30 minutes at 45° C. After that, C-1 (1.0347 g, 1.997 mmol) and $K_2CO_3$ (0.8551 g, 6.187 mmol) were slowly added to the reaction solution, the result was reacted for 4 hours at 95° C., and the reaction solution was cooled to room temperature. The reaction solution was introduced to distilled water (DI-Water) (200 ml), the result was stirred for 30 minutes, and the precipitates were filtered under vacuum and washed.

After that, the precipitates were separated through column chromatography (eluent-methylene chloride:methanol). As a result, Compound 1 (1.114 g, 1.361 mmol) was obtained, and the yield was 68%.

Ionization mode=:APCI+:m/z=819 [M+H]+, Exact Mass: 818

Synthesis Example 2: Synthesis of Compound 2

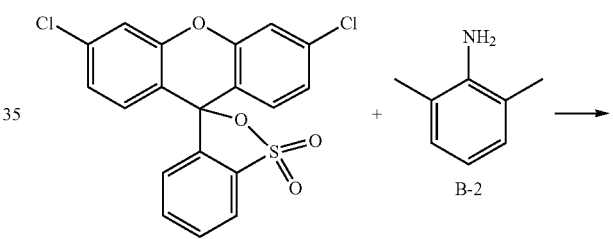

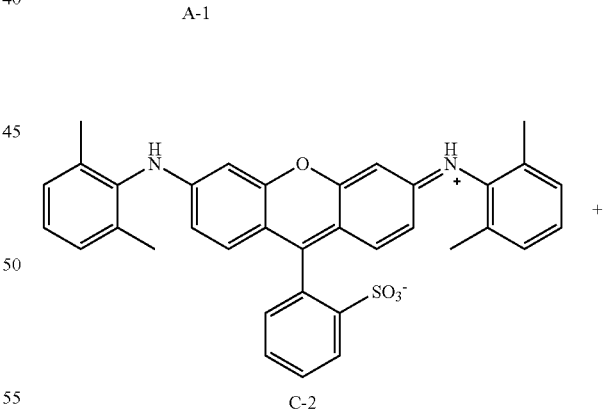

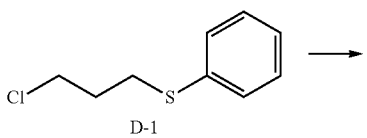

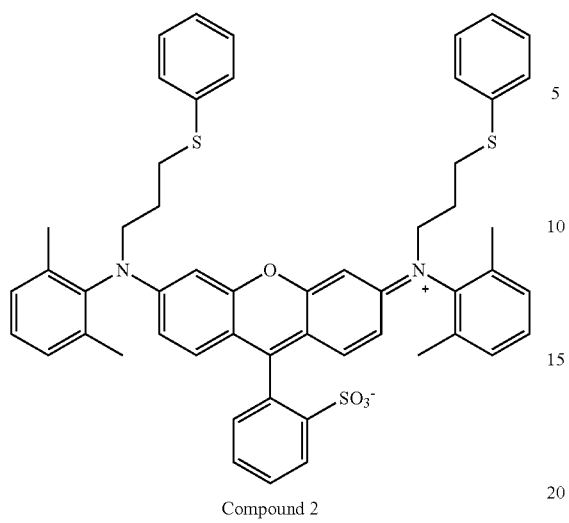

Compound 2

In a 1-neck 200 ml round bottom flask (RBF), A-1 (3 g, 7.426 mmol), NMP (50 ml) and B-2 (4.496 g, 37.129 mmol) were introduced and stirred. The result was reacted for 4 hours at 150° C., and the reaction solution was cooled to room temperature. The reaction solution was introduced to 1 M HCl (500 ml), the result was stirred for 30 minutes, and the precipitates were filtered under vacuum and washed. The precipitates were recrystallized with methanol (MeOH) to obtain C-2 (1.834 g, 3.193 mmol), and the yield was 43%. In a 1-neck 100 ml Round bottom flask (RBF), N-methyl-2-pyrrolidone (NMP) (50 ml), D-1 (3.454 g, 18.566 mmol) and NaI (2.764 g, 18.566 mmol) were introduced, and stirred for 30 minutes at 45° C. After that, C-2 (1.843 g, 3.193 mmol) and potassium carbonate ($K_2CO_3$) (2.566 g, 18.566 mmol) were slowly added to the reaction solution, the result was reacted for 4 hours at 95° C., and the reaction solution was cooled to room temperature. The reaction solution was introduced to DI-Water (500 ml), the result was stirred for 30 minutes, and the precipitates were filtered under vacuum and washed.

After that, the precipitates were separated through column chromatography (eluent-methylene chloride:methanol). As a result, Compound 2 (2.569 g, 2.938 mmol) was obtained, and the yield was 92%.

Ionization mode=:APCI+:m/z=875 [M+H]+, Exact Mass: 874

Synthesis Example 3: Synthesis of Compound 3

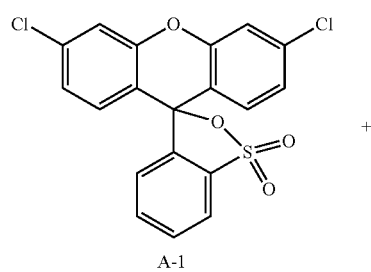

A-1

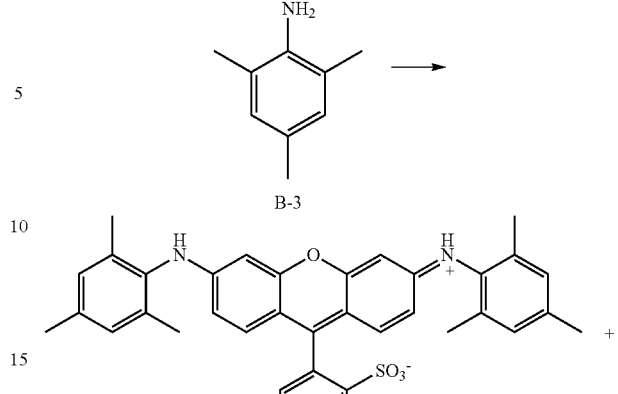

B-3

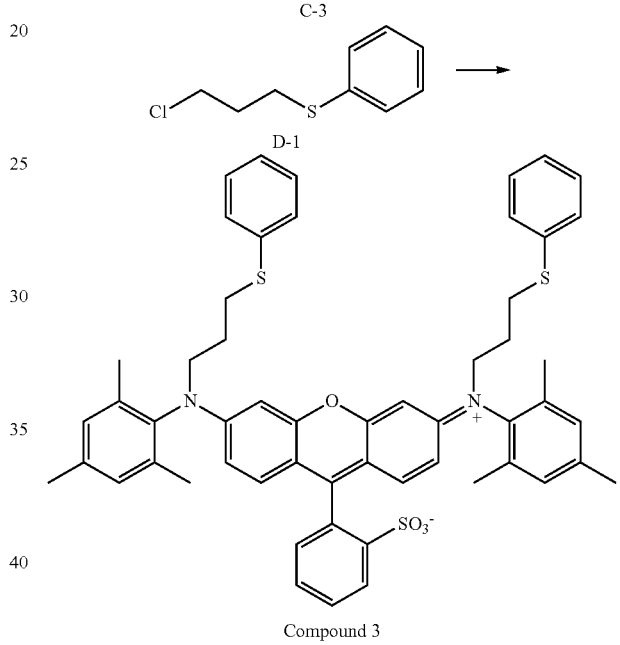

Compound 3

In a 1-neck 200 ml round bottom flask (RBF), A-1 (3 g, 7.426 mmol), N-methyl-2-pyrrolidone (NMP) (50 ml) and B-3 (5.016 g, 37.131 mmol) were introduced and stirred. The result was reacted for 4 hours at 150° C., and the reaction solution was cooled to room temperature. The reaction solution was introduced to 1 M HCl (500 ml), the result was stirred for 30 minutes, and the precipitates were filtered under vacuum and washed. The precipitates were recrystallized with MeOH to obtain C-3 (1.744 g, 2.896 mmol), and the yield was 39%. In a 1-neck 100 ml RBF, NMP (50 ml), D-1 (1.347 g, 7.241 mmol) and NaI (1.078 g, 7.241 mmol) were introduced, and stirred for 30 minutes at 45° C. After that, C-3 (1.744 g, 2.896 mmol) and $K_2CO_3$ (1.001 g, 7.241 mmol) were slowly added to the reaction solution, the result was reacted for 4 hours at 95° C., and the reaction solution was cooled to room temperature. The reaction solution was introduced to DI-Water (500 ml), the result was stirred for 30 minutes, and the precipitates were filtered under vacuum and washed.

After that, the precipitates were separated through column chromatography (eluent-methylene chloride:methanol). As a result, Compound 3 (2.352 g, 2.607 mmol) was obtained, and the yield was 90%.

Ionization mode=:APCI+:m/z=903 [M+H]+, Exact Mass: 902

Synthesis Example 4: Synthesis of Compound 4

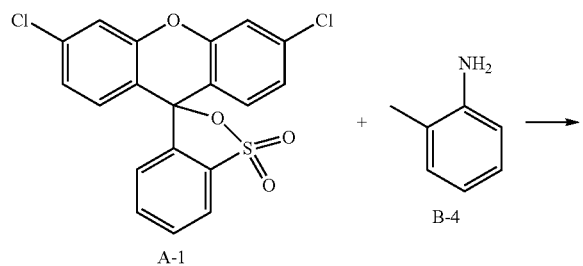

In a 1-neck 200 ml RBF, A-1 (3 g, 7.426 mmol), NMP (50 ml) and B-4 (3.976 g, 37.131 mmol) were introduced and stirred. The result was reacted for 4 hours at 150° C., and the reaction solution was cooled to room temperature. The reaction solution was introduced to 1 M HCl (500 ml), the result was stirred for 30 minutes, and the precipitates were filtered under vacuum and washed. The precipitates were recrystallized with MeOH to obtain C-4 (2.013 g, 3.342 mmol), and the yield was 45%. In a 1-neck 100 ml RBF, NMP (50 ml), D-1 (1.554 g, 8.355 mmol) and NaI (1.244 g, 8.355 mmol) were introduced, and stirred for 30 minutes at 45° C. After that, C-4 (2.013 g, 3.342 mmol) and $K_2CO_3$ (1.1547 g, 8.355 mmol) were slowly added to the reaction solution, the result was reacted for 4 hours at 95° C., and the reaction solution was cooled to room temperature. The reaction solution was introduced to DI-Water (500 ml), the result was stirred for 30 minutes, and the precipitates were filtered under vacuum and washed.

After that, the precipitates were separated through column chromatography (eluent-methylene chloride:methanol). As a result, Compound 4 (2.630 g, 3.108 mmol) was obtained, and the yield was 93%.

Ionization mode=:APCI+:m/z=847 [M+H]+, Exact Mass: 846

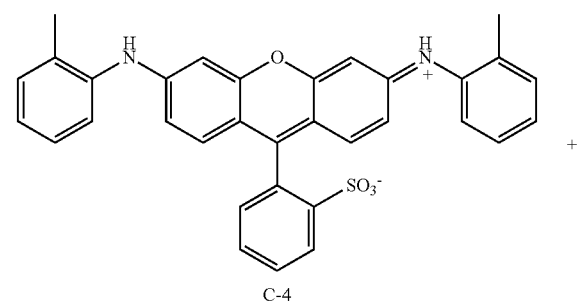

Synthesis Example 5: Synthesis of Compound 5

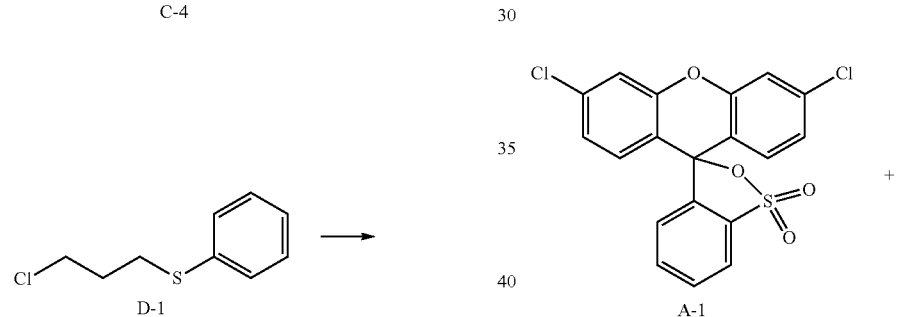

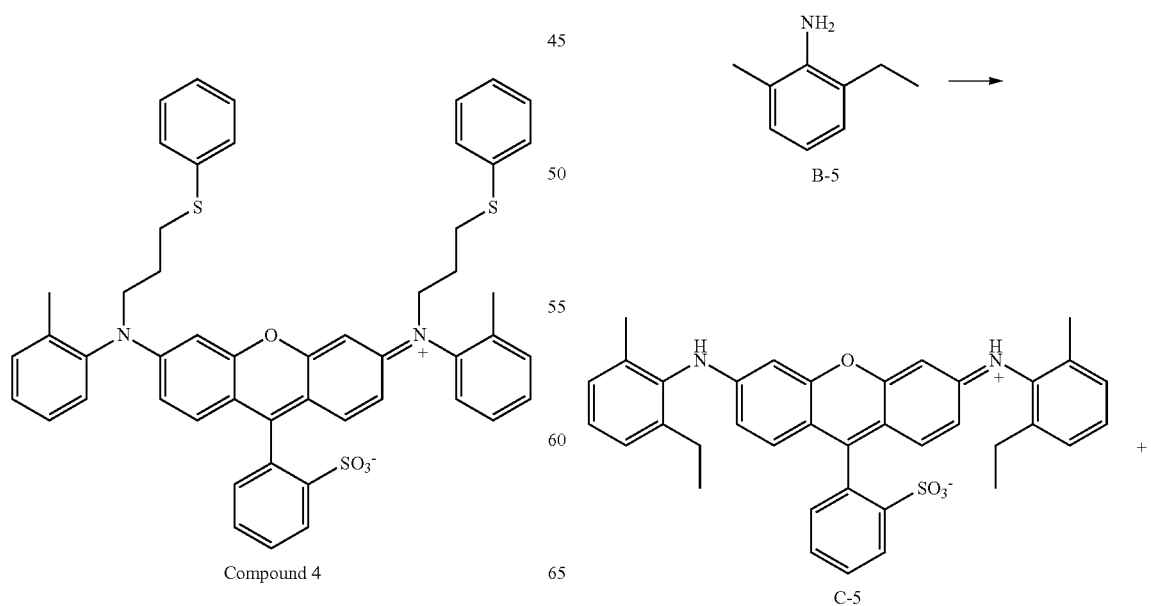

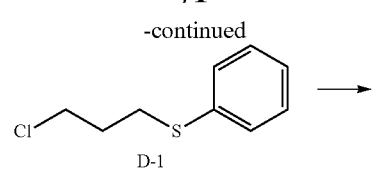

D-1

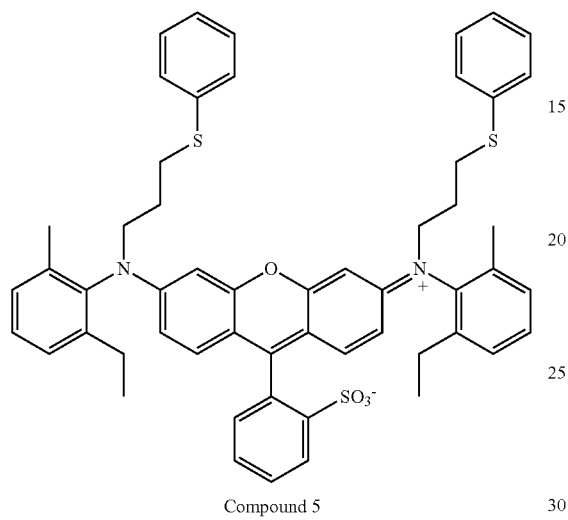

Compound 5

In a 1-neck 200 ml RBF, A-1 (3 g, 7.426 mmol), NMP (50 ml) and B-5 (5.016 g, 37.131 mmol) were introduced and stirred. The result was reacted for 4 hours at 150° C., and the reaction solution was cooled to room temperature. The reaction solution was introduced to 1 M HCl (500 ml), the result was stirred for 30 minutes, and the precipitates were filtered under vacuum and washed. The precipitates were recrystallized with MeOH to obtain C-5 (2.147 g, 3.565 mmol), and the yield was 48%. In a 1-neck 100 ml RBF, NMP (50 ml), D-1 (1.6584 g, 8.912 mmol) and NaI (1.327 g, 8.912 mmol) were introduced, and stirred for 30 minutes at 45° C. After that, C-5 (2.147 g, 3.565 mmol) and K$_2$CO$_3$ (1.232 g, 8.912 mmol) were slowly added to the reaction solution, the result was reacted for 4 hours at 95° C., and the reaction solution was cooled to room temperature. The reaction solution was introduced to DI-Water (500 ml), the result was stirred for 30 minutes, and the precipitates were filtered under vacuum and washed.

After that, the precipitates were separated through column chromatography (eluent-methylene chloride:methanol). As a result, Compound 5 (2.745 g, 3.244 mmol) was obtained, and the yield was 91%.

Ionization mode=:APCI+:m/z=903 [M+H]+, Exact Mass: 902

Synthesis Example 6: Synthesis of Compound 6

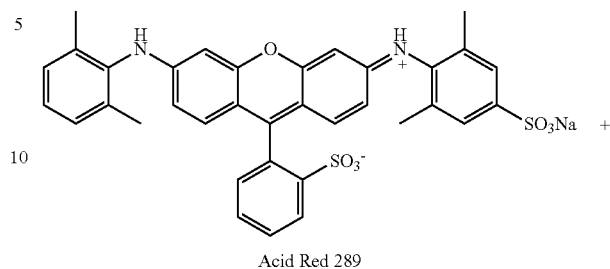

Acid Red 289

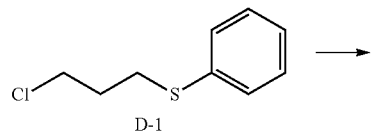

D-1

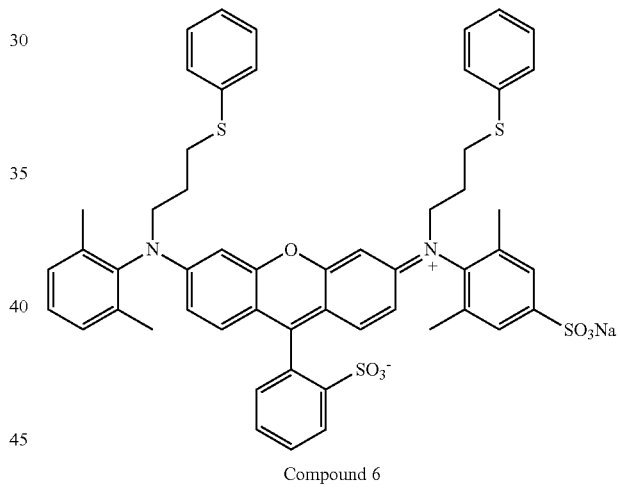

Compound 6

In a 1-neck 100 ml RBF, NMP (50 ml), D-1 (3.454 g, 18.566 mmol) and NaI (2.764 g, 18.566 mmol) were introduced, and stirred for 30 minutes at 45° C. After that, Acid Red 289 (TCI Co., Ltd.) (5.021 g, 7.426 mmol) and K$_2$CO$_3$ (2.566 g, 18.566 mmol) were slowly added to the reaction solution, the result was reacted for 4 hours at 95° C., and the reaction solution was cooled to room temperature. The result was filtered under vacuum, the filtrate was introduced to ethyl acetate (EA) (500 ml), and the result was stirred for 30 minutes. The precipitates were filtered under vacuum. As a result, a colorant (5.970 g, 7.055 mmol) having Compound 6 as a main product was obtained, and the yield was 95%.

Ionization mode=:APCI−:m/z=956 [M−Na]−, Exact Mass: 976

Synthesis Example 7: Synthesis of Compound 7

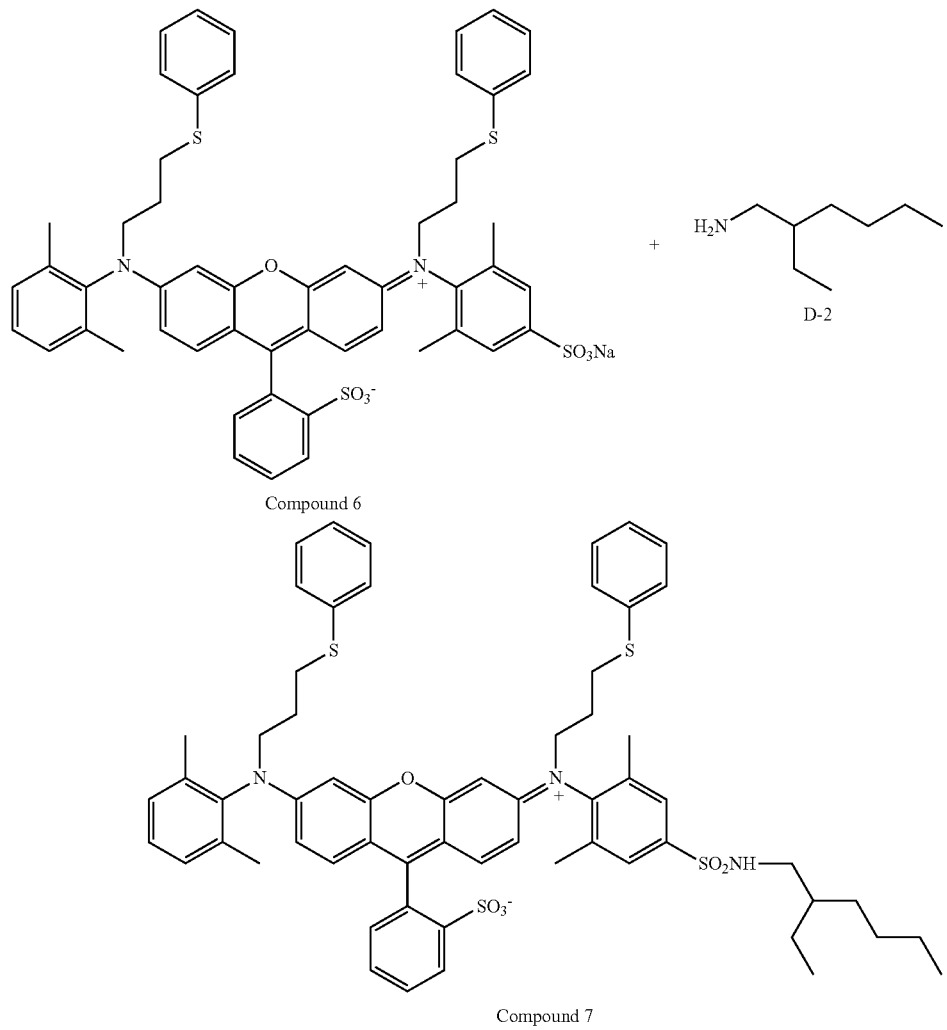

Compound 6

Compound 7

Trichloromethane (CHCl$_3$) and dimethylformamide (DMF) were introduced and stirred at 0° C. After that, thionyl chloride (SOCl$_2$) (3.327 g, 28.220 mmol) was introduced thereto, and the result was further stirred for 30 minutes at 0° C. The colorant (5.970 g, 7.055 mmol) having Compound 6 as a main product was slowly added thereto. After that, the temperature was raised to 35° C., and the result was stirred for 1 hour and 30 minutes. After that, the reaction solution was cooled to 0° C., 2-ethylhexylamine (3.645 g, 28.220 mmol) was dropped thereto, triethyleneimine (Et$_3$N) (8.561 g, 84.660 mmol) was dropped thereto, and the result was stirred for 16 hours at room temperature. The solvent was removed under vacuum, and water and methylene chloride (MC) were added thereto for extraction. The organic layer passed through sodium sulfate (Na$_2$SO$_4$), and then the solvent was removed under vacuum.

After that, the precipitates were separated through column chromatography (eluent-methylene chloride:methanol). As a result, a colorant (5.225 g, 2.117 mmol) having Compound 7 as a main product was obtained, and the yield was 30%.

Ionization mode=:APCI+:m/z=1066 [M+H]+, Exact Mass: 1065

Synthesis Example 8: Synthesis of Compound 8

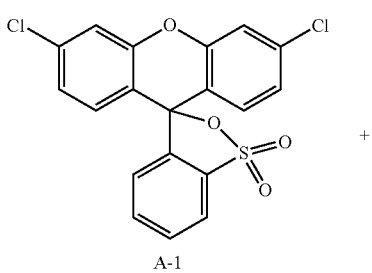

A-1

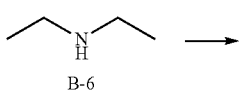

B-6

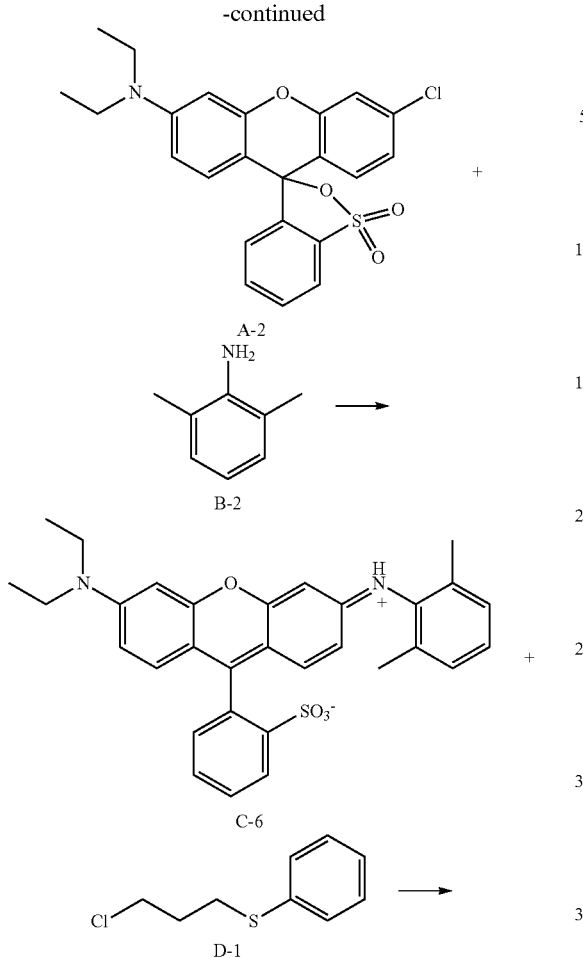

nol). As a result, Compound A-2 (0.98 g, 2.228 mmol) was obtained, and the yield was 30%.

In a 1-neck 100 ml RBF, A-2 (0.98 g, 2.228 mmol), NMP (20 ml) and B-2 (1.079 g, 8.912 mmol) were introduced and stirred. The result was reacted for 4 hours at 150° C., and the reaction solution was cooled to room temperature. The reaction solution was introduced to 1 M HCl (500 ml), the result was stirred for 30 minutes, and the precipitates were filtered under vacuum and washed to obtain C-6. In a 1-neck 100 ml RBF, NMP (20 ml), D-1 (1.036 g, 5.570 mmol) and NaI (0.829 g, 5.570 mmol) were introduced, and stirred for 30 minutes at 45° C. After that, C-6 and $K_2CO_3$ (0.770 g, 5.570 mmol) were slowly added to the reaction solution, the result was reacted for 4 hours at 95° C., and the reaction solution was cooled to room temperature. The reaction solution was introduced to DI-Water (500 ml), and the result was stirred for 30 minutes and extracted with MC. The organic layer was washed with brine, and passed through $Na_2SO_4$ to remove water. The solvent was removed under vacuum. After that, the result was separated through column chromatography (eluent-methylene chloride:methanol). As a result, Compound 8 (0.753 g, 1.114 mmol) was obtained, and the yield was 50%.

Ionization mode=:APCI+:m/z=677 [M+H]+, Exact Mass: 676

Synthesis Example 9: Synthesis of Compound 9

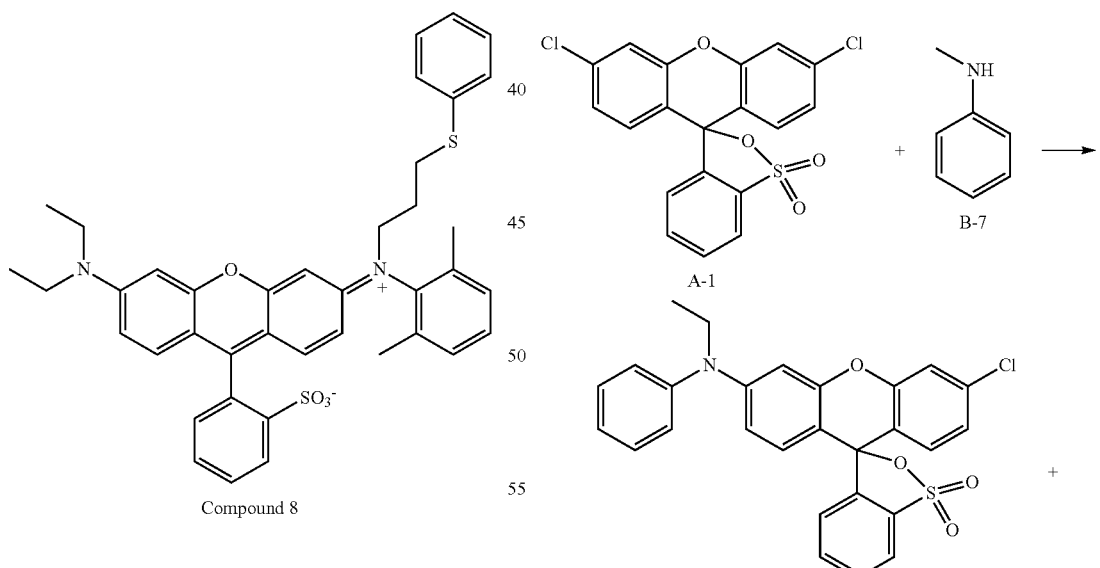

In a 1-neck 200 ml RBF, A-1 (3 g, 7.426 mmol), MeOH (90 ml) and B-6 (2.171 g, 29.704 mmol) were introduced and stirred. The result was reacted for 2 hours at room temperature and then introduced to 1 M HCl (1000 ml), and the result was stirred for 30 minutes and extracted with MC. The organic layer was washed with brine, and passed through $Na_2SO_4$ to remove water. The solvent was removed under vacuum. After that, the result was separated through column chromatography (eluent-methylene chloride:metha- -continued

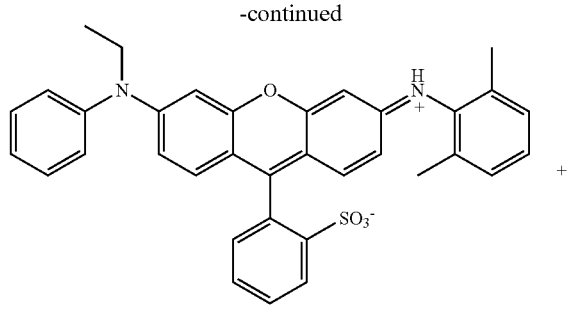

C-7

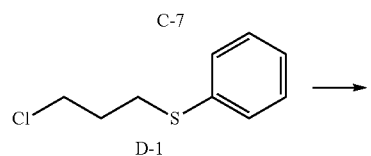

D-1

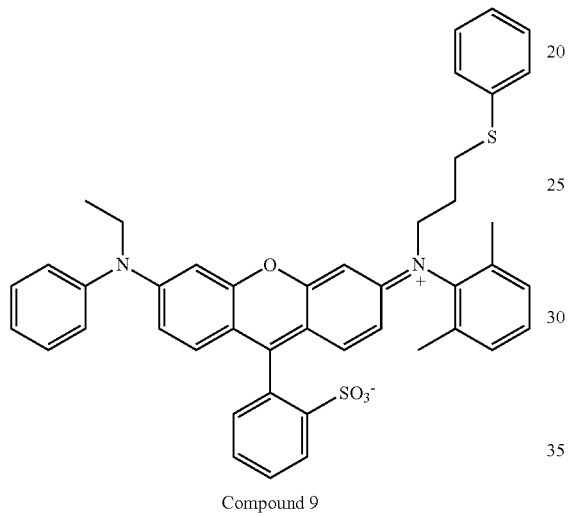

Compound 9

In a 1-neck 200 ml RBF, A-1 (3 g, 7.426 mmol), MeOH (90 ml) and B-7 (3.976 g, 37.130 mmol) were introduced and stirred. The result was reacted for 3 hours at room temperature and then introduced to 1 M HCl (1000 ml), and the result was stirred for 30 minutes and extracted with MC. The organic layer was washed with brine, and passed through $Na_2SO_4$ to remove water. The solvent was removed under vacuum. After that, the result was separated through column chromatography (eluent-methylene chloride:methanol). As a result, Compound A-3 (2.9056 g, 5.941 mmol) was obtained, and the yield was 80%.

In a 1-neck 100 ml RBF, A-3 (1.090 g, 2.228 mmol), NMP (20 ml) and B-2 (1.079 g, 8.912 mmol) were introduced and stirred. The result was reacted for 4 hours at 150° C., and the reaction solution was cooled to room temperature. The reaction solution was introduced to 1 M HCl (500 ml), the result was stirred for 30 minutes, and the precipitates were filtered under vacuum and washed to obtain C-7. In a 1-neck RBF 100 ml, NMP (20 ml), D-1 (1.036 g, 5.570 mmol) and NaI (0.829 g, 5.570 mmol) were introduced, and stirred for 30 minutes at 45° C. After that, C-7 and $K_2CO_3$ (0.770 g, 5.570 mmol) were slowly added to the reaction solution, the result was reacted for 4 hours at 95° C., and the reaction solution was cooled to room temperature. The reaction solution was introduced to DI-Water (500 ml), and the result was stirred for 30 minutes and extracted with MC. The organic layer was washed with brine, and passed through $Na_2SO_4$ to remove water. The solvent was removed under vacuum. After that, the result was separated through column chromatography (eluent-methylene chloride:methanol). As a result, Compound 9 (0.726 g, 1.003 mmol) was obtained, and the yield was 45%.

Ionization mode=:APCI+:m/z=725 [M+H]+, Exact Mass: 724

Synthesis Example 10: Synthesis of Compound 10

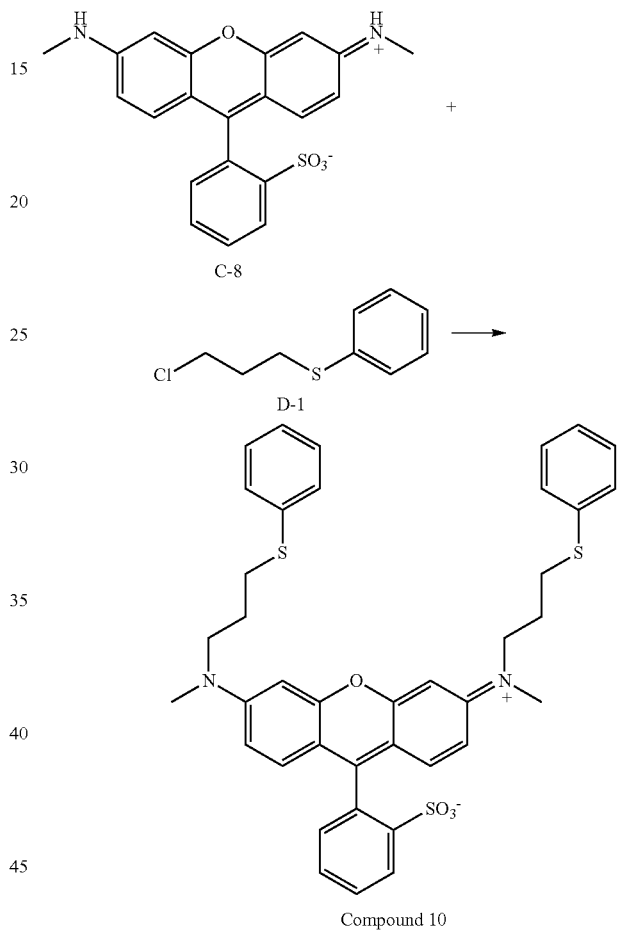

Compound 10

In a 1-neck 200 ml RBF, D-1 (9.466 g, 50.704 mmol) and NaI (7.549 g, 50.704 mmol) were introduced to NMP (80 ml), and the result was stirred for 30 hours at 45° C. After that, C-8 (5 g, 12.676 mmol) and $K_2CO_3$ (7.008 g, 50.704 mmol) were slowly added to the reaction solution, the result was reacted for 4 hours at 95° C., and the reaction solution was cooled to room temperature. The reaction solution was introduced to DI-Water (1000 ml), and the result was stirred for 30 minutes and extracted with MC. The organic layer was washed with brine, and passed through $Na_2SO_4$ to remove water. The solvent was removed under vacuum. After that, the result was separated through column chromatography (eluent-methylene chloride:methanol). As a result, Compound 10 (6.600 g, 9.507 mmol) was obtained, and the yield was 75%.

Ionization mode=:APCI+:m/z=695 [M+H]+, Exact Mass: 694

Synthesis Example 11: Synthesis of Compound 11

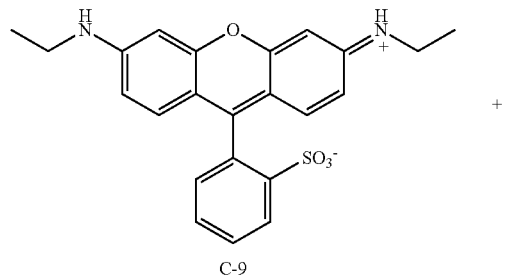

C-9

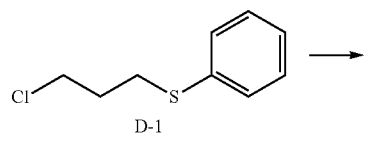

D-1

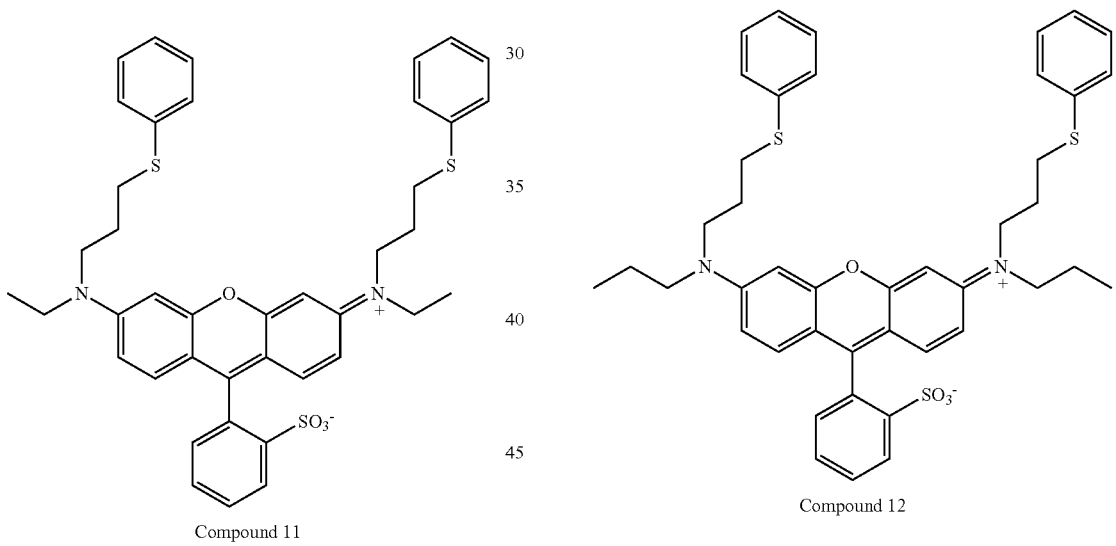

Compound 11

In a 1-neck 200 ml RBF, D-1 (9.466 g, 50.704 mmol) and NaI (7.549 g, 50.704 mmol) were introduced to NMP (80 ml), and the result was stirred for 30 hours at 45° C. After that, C-9 (5.351 g, 12.676 mmol) and K₂CO₃ (7.008 g, 50.704 mmol) were slowly added to the reaction solution, the result was reacted for 4 hours at 95° C., and the reaction solution was cooled to room temperature. The reaction solution was introduced to DI-Water (1000 ml), and the result was stirred for 30 minutes and extracted with MC. The organic layer was washed with brine, and passed through Na₂SO₄ to remove water. The solvent was removed under vacuum. After that, the result was separated through column chromatography (eluent-methylene chloride:methanol). As a result, Compound 11 (7.232 g, 10.014 mmol) was obtained, and the yield was 79%.

Ionization mode=:APCI+:m/z=723 [M+H]+, Exact Mass: 722

Synthesis Example 12: Synthesis of Compound 12

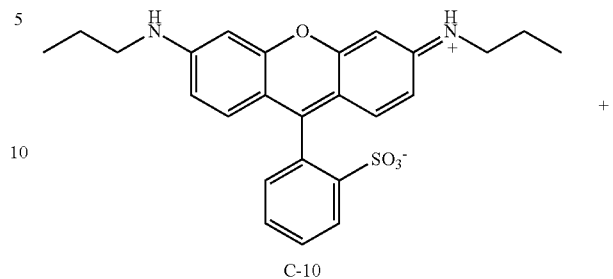

C-10

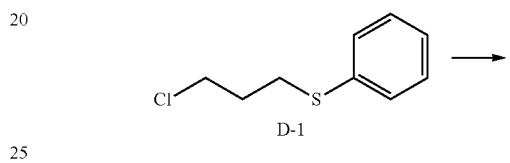

D-1

Compound 12

In a 1-neck 200 ml RBF, D-1 (9.466 g, 50.704 mmol) and NaI (7.549 g, 50.704 mmol) were introduced to NMP (80 ml), and the result was stirred for 30 hours at 45° C. After that, C-10 (5.711 g, 12.676 mmol) and K₂CO₃ (7.008 g, 50.704 mmol) were slowly added to the reaction solution, the result was reacted for 4 hours at 95° C., and the reaction solution was cooled to room temperature. The reaction solution was introduced to DI-Water (1000 ml), and the result was stirred for 30 minutes and extracted with MC. The organic layer was washed with brine, and passed through Na₂SO₄ to remove water. The solvent was removed under vacuum. After that, the result was separated through column chromatography (eluent-methylene chloride:methanol). As a result, Compound 12 (6.664 g, 8.873 mmol) was obtained, and the yield was 70%.

Ionization mode=:APCI+:m/z=751 [M+H]+, Exact Mass: 750

Synthesis Example 13: Synthesis of Compound 13

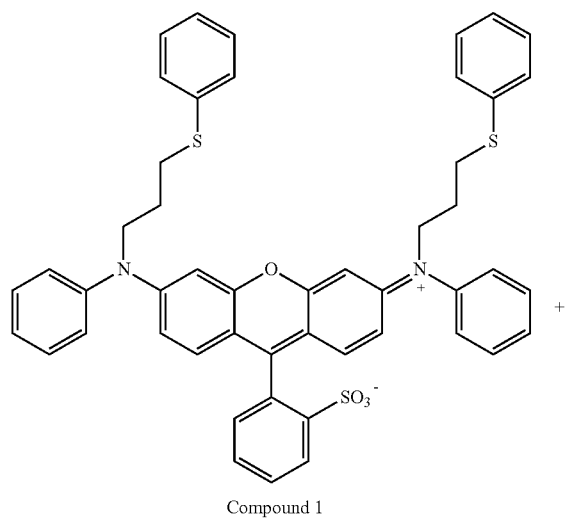

Compound 1

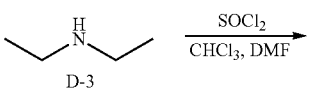
D-3

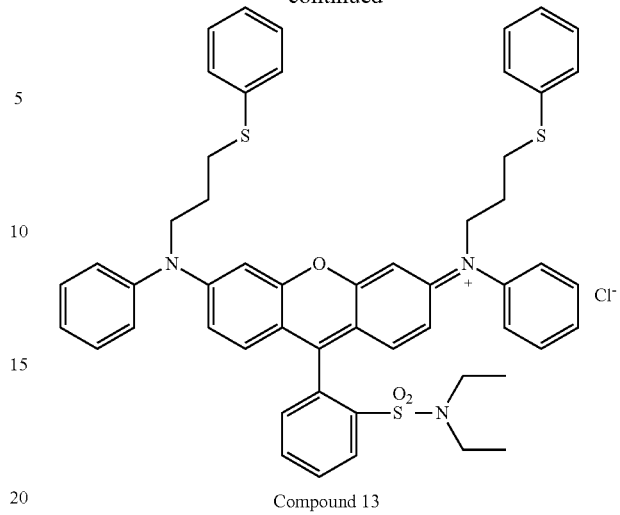

Compound 13

CHCl$_3$ and DMF were introduced and stirred at 25° C. After that, SOCl$_2$ (3.327 g, 28.220 mmol) was introduced thereto, and the result was further stirred for 30 minutes at 0° C. Compound 1 (5.779 g, 7.055 mmol) was slowly added thereto. After that, the temperature was raised to 35° C., and the result was stirred for 1 hour and 30 minutes. After that, the reaction solution was cooled to 0° C., D-3 (2.064 g, 28.220 mmol) was dropped thereto, Et$_3$N (8.561 g, 84.660 mmol) was dropped thereto, and the result was stirred for 16 hours at room temperature. The solvent was removed under vacuum, and water and MC were added thereto for extraction. The organic layer passed through Na$_2$SO$_4$, and then the solvent was removed under vacuum.

After that, the precipitates were separated through column chromatography (eluent-methylene chloride:methanol). As a result, Compound 13 (3.405 g, 3.739 mmol) was obtained, and the yield was 53%.

Ionization mode=:ESI+:m/z=874 [M-Cl]+, Exact Mass: 874

Synthesis Example 14: Synthesis of Compound 14

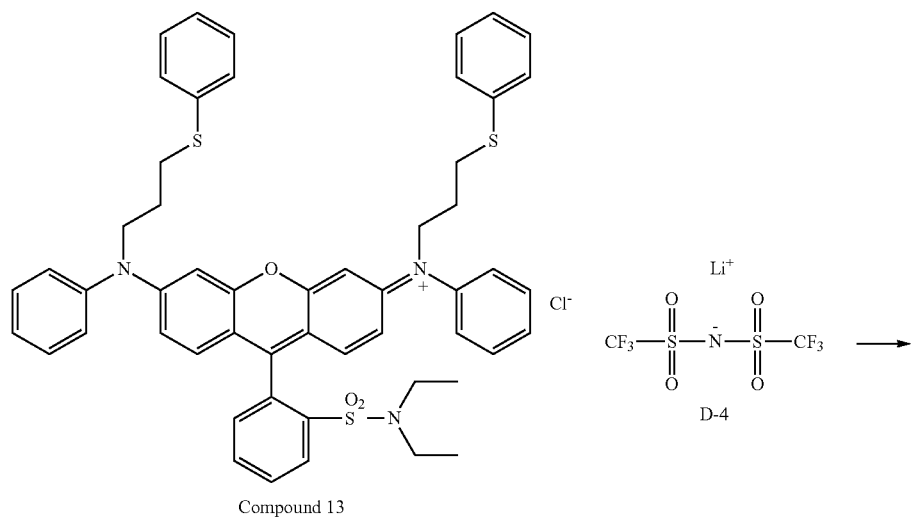

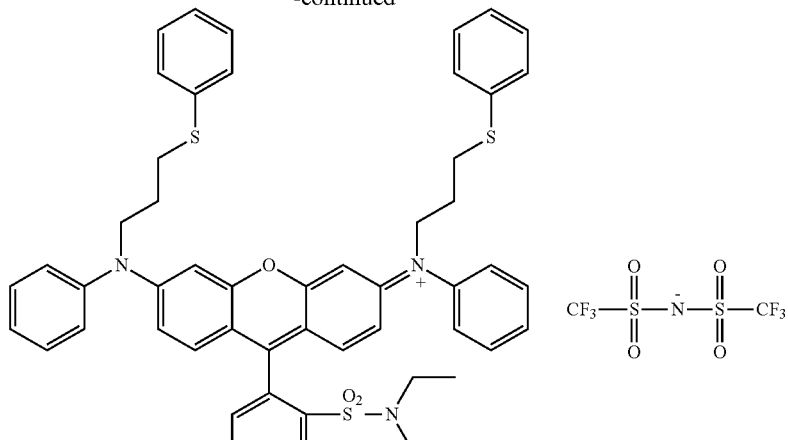

Compound 14

Compound 13 (2 g, 2.200 mmol) was introduced to MC (30 g) and dissolved therein. After that, a solution dissolving D-4 (0.663 g, 2.310 mmol) in DI-water (5 g) was slowly dropped to the Compound 13 solution. After reacting for 3 hours, the organic layer was separated, passed through $Na_2SO_4$ to remove water, and then the solvent was removed under vacuum. As a result, Compound 14 (2.287 g, 1.980 mmol) was obtained, and the yield was 90%.

Ionization mode=:ESI–:m/z=280 [M-coloring cation]–, Exact Mass: 280

Synthesis Example 15: Synthesis of Compound 15

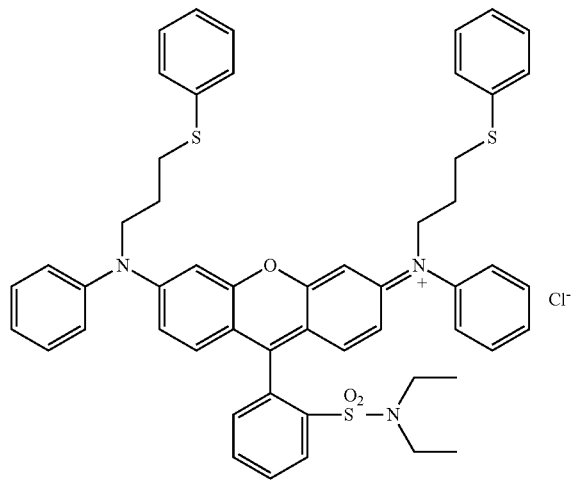

Compound 13

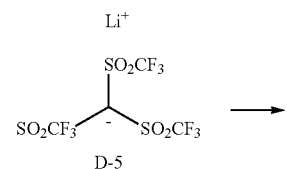

D-5

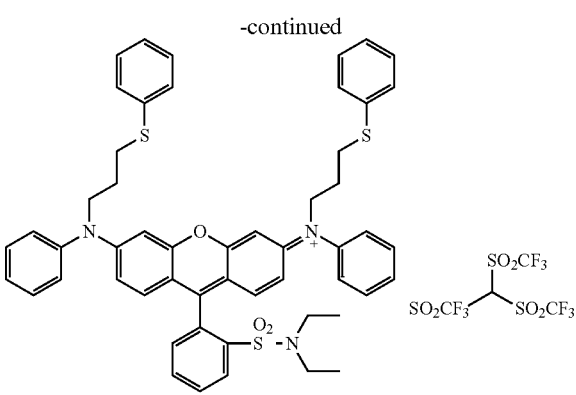

Compound 15

Compound 15 was obtained by progressing synthesis under the same condition as in Synthesis Example 14 except that D-4 was changed to D-5.

Comparative Example Compound 1

A coloring agent of the following structural formula (Basic blue 7) was purchased from TCI Chemicals and used as Comparative Example Compound 1.

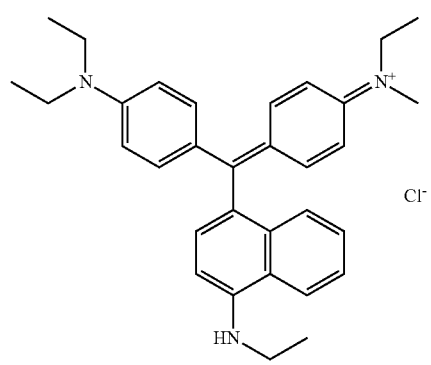 [SMILES: CCNc1ccc(C(=C2C=CC(=[N+](C)CC)C=C2)c2ccc(N(CC)CC)cc2)c2ccccc12 ; [Cl-]]

Comparative Example Compound 2

A coloring agent of the following structural formula (Rhodamine 6 G) was purchased from Sigma-Aldrich, and used as Comparative Example Compound 2.

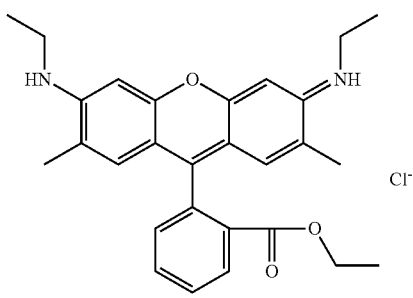 [SMILES: CC/N=c1\cc2oc3cc(NCC)c(C)cc3c(-c3ccccc3C(=O)OCC)c-2cc1C ; [Cl-]]

Comparative Example Compound 3

A coloring agent of the following structural formula (Rhodamine 6 G) was purchased from Sigma-Aldrich, and used as Comparative Example Compound 3.

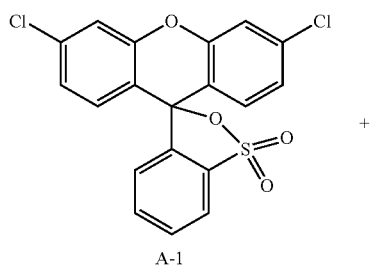

A-1

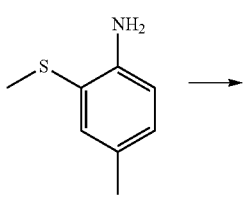

B-8

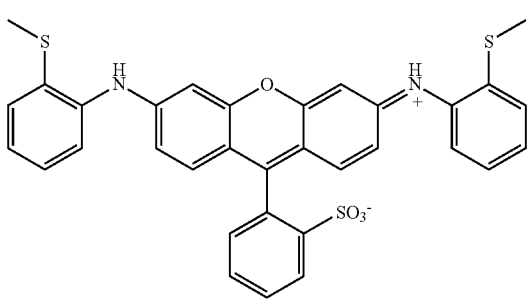

C-11

CH$_3$—I

D-2

-continued

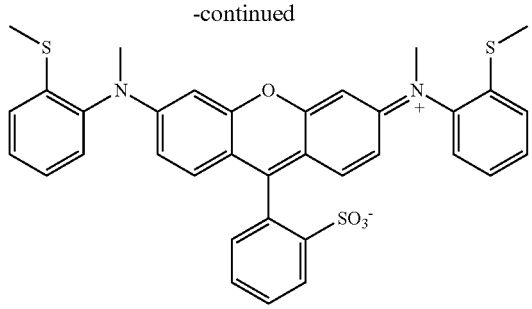

Comparative Example Compound 3

In a 1-neck 200 ml RBF, A-1 (5 g, 12.340 mmol), NMP (50 ml) and B-8 (10.31 g, 74.030 mmol) were introduced and stirred. The result was reacted for 4 hours at 150° C., and the reaction solution was cooled to room temperature. The reaction solution was introduced to 1 M HCl (500 ml), the result was stirred for 30 minutes, and the precipitates were filtered under vacuum and washed. In a 1-neck 200 ml RBF, NMP (50 ml), C-11 and D-2 (7.006 g, 49.360 mmol) and K$_2$CO$_3$ (6.822 g, 49.360 mmol) were slowly added to the reaction solution, the result was reacted for 4 hours at 95° C., and the reaction solution was cooled to room temperature. The reaction solution was introduced to DI-Water (500 ml), the result was stirred for 30 minutes, and the precipitates were filtered under vacuum and washed.

After that, the precipitates were separated through column chromatography (eluent-methylene chloride:methanol). As a result, Comparative Compound 3 (4.730 g, 7.404 mmol) was obtained, and the yield was 60%.

Ionization mode=:APCI+:m/z=639 [M+H]+, Exact Mass: 638

Preparation Example of Resin Composition

Example 1

A total of 100 g of a resin composition was prepared by mixing 5.554 g of the colorant compound of Synthesis Example 1, 10.376 g of a copolymer of benzyl methacrylate and methacrylic acid (molar ratio 70:30, acid value 113 potassium hydroxide (KOH) mg/g, weight average molecular weight measured by gel permeation chromatography (GPC) 20,000 g/mol, molecular weight distribution (PDI) 2.0, solid content (S.C) 25%, including a propylene glycol monomethyl ether acetate (PGMEA) solvent) as a binder resin, 12.443 g of dipentaerythritol hexaacrylate (DPHA) (Nippon Kayaku Co., Ltd.) as a polymerizable compound, 2.018 g of 1-369 (BASF Corporation) as a photoinitiator, 1.013 g of F-475 (DIC Corporation) as an additive, and 68.593 g of a propylene glycol monomethyl ether acetate (PGMEA) solvent.

Example 2

A resin composition was prepared in the same manner as in Example 1 except that 5.554 g of colorant compound 5 of Synthesis Example 5 was used instead of 5.554 g of the colorant compound of Synthesis Example 1.

Example 3

A resin composition was prepared in the same manner as in Example 1 except that 5.554 g of colorant compound 9 of Synthesis Example 9 was used instead of 5.554 g of the colorant compound of Synthesis Example 1.

Example 4

A resin composition was prepared in the same manner as in Example 1 except that 5.554 g of colorant compound 12 of Synthesis Example 12 was used instead of 5.554 g of the colorant compound of Synthesis Example 1.

Comparative Example 1

A resin composition was prepared in the same manner as in Example 1 except that 5.554 g of Comparative Example Compound 1 was used instead of 5.554 g of the colorant compound of Synthesis Example 1.

Comparative Example 2

A resin composition was prepared in the same manner as in Example 1 except that 5.554 g of Comparative Example Compound 2 was used instead of 5.554 g of the colorant compound of Synthesis Example 1.

Comparative Example 3

A resin composition was prepared in the same manner as in Example 1 except that 5.554 g of Comparative Example Compound 3 was used instead of 5.554 g of the colorant compound of Synthesis Example 1.

Experimental Example

Heat Resistance Evaluation

For the colorant compositions of the examples and the comparative examples, heat resistance was evaluated using a method as follows.

Specifically, each of the resin compositions of Examples 1 to 4, and Comparative Examples 1 to 3 was spin coated on glass (5 cm²×5 cm²), and prebaked (prB) for 100 seconds at 100° C. to form a film. The distance between the film-formed substrate and a photomask was employed as 300 μm, and the whole surface of the substrate was irradiated with an exposure of 40 mJ/cm² using a stepper.

The exposed substrate was developed for 60 seconds in a developing solution (KOH, 0.05%), and post-baked (PB) for 20 minutes at 230° C. to prepare a color pattern-formed substrate.

For heat resistance evaluation on the substrate gone through prebake (prB) treatment, an absorption spectrum in a visible region having a range of 380 nm to 780 nm was obtained using a spectroscope (MCPD-Otsuka Electronics Co., Ltd.). In addition, for the substrate gone through post-bake (PB), a transmittance spectrum was obtained in the same measurement range using the same device.

In addition, ΔEab was calculated according to the following Equation 1 using a value E (L*, a*, b*) obtained using the absorption spectrum obtained during the prebake and the post-bake, and a C light source backlight, and the results are shown in Table 1. Each of L*, a*, b* in the Equation 1 is as defined by the International Commission on Illumination ("CIE") in 1976. L* is a numerical value representing the brightness, and has a value between 0 and 100; a* means a near degree between red and green, and has a positive/negative value and b* means a near degree between yellow and blue, and has a positive/negative value.

$$\Delta Eab(L^*,a^*,b^*) = \{(\Delta L^*)^2 + (\Delta a^*)^2 + (\Delta b^*)^2\}^{1/2} \quad \text{[Equation 1]}$$

Having a small ΔEab value means having excellent color heat resistance.

When ΔEab<3, it may be used as a coloring for a color filter.

TABLE 1

|  | ΔEab (post-bake-prebake) |
| --- | --- |
| Example 1 | 0.95 |
| Example 2 | 0.91 |
| Example 3 | 2.28 |
| Example 4 | 1.02 |
| Comparative Example 1 | 26.52 |
| Comparative Example 2 | 23.95 |
| Comparative Example 3 | 2.59 |

When referring to Table 1, the color pattern substrates formed using the resin compositions of Examples 1 to 4 of the present disclosure exhibited higher color stability compared to the color pattern substrates formed using the resin compositions of Comparative Example 1 to Comparative Example 3 using colorings known in the art, and exhibited excellent heat resistance with a very small difference in the transmittance spectrum (ΔEab) between post-bake and after post-bake.

Optical Property Evaluation

After prebaking (prB) and post-baking (PB) the color filter substrates manufactured in Examples 1 to 4 and Comparative Example 3, 380 nm to 480 nm transmittance measured on the post-baked (PB) substrate using a spectrometer (MCPD Otsuka Electronics Co., Ltd.) is shown in FIG. 1. Particularly, In R, G and B color filters, luminance of the blue color filter is affected by 380 nm to 480 nm transmittance. When 380 nm to 480 nm transmittance is excellent, luminance of the blue color filter may increase. Examples 1 to 4 had higher 380 nm to 480 nm transmittance compared to Comparative Example 3, and was able to increase luminance of the blue color filter.

The invention claimed is:

1. A compound represented by Chemical Formula 1:

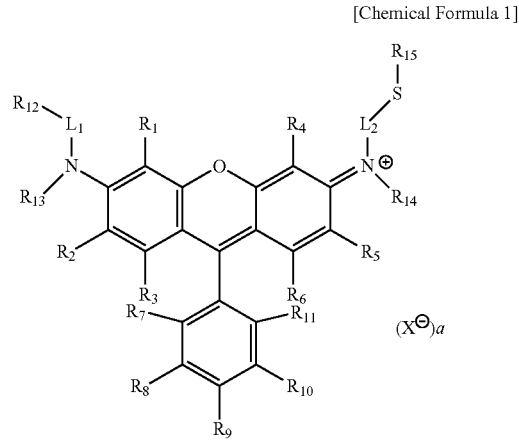

[Chemical Formula 1]

wherein, in the Chemical Formula 1, $R_1$ to $R_6$ are each independently selected from the group consisting of hydrogen; deuterium; a halogen group; a nitro group; a substituted or unsubstituted linear or branched alkyl group having 1 to 30 carbon atoms; a substituted or unsubstituted alkoxy group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms;

$R_7$ to $R_{11}$ are the same as or different from each other, and each independently selected from the group consisting of hydrogen; deuterium; —OH; —$SO_3^-$; —$SO_3H$; —$SO_3^-Z^+$; —$COO^-$; —COOH; —$COO^-Z^+$; —COORa; —$SO_3Rb$; —$SO_2NRcRd$; $SO_2NHRe$; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms;

$Z^+$ represents $^+N(Rf)_4$, $Na^+$ or $K^+$;

Ra to Rf are each independently selected from the group consisting of a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms;

Rc and Rd bond to each other to form a monocyclic or polycyclic heterorng having 3 to 10 carbon atoms including a nitrogen atom;

Rfs are the same as or different from each other;

at least one of $R_7$ to $R_{11}$ is —$SO_3^-$; —$SO_3H$; —$SO_3^-Z^+$; —$SO_3Rb$; —$SO_2NRcRd$; or —$SO_2NHRe$;

$R_{12}$ to $R_{14}$ are the same as or different from each other, and each independently selected from the group consisting of hydrogen; deuterium; a substituted or unsubstituted linear or branched alkyl group having 1 to 30 carbon atoms; a substituted or unsubstituted monocyclic or polycyclic aryl group having 6 to 30 carbon atoms; a substituted or unsubstituted monocyclic or polycyclic heteroaryl group having 2 to 30 carbon atoms; and a substituted or unsubstituted sulfide group;

$R_{13}$ and $L_1$ bond to each other to form a monocyclic or polycyclic ring including a nitrogen atom;

a is an integer of 0 or 1;

X is an anionic group;

$R_{15}$ is selected from the group consisting of a substituted or unsubstituted monocyclic or polycyclic aryl group having 6 to 30 carbon atoms; and a substituted or unsubstituted monocyclic or polycyclic heteroaryl group having 2 to 30 carbon atoms;

$L_1$ and $L_2$ are selected from the group consisting of a direct bond; a substituted or unsubstituted linear or branched alkylene group having 1 to 30 carbon atoms; —NH—; —O—; —COO—; —OCO—; —NHCO—; —CONH—; —NR—; —NRCO—; -$L_3$-NH-$L_4$-; -$L_3$-O-$L_4$-; -$L_3$-COO-$L_4$-; -$L_3$-OCO-$L_4$-; -$L_3$-NHCO-$L_4$-; -$L_3$-CONH-$L_4$-; -$L_3$-NR-$L_4$-; and -$L_3$-NRCO-$L_4$-;

$L_3$ and $L_4$ are a substituted or unsubstituted linear or branched alkylene group having 1 to 30 carbon atoms; and R is selected from the group consisting of a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

2. The compound of claim 1, the compound having Chemical Formula 2:

[Chemical Formula 2]

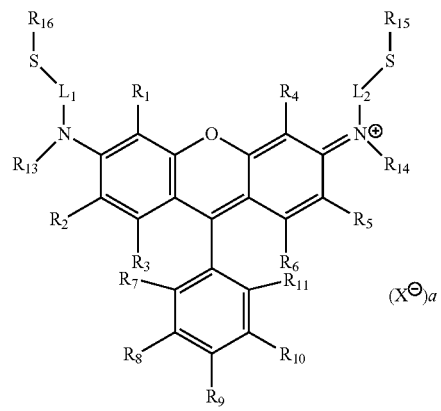

in the Chemical Formula 2, $R_1$ to $R_{11}$, $R_{13}$ to $R_{15}$, $L_1$, $L_2$, a and X are as defined in claim 1; and $R_{16}$ is selected from the group consisting of hydrogen; deuterium; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

3. The compound of claim 1, wherein X is at least one anion selected from the group consisting of an anion of a compound containing oxygen and at least one element selected from the group of tungsten, molybdenum, silicon and phosphorous; a trifluoromethanesulfonic acid anion; a bis(trifluoromethylsulfonyl)amide anion; a bistrifluoromethanesulfonimide anion; a bisperfluoroethylsulfonimide anion; a tetraphenylborate anion; tetrakis(4-fluorophenyl) borate; tetrakis(pentafluorophenyl)borate; tristrifluoromethanesulfonylmethide; and a halogen group.

4. The compound of claim 1, wherein $R_{15}$ is a substituted or unsubstituted monocyclic or polycyclic aryl group having 6 to 30 carbon atoms.

5. The compound of claim 1, wherein $L_2$ is a substituted or unsubstituted linear or branched alkylene group having 1 to 30 carbon atoms.

6. The compound of claim 1, wherein is represented by any one of the following chemical formulae:

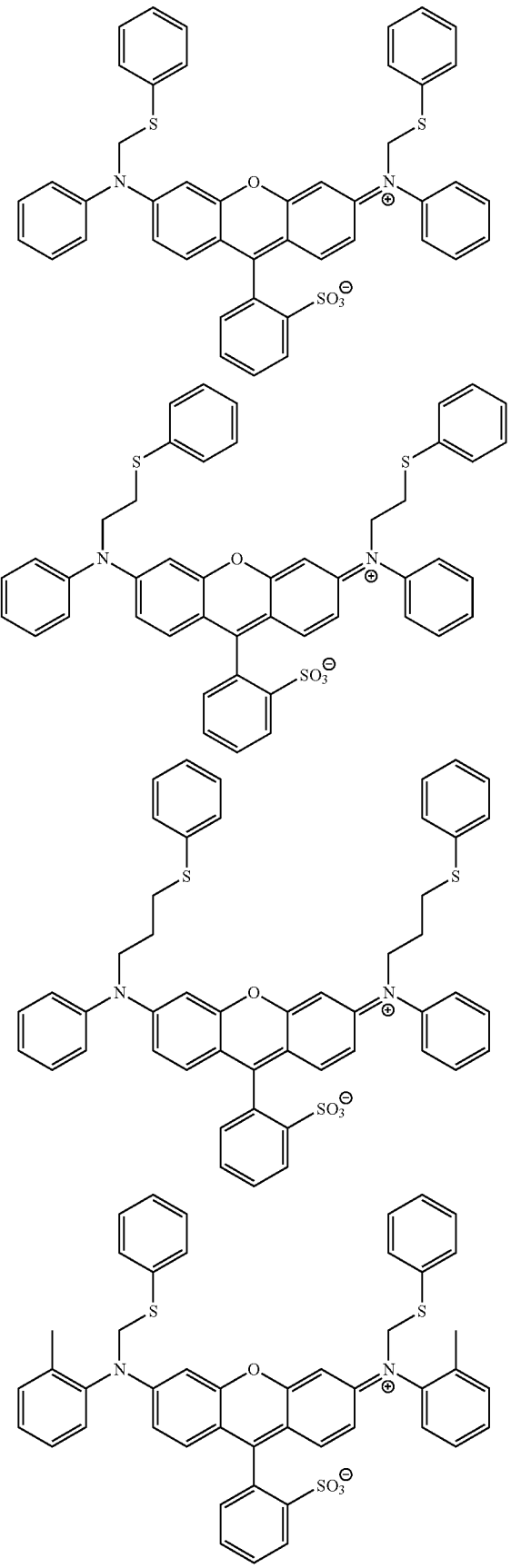

-continued
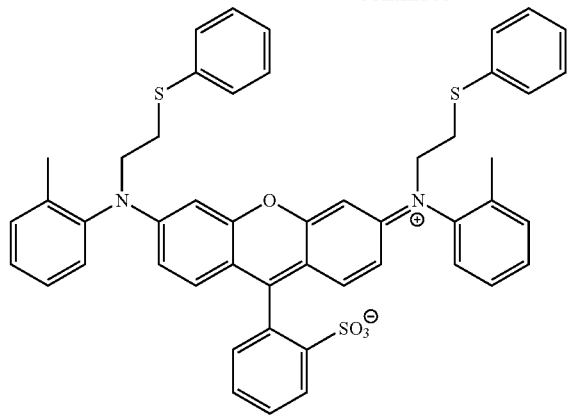
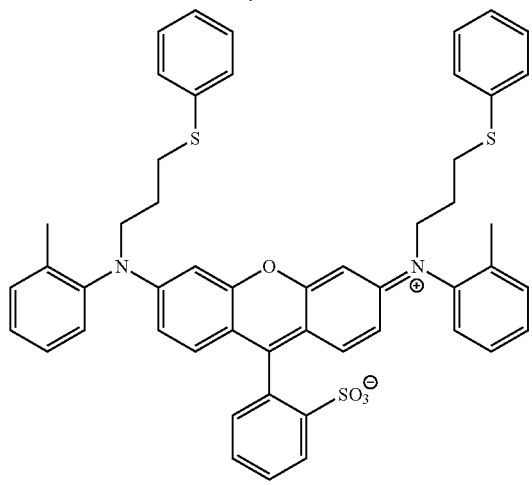
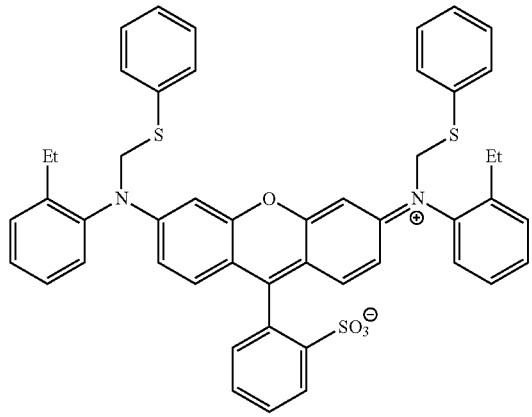
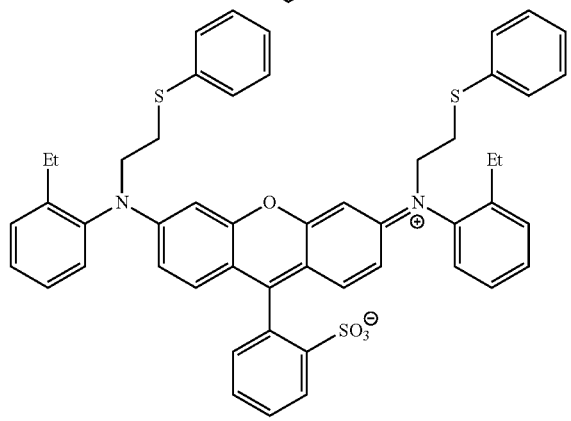

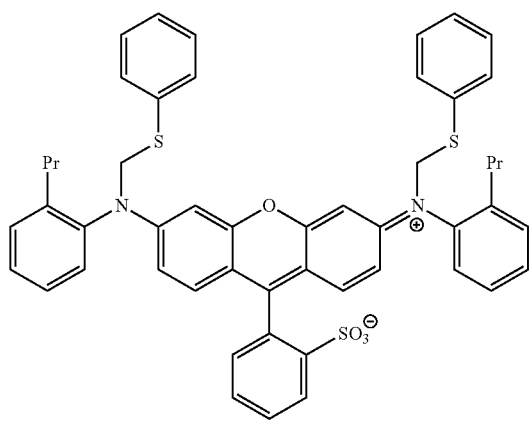
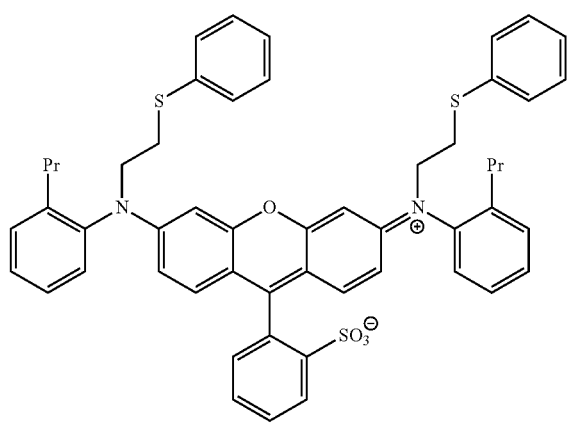
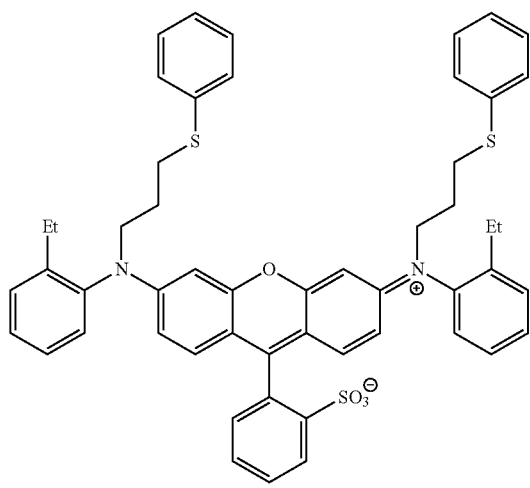

-continued
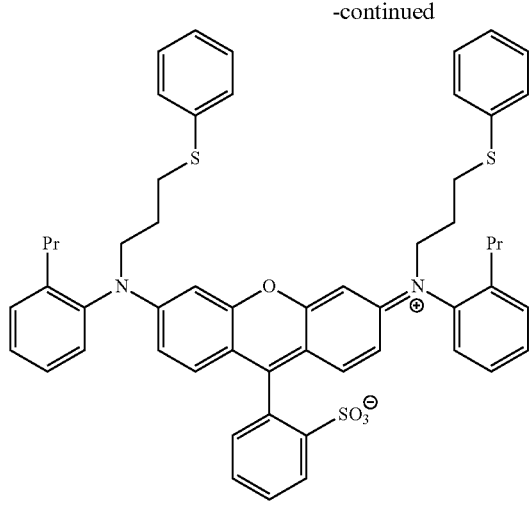
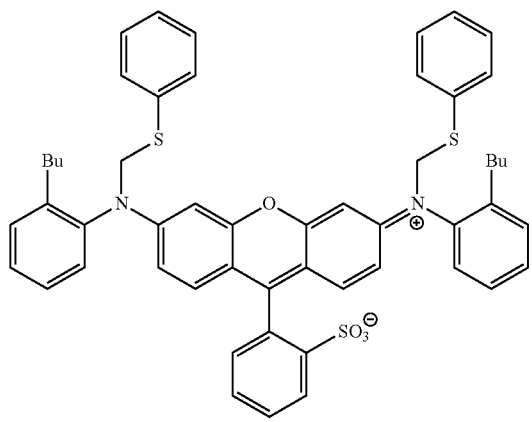
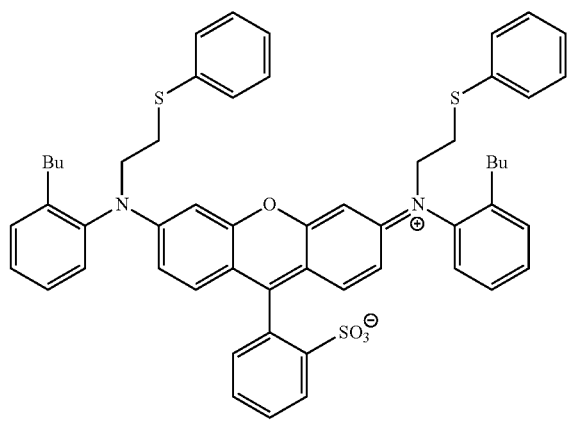

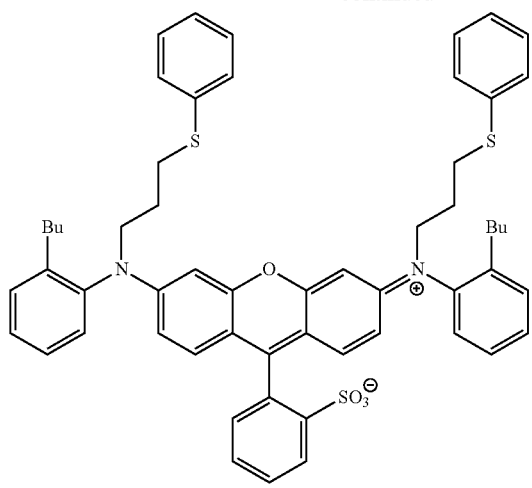
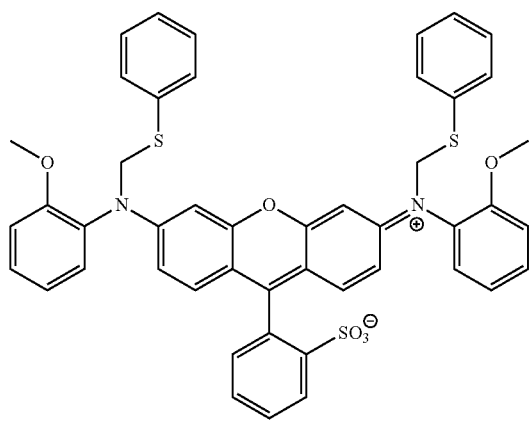
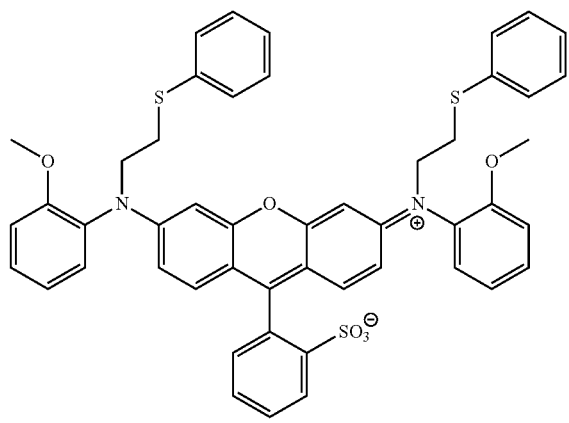

-continued
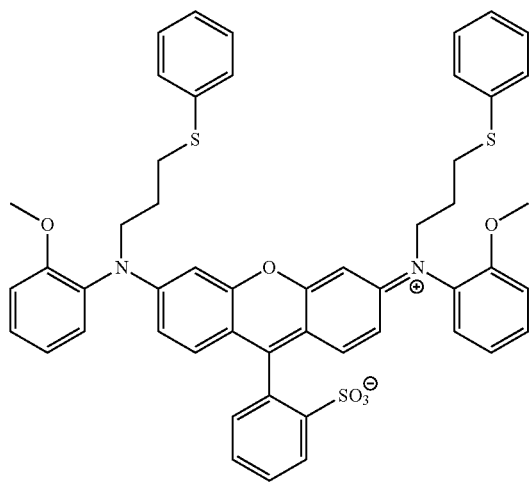
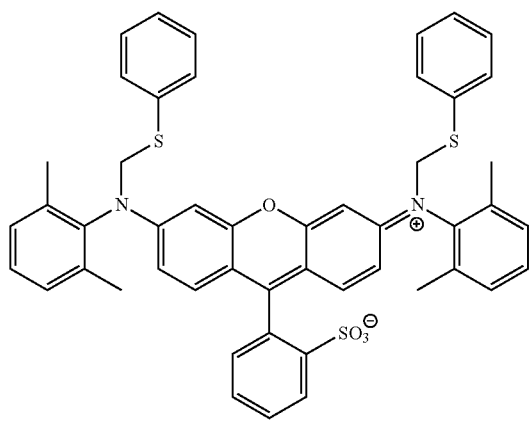
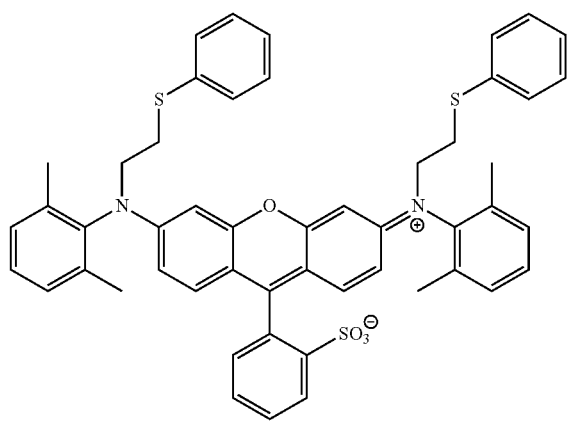

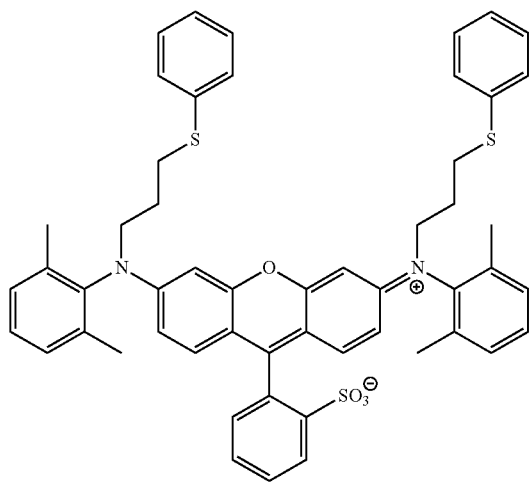
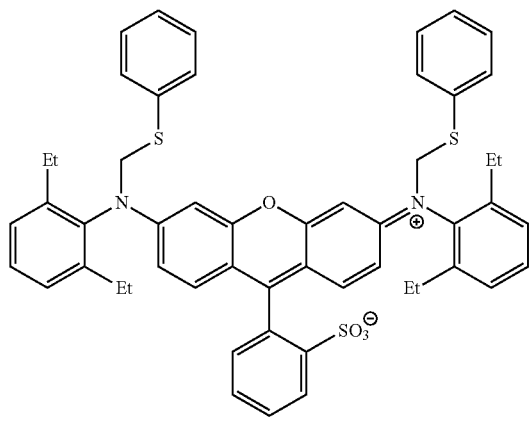
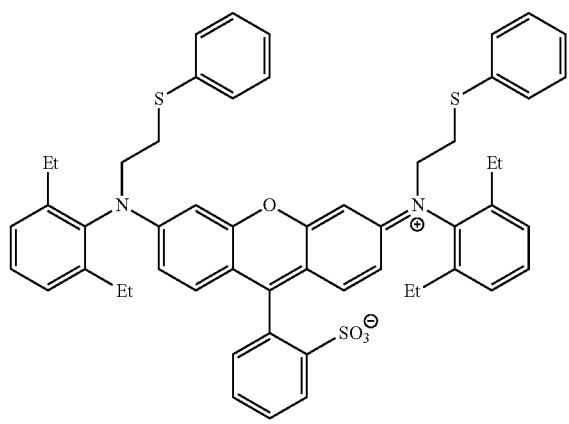

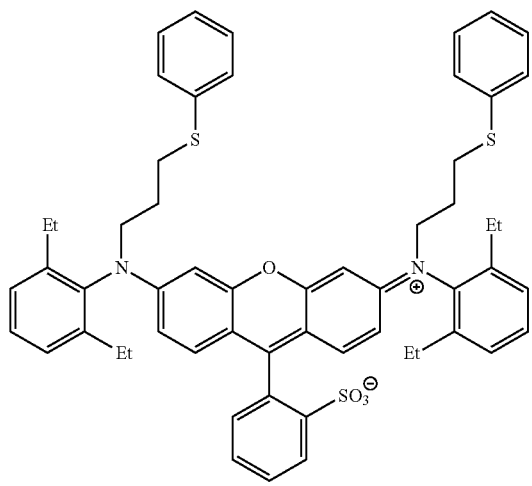
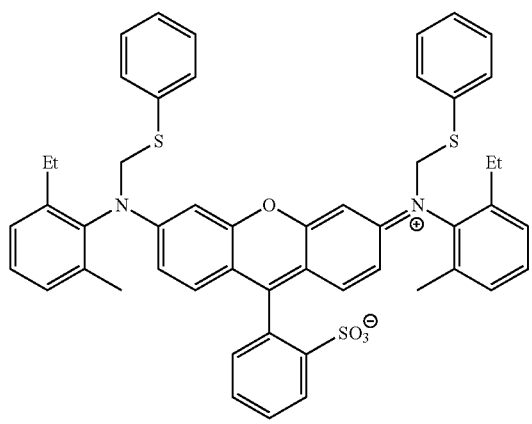
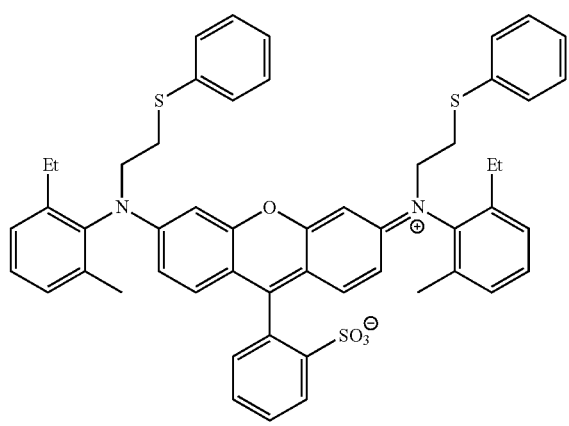

-continued
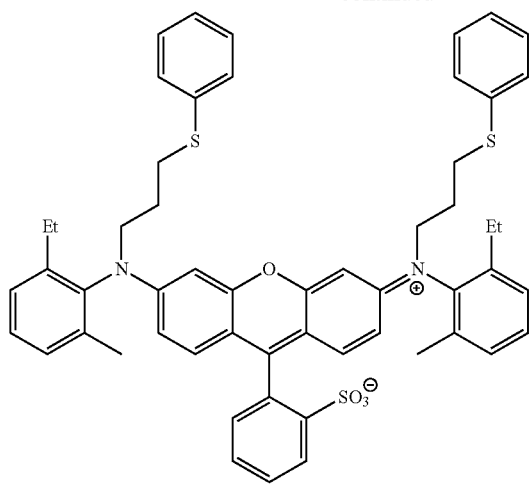
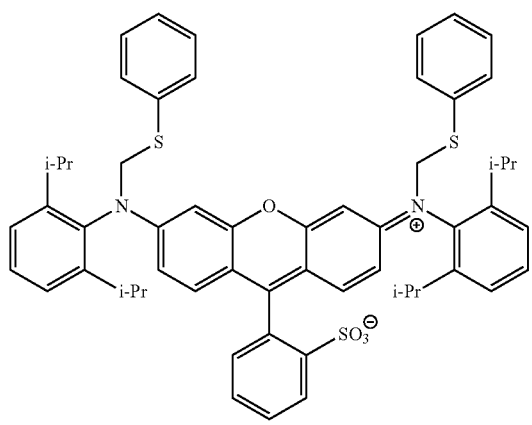
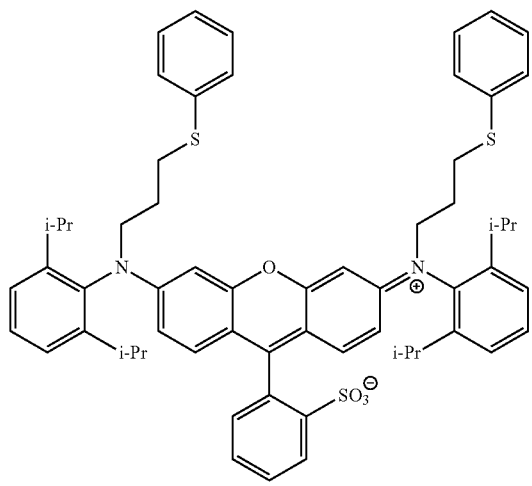

-continued
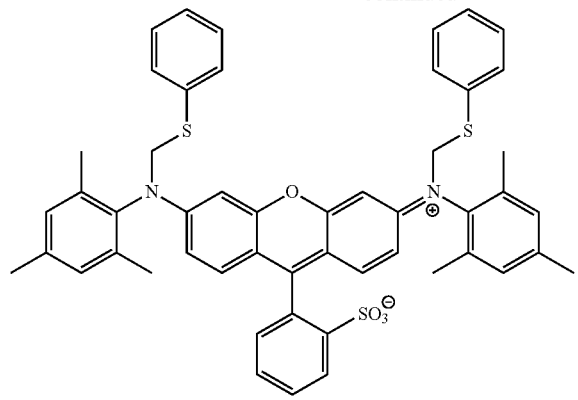
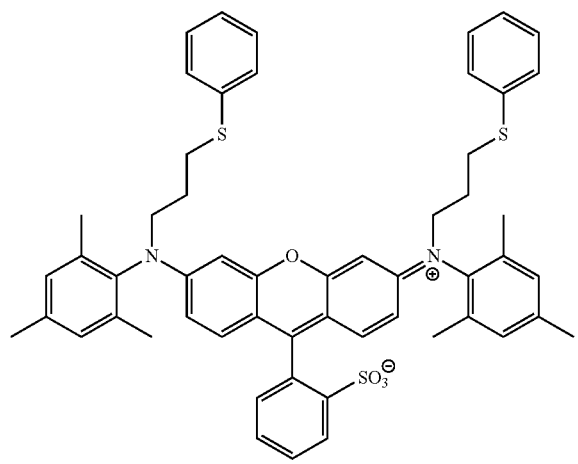
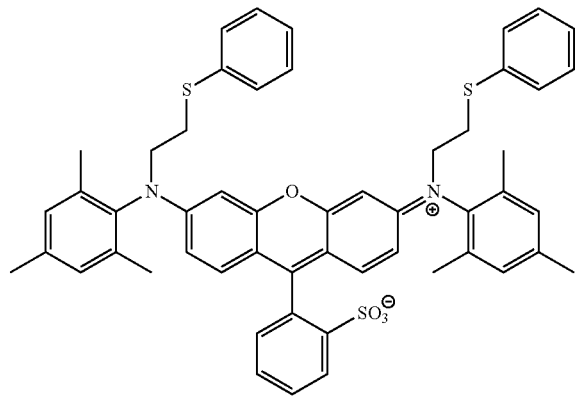
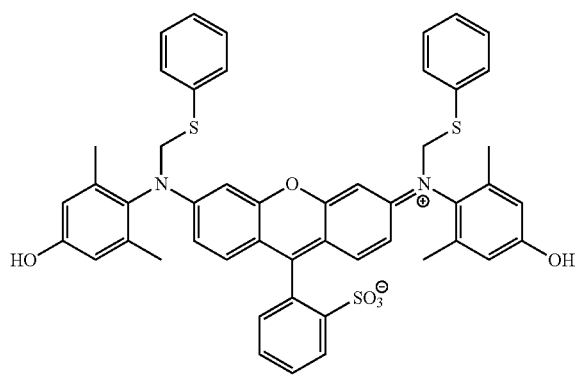

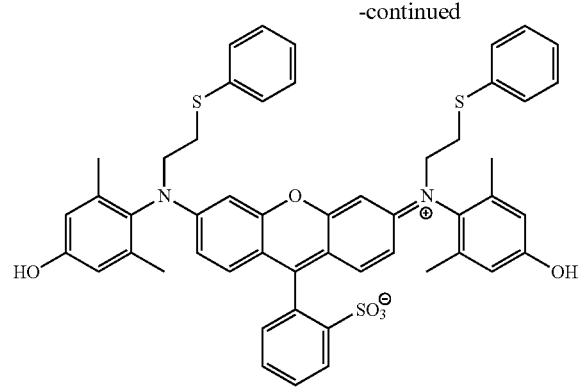
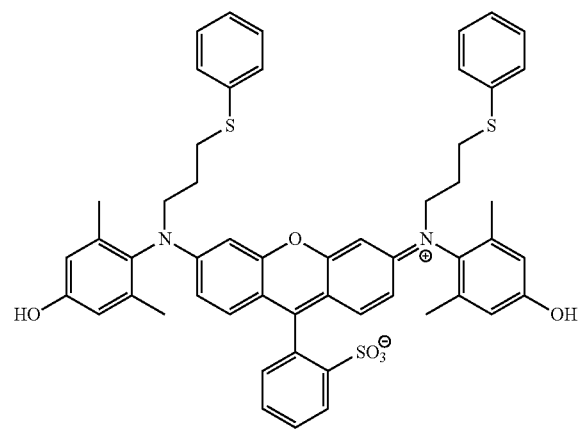
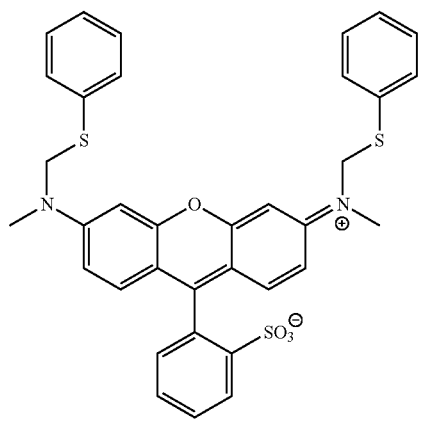
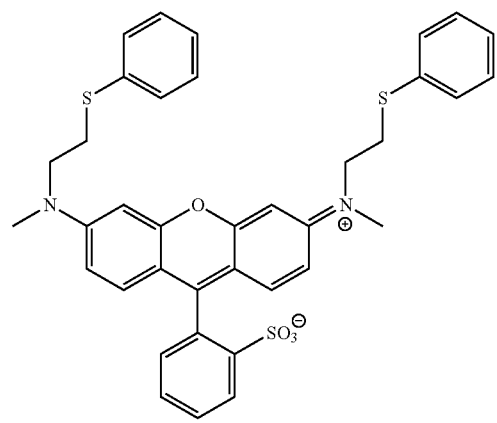

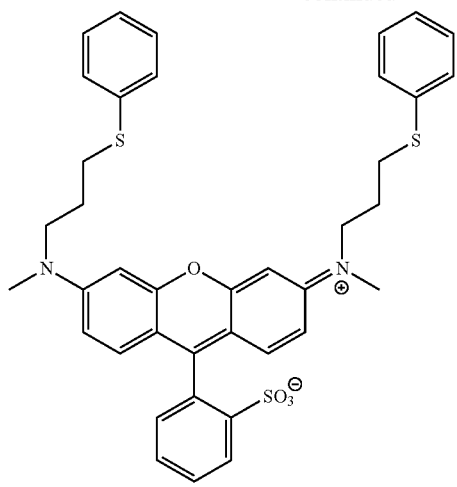
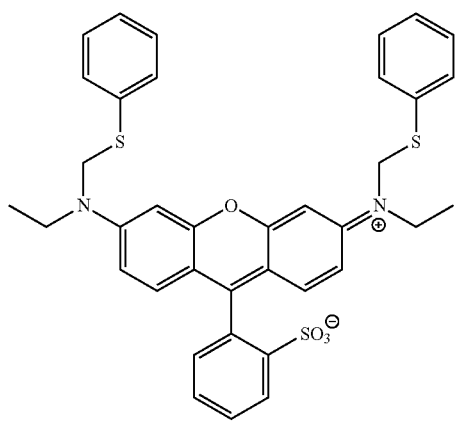
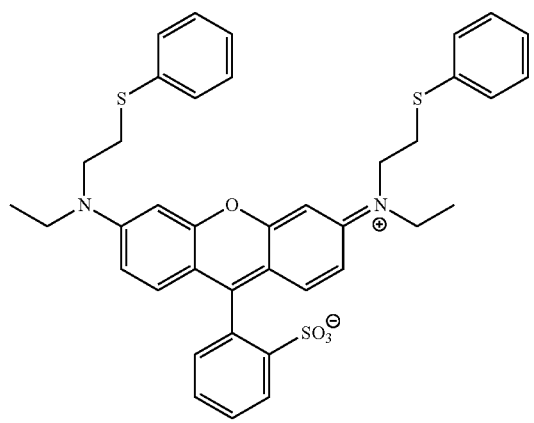

-continued
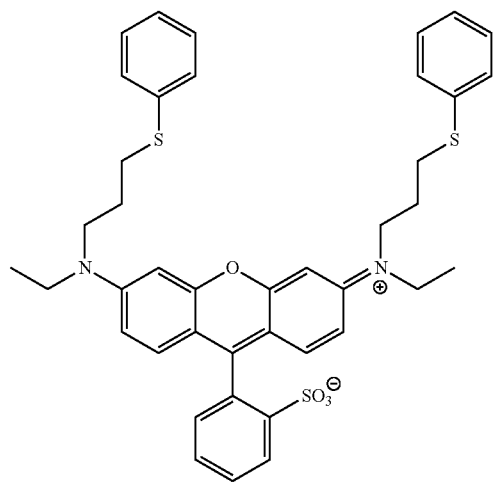
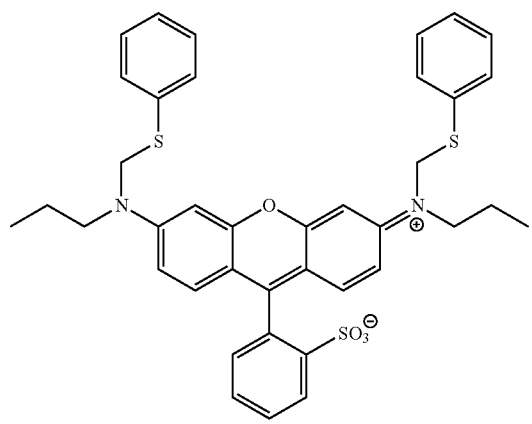
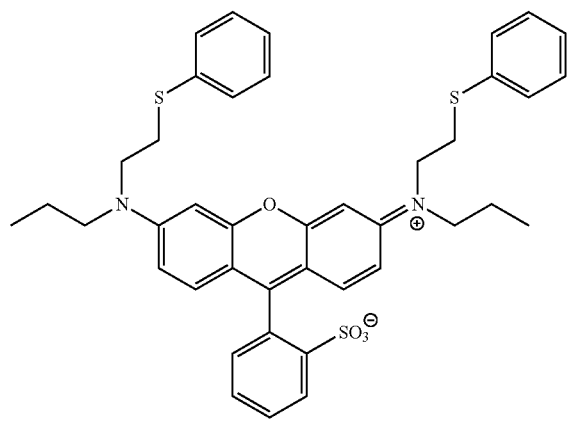

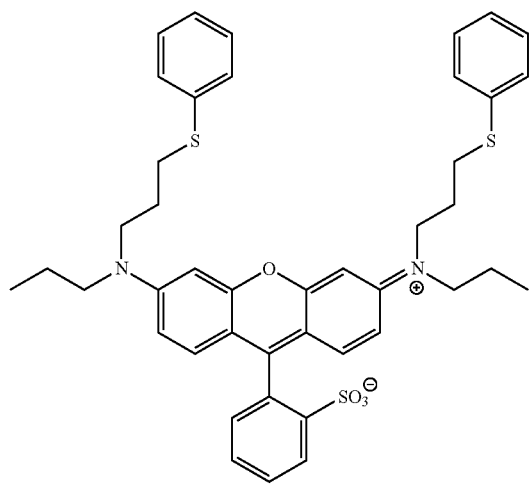
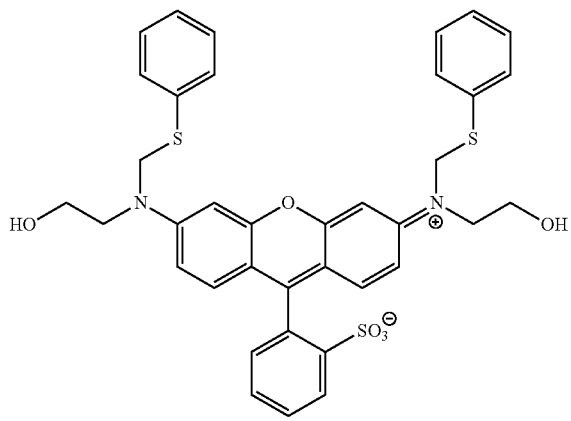
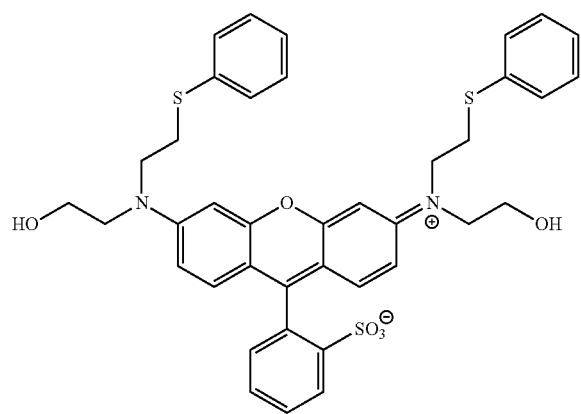

-continued
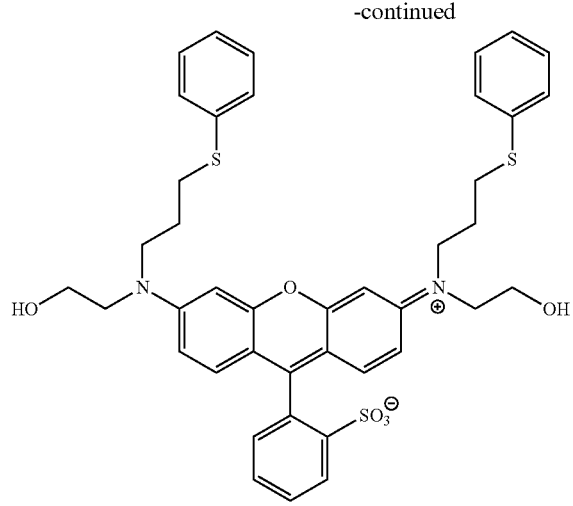
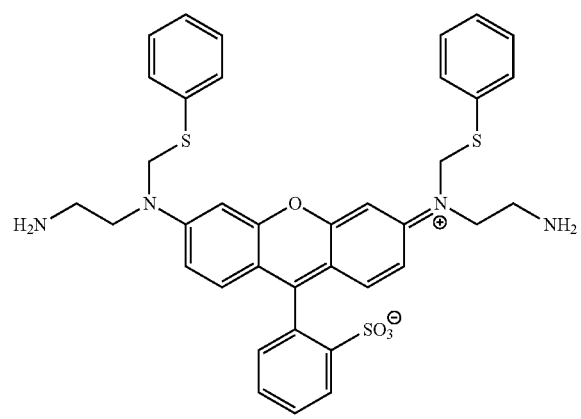
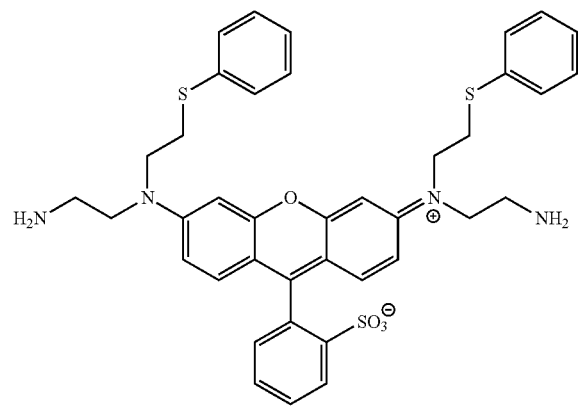

121
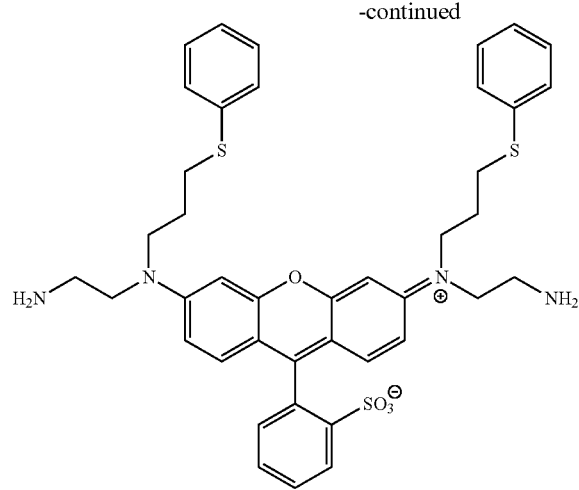
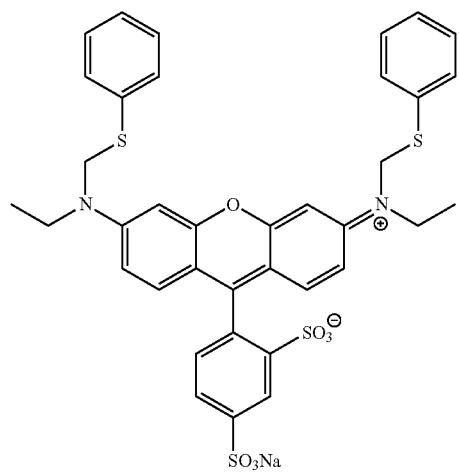
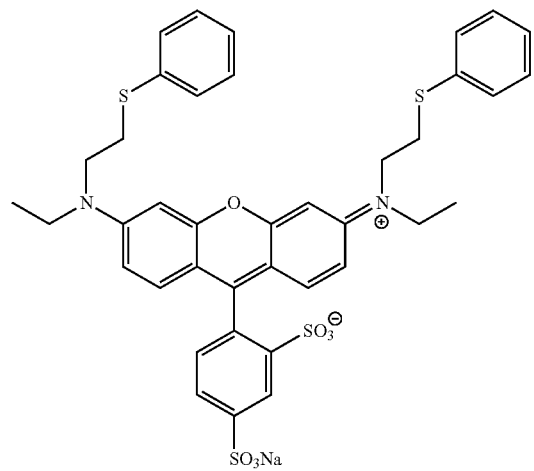

123
-continued
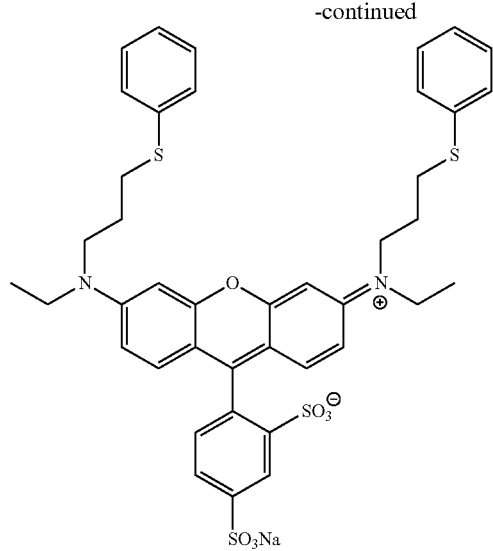
124
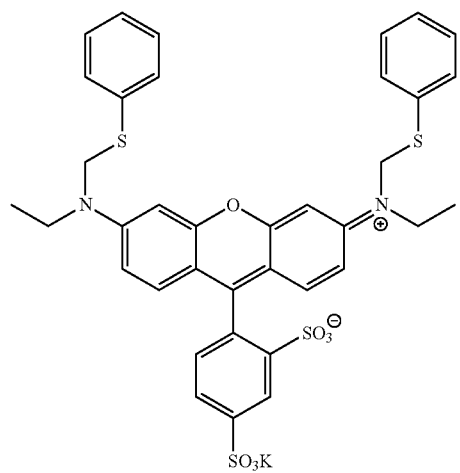
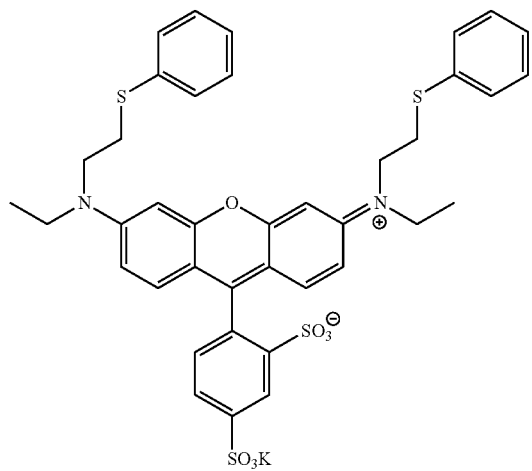

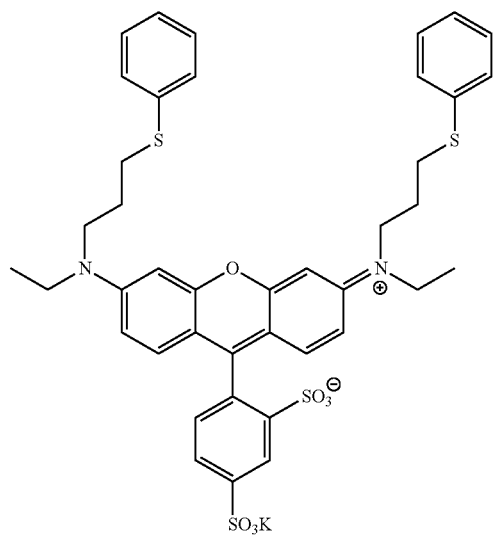
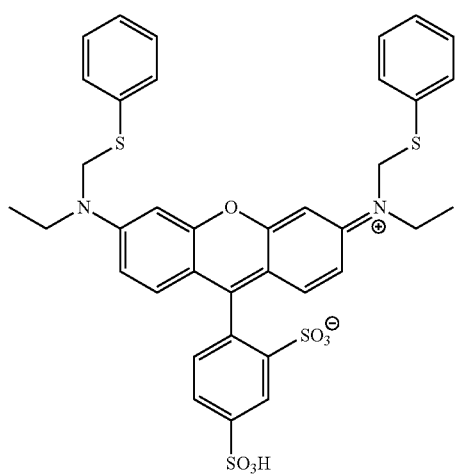
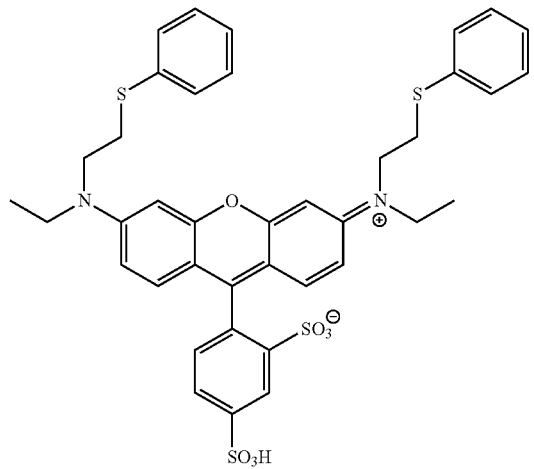

-continued
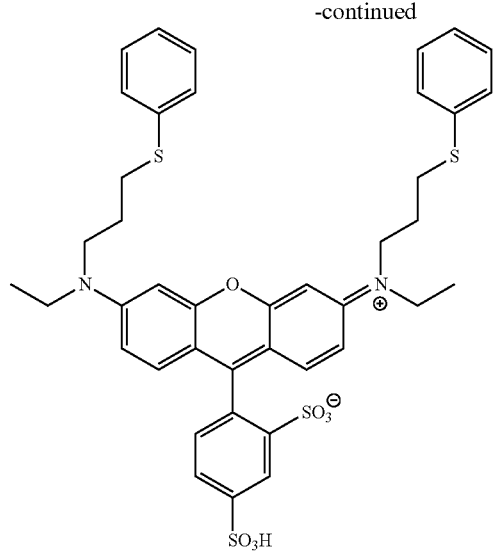
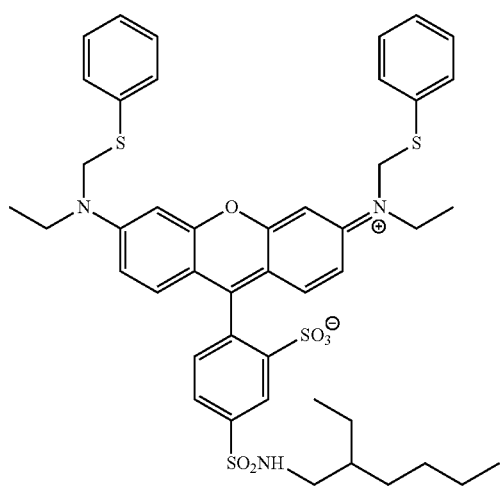
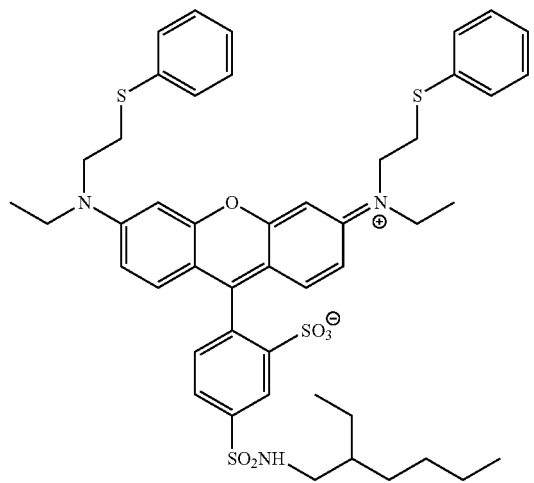

-continued
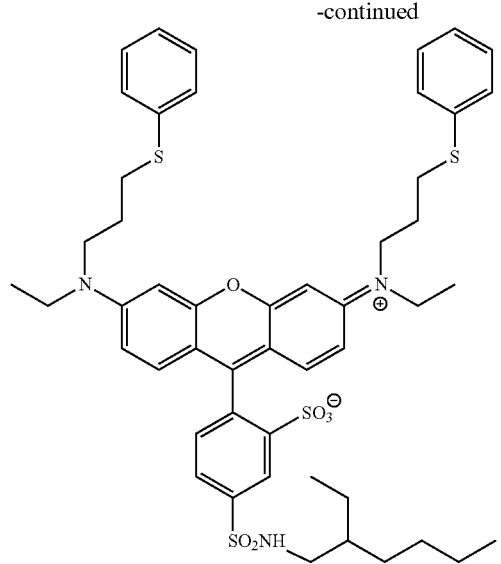
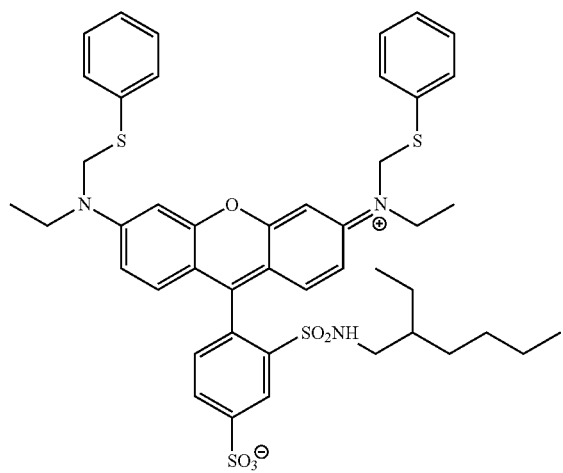
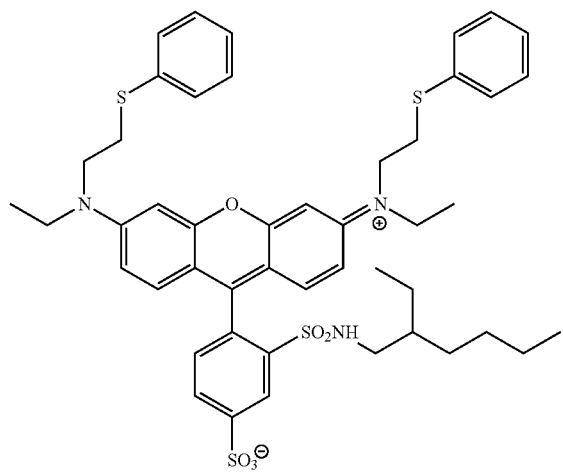

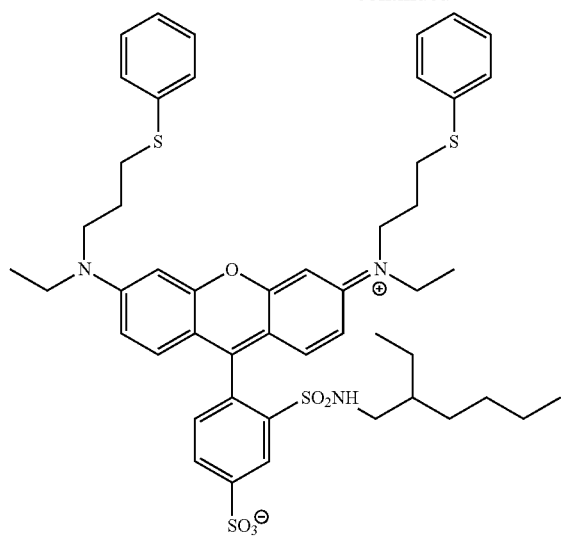
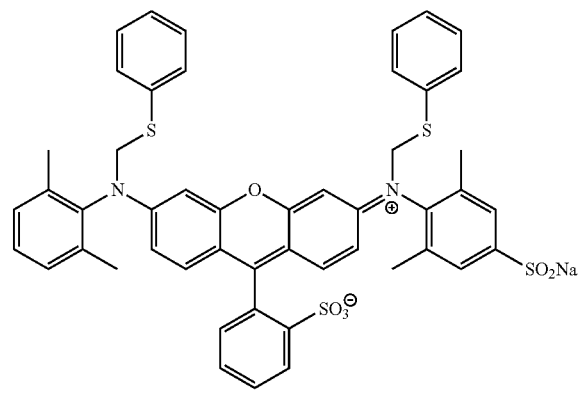
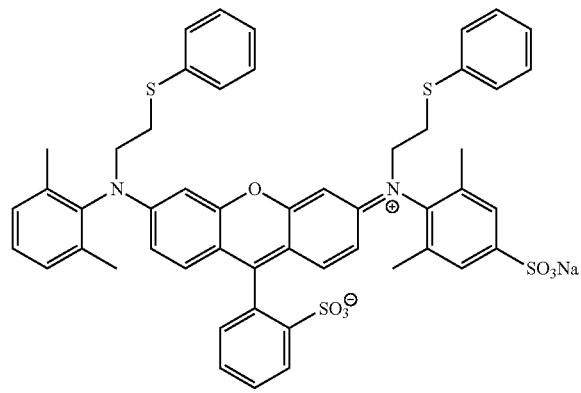

-continued
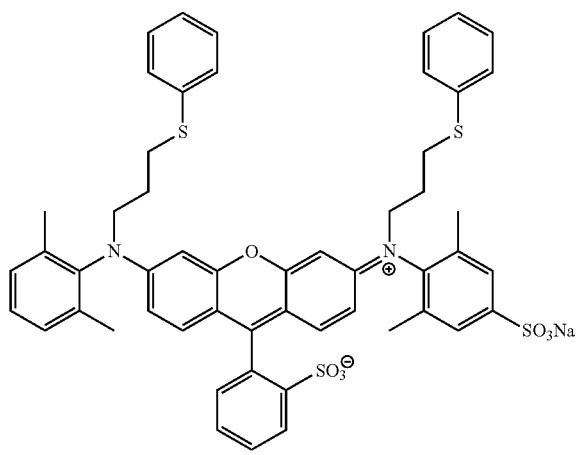
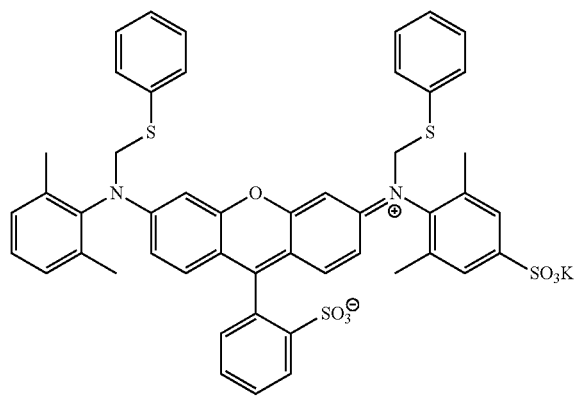
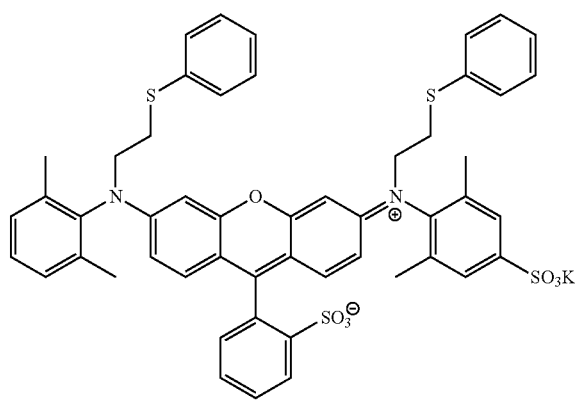
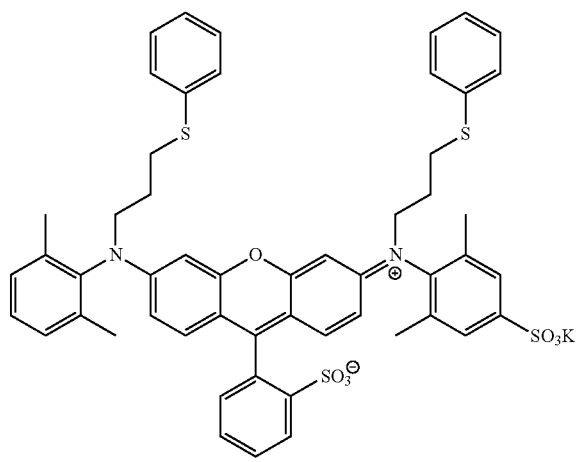

-continued
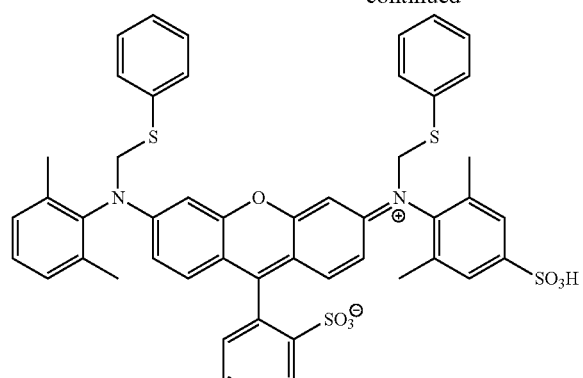
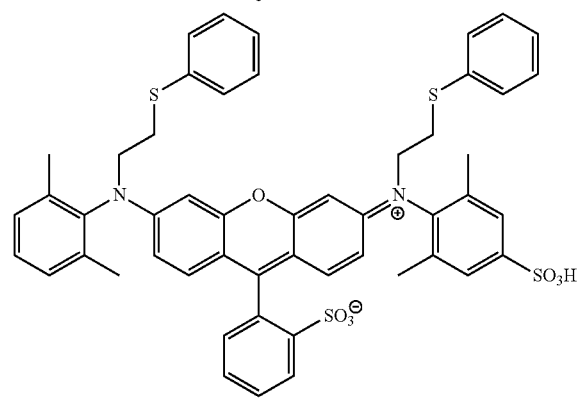
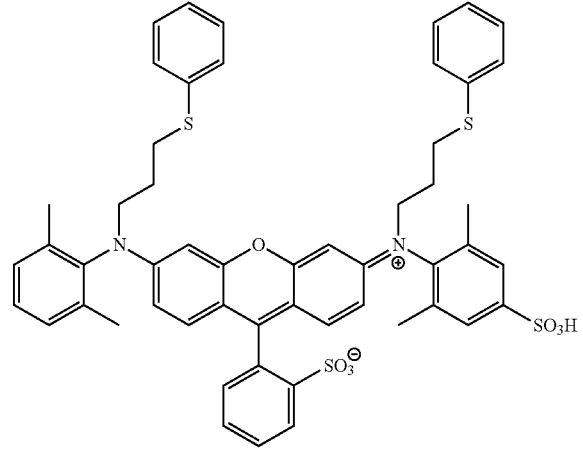
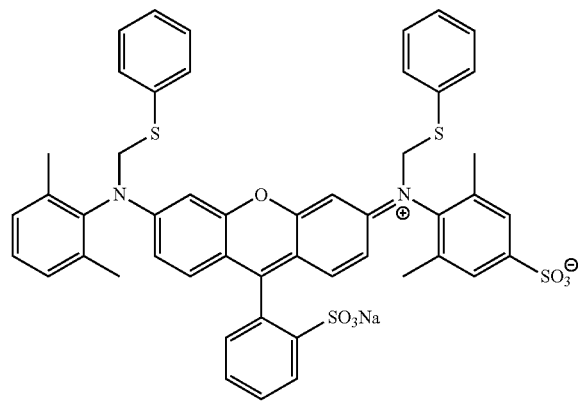

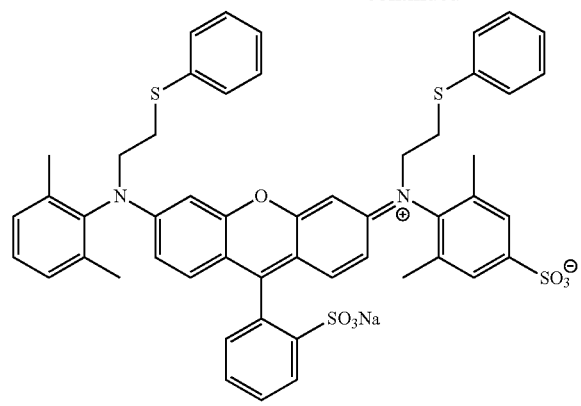
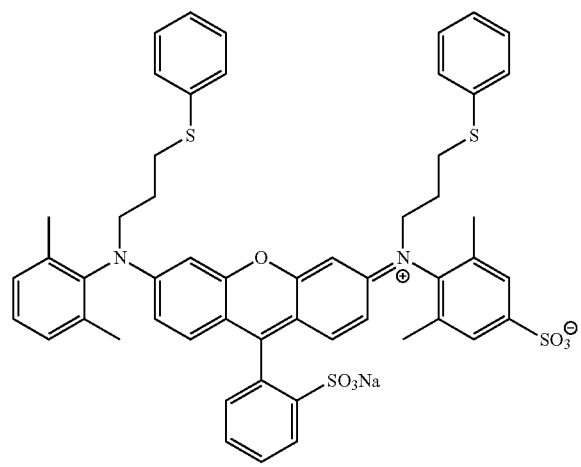
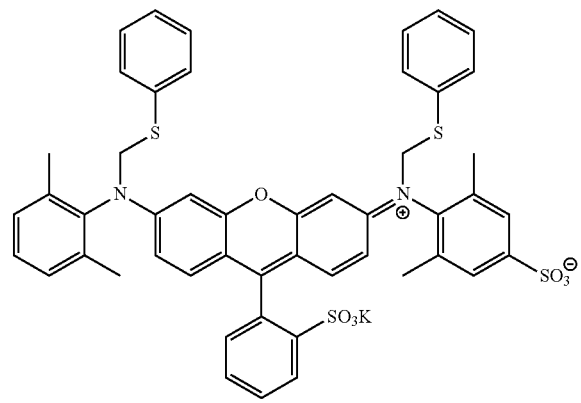
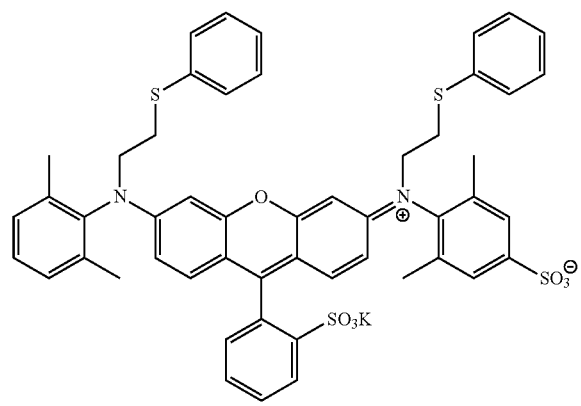

-continued
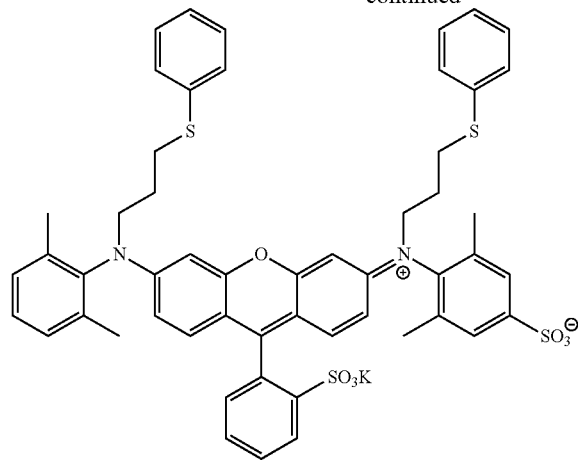
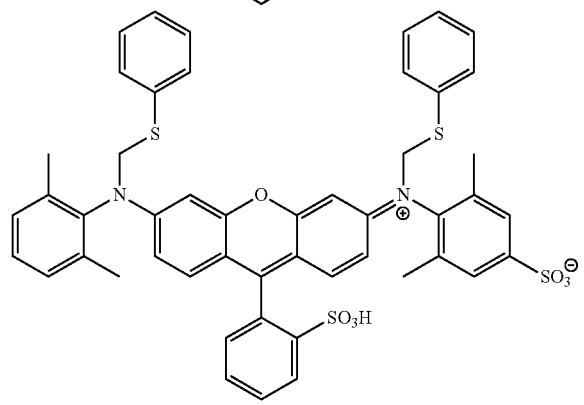
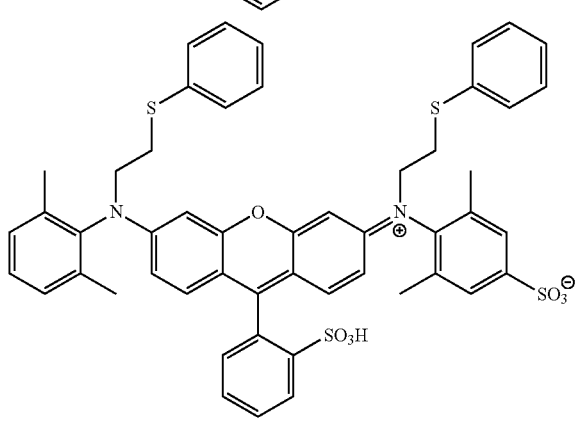
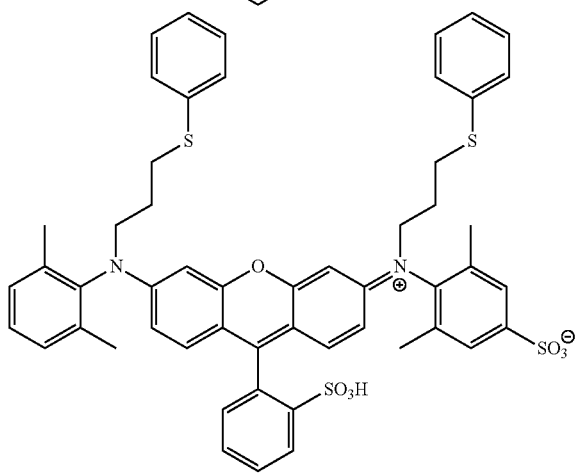

-continued
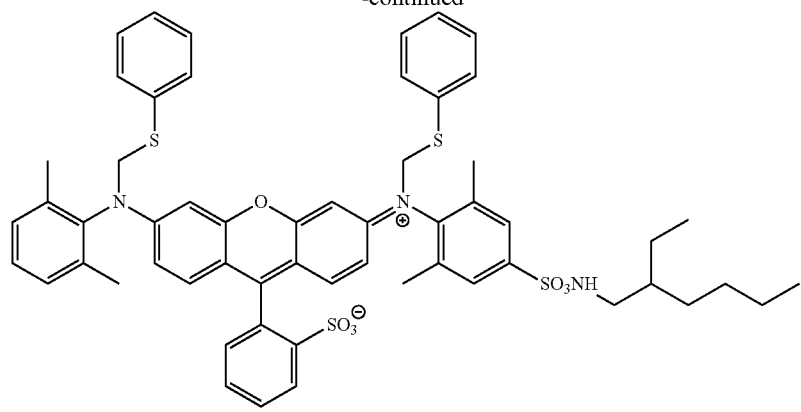
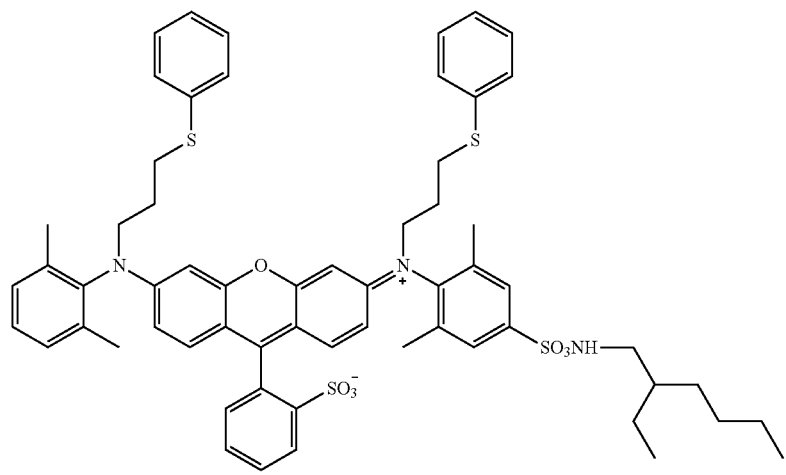
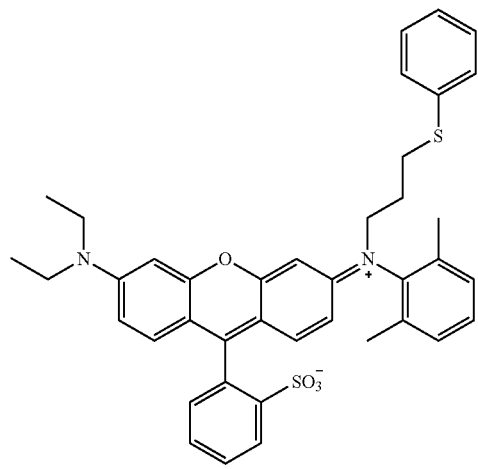

-continued
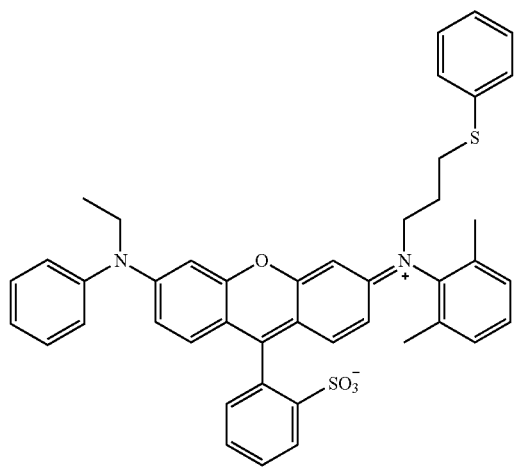
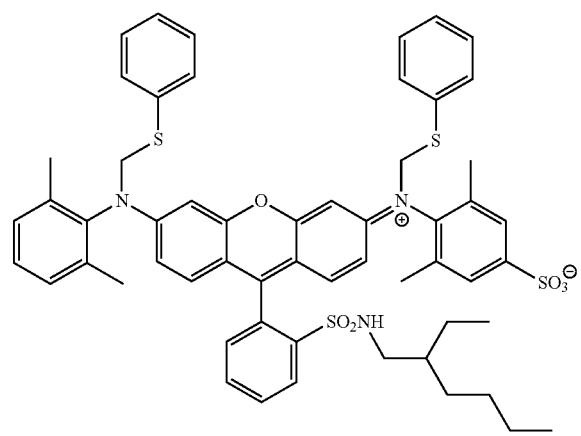
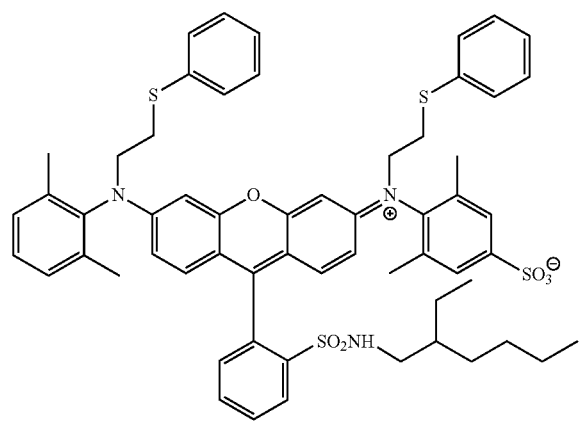

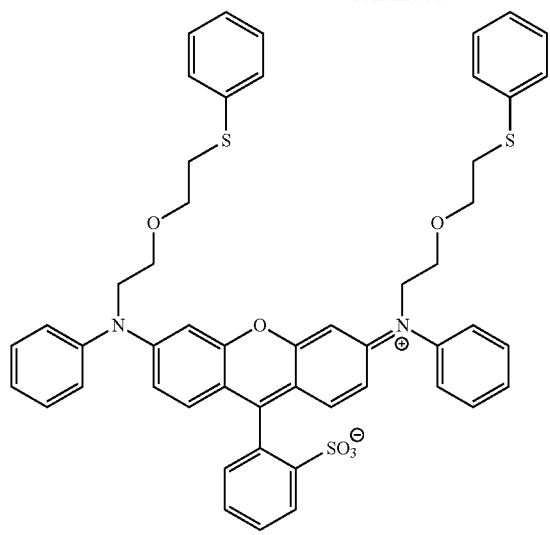
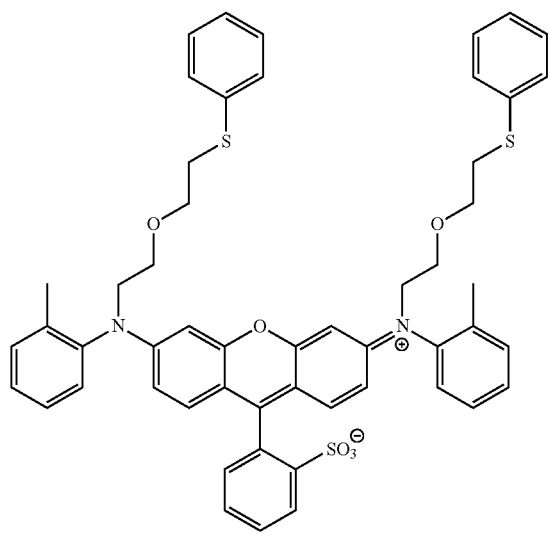
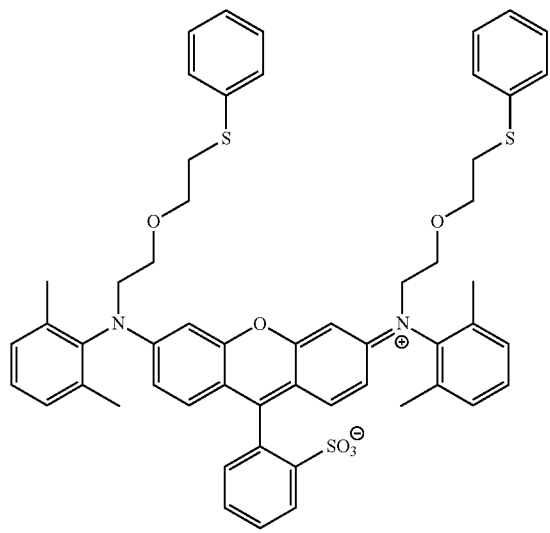

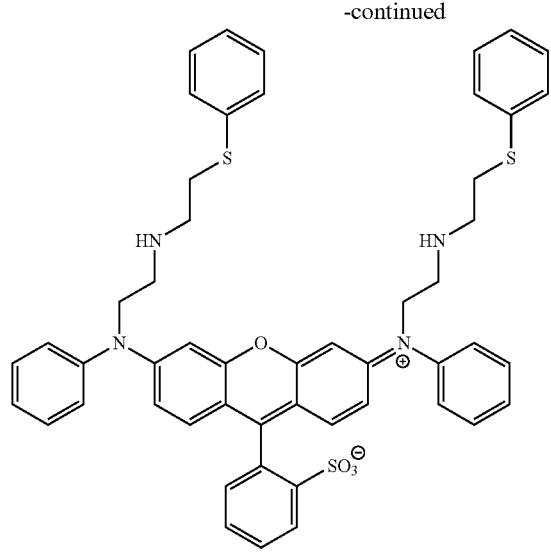
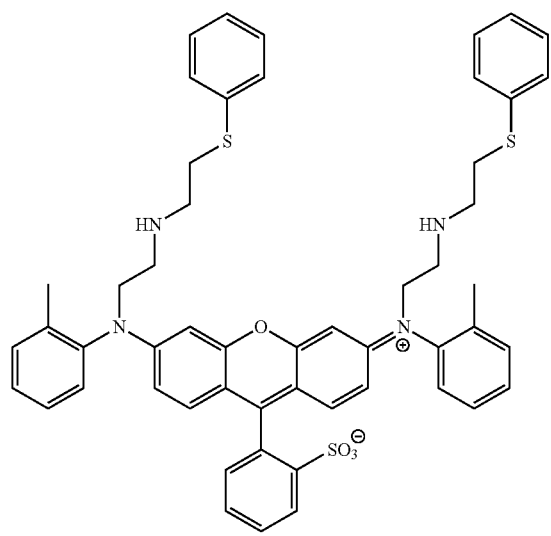
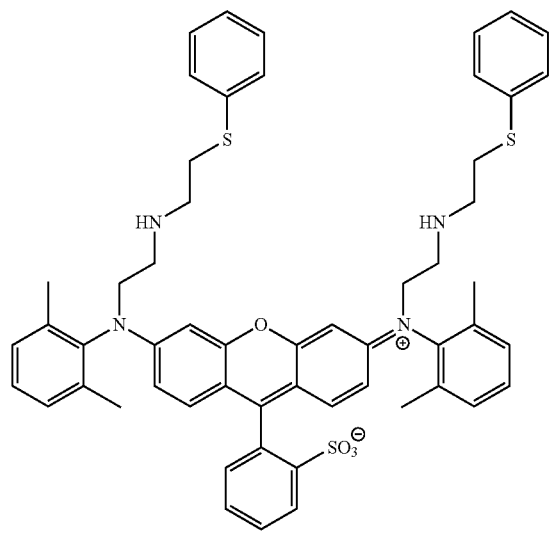

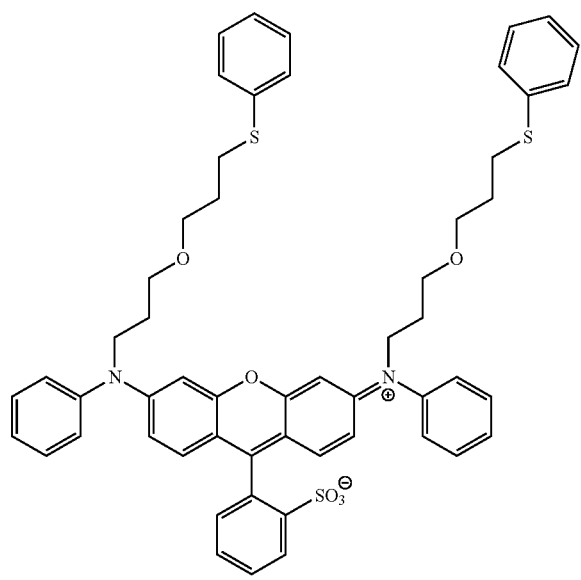
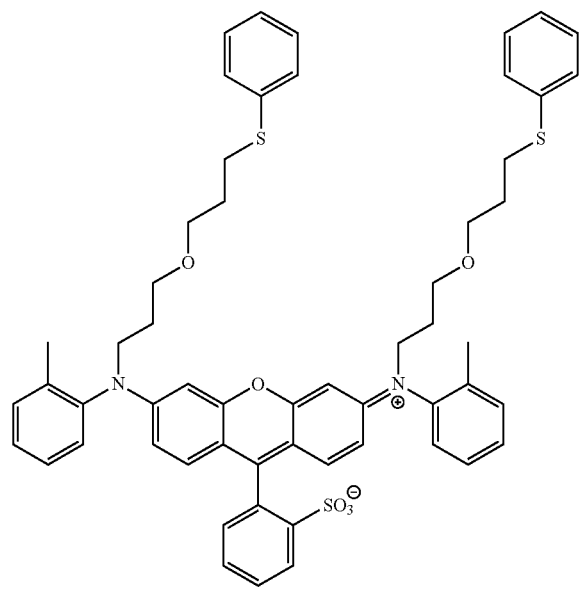

-continued
151
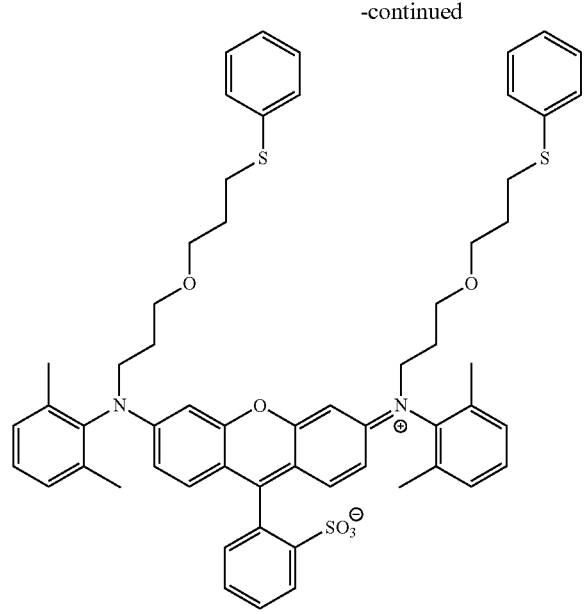
152
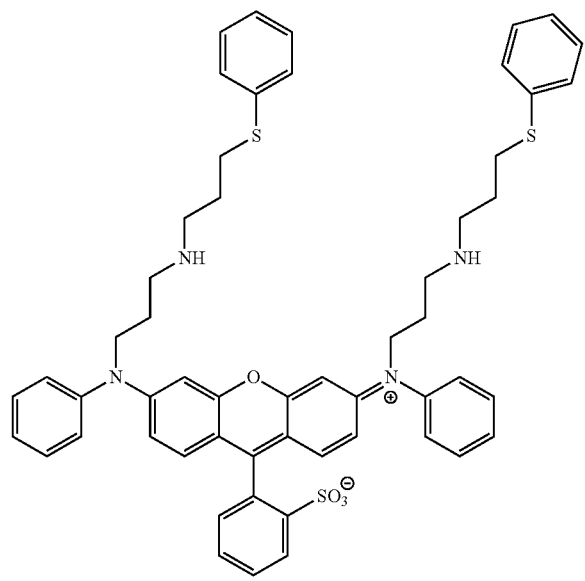

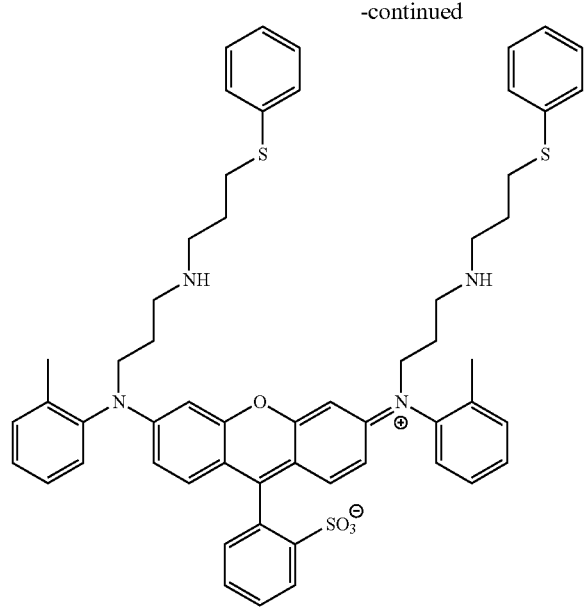
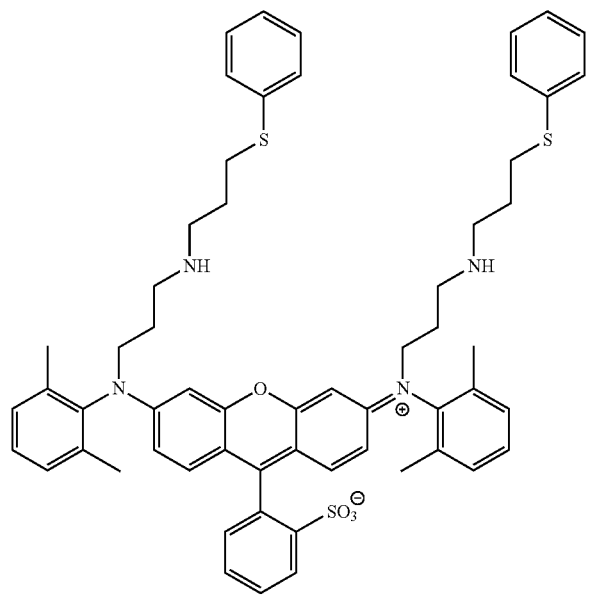
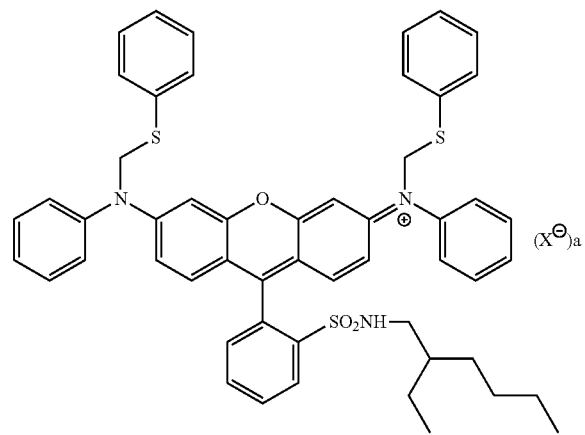

-continued
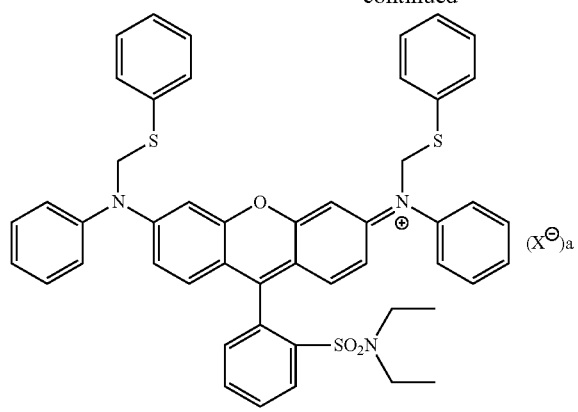
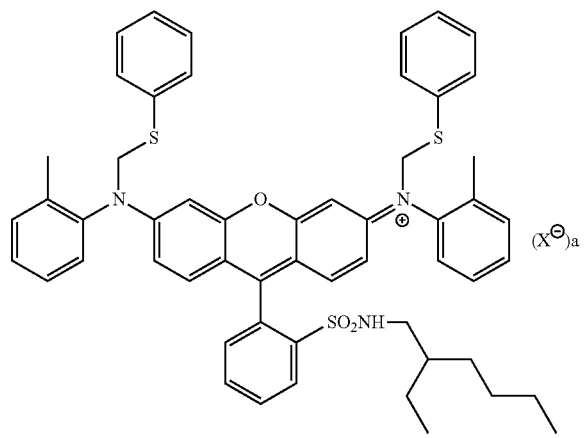
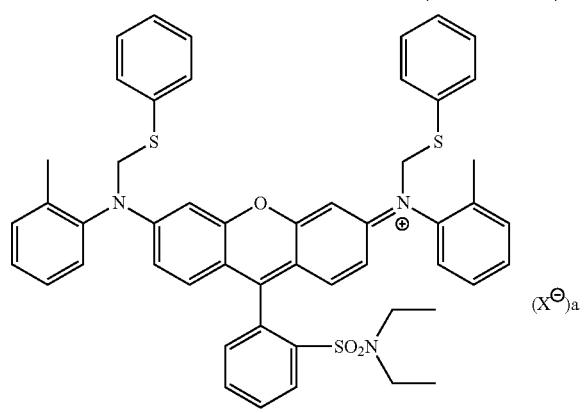
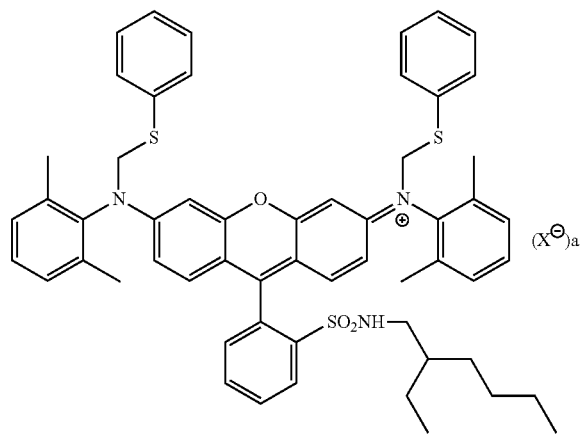

-continued
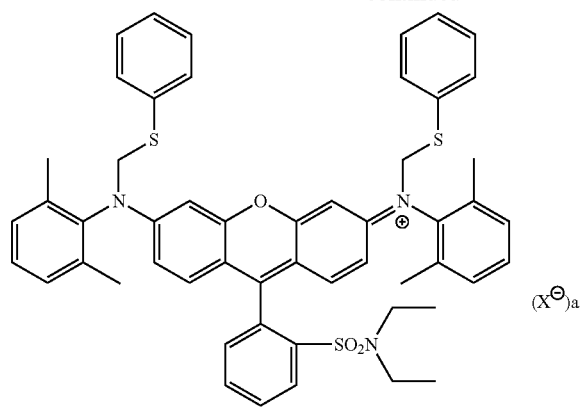
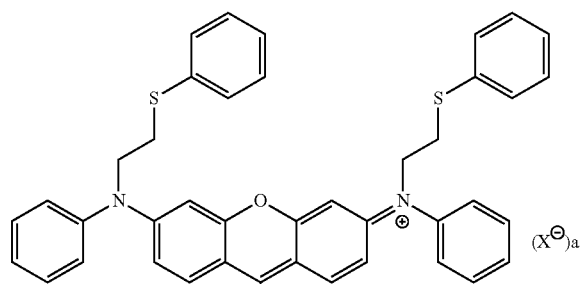
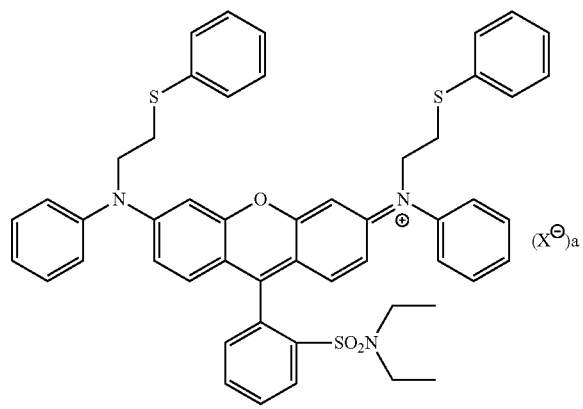
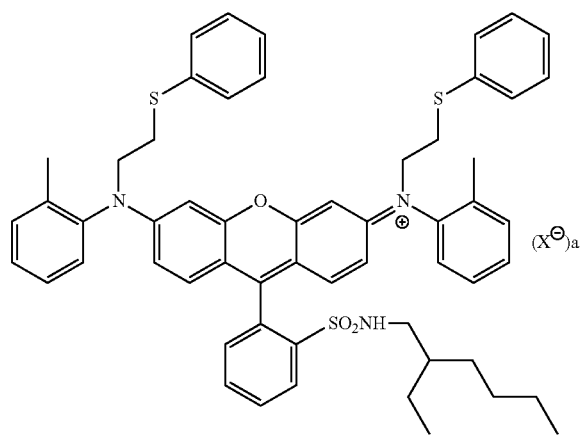

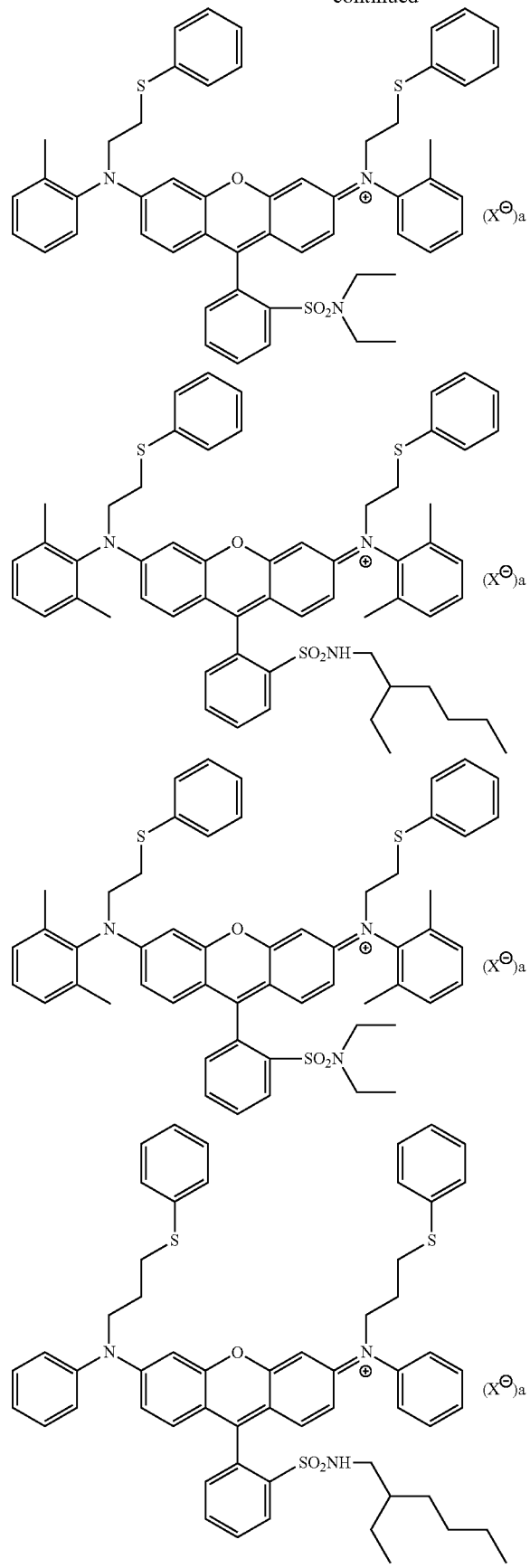

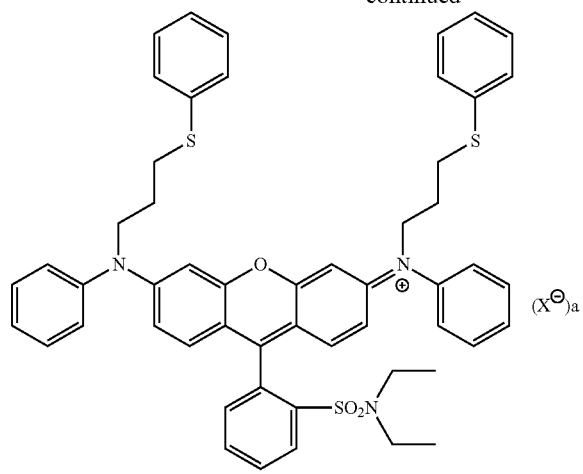
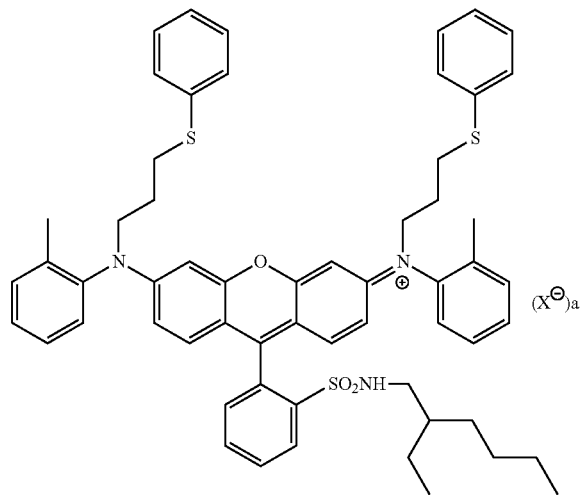
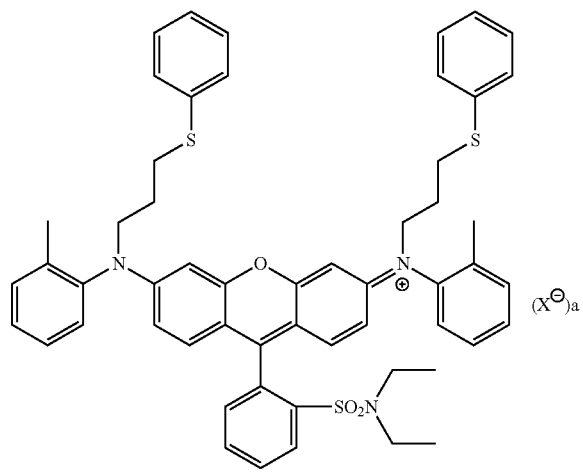

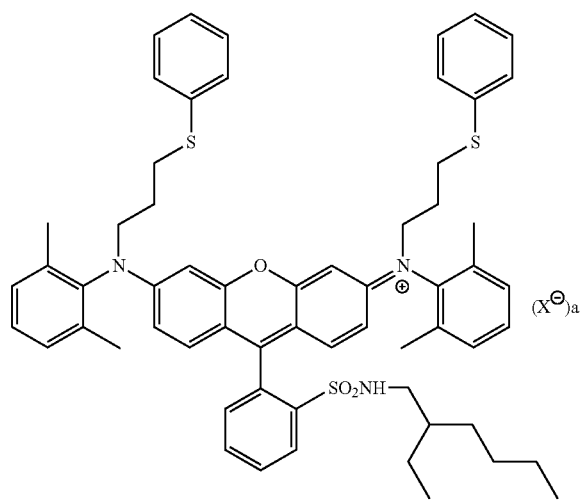
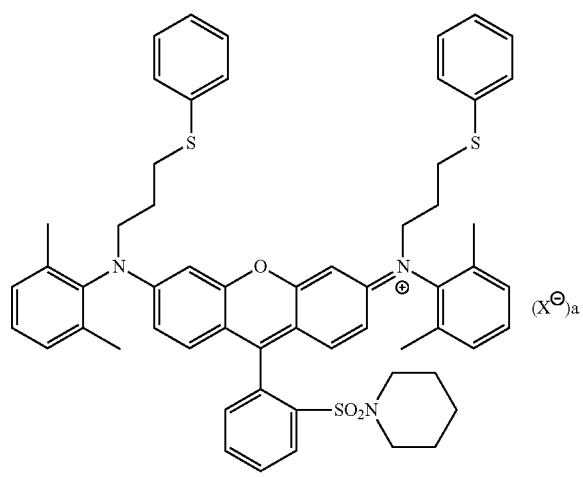
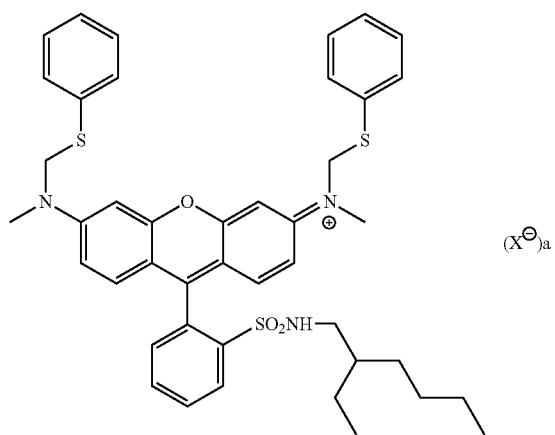

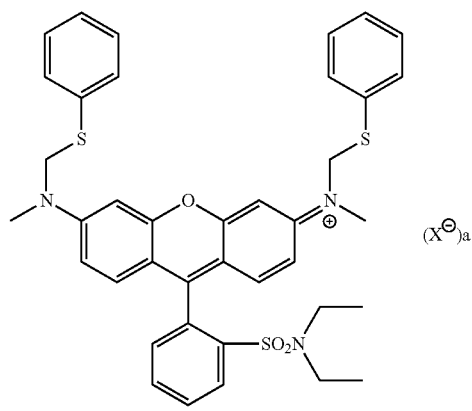
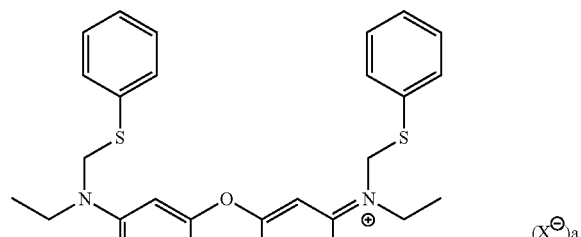
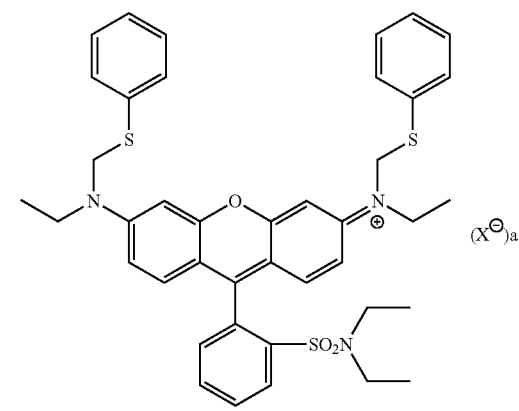
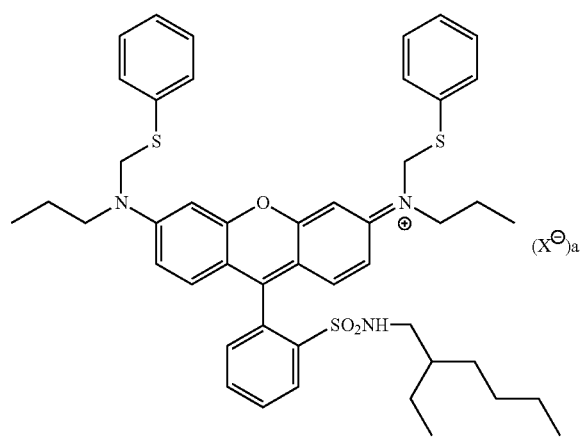

-continued
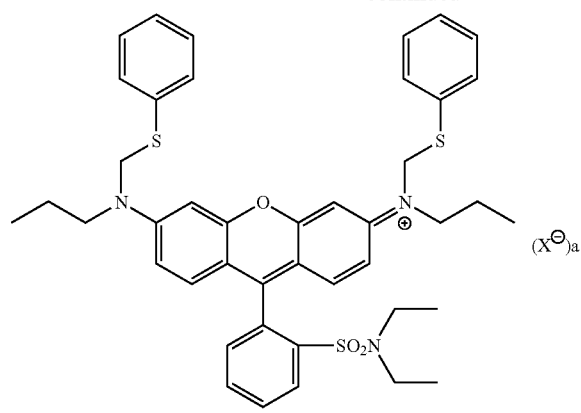
(X⊖)a
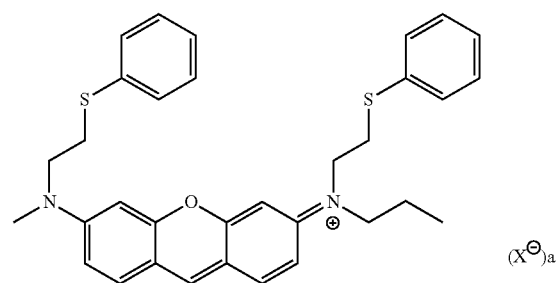
(X⊖)a
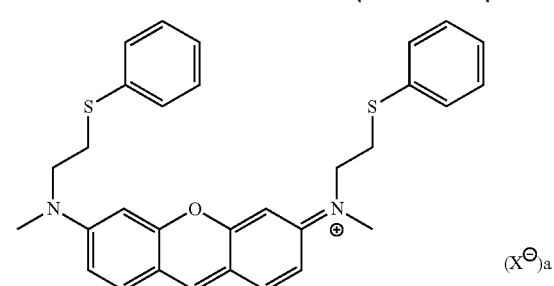
(X⊖)a
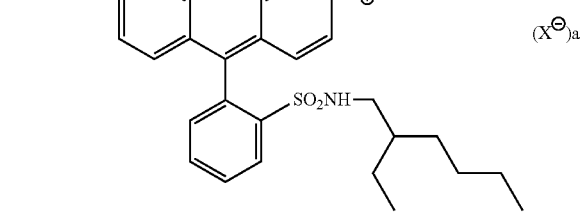
(X⊖)a -continued
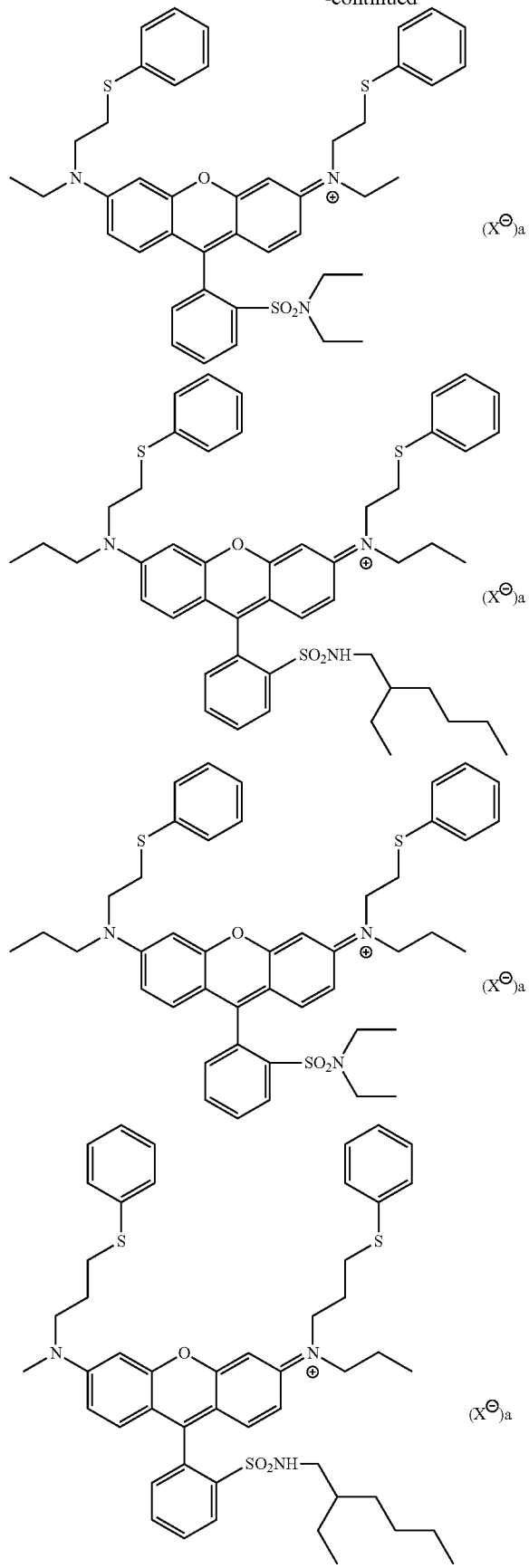

-continued
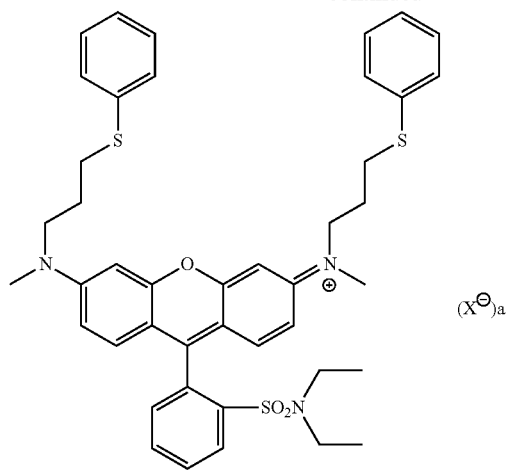
(X⊖)a
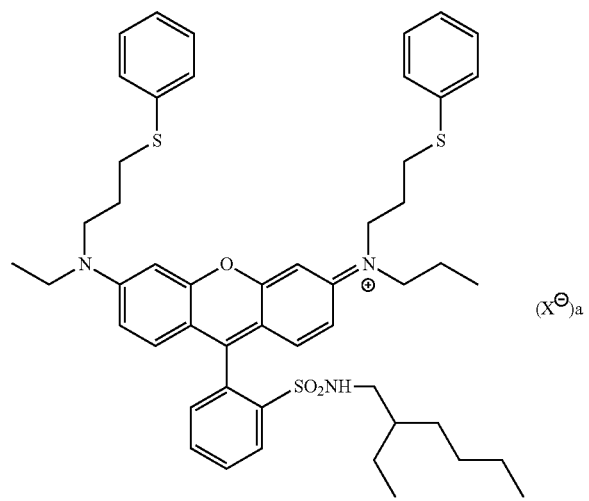
(X⊖)a
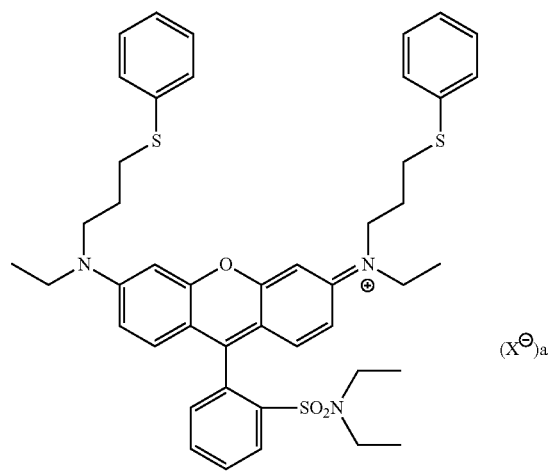
(X⊖)a

-continued
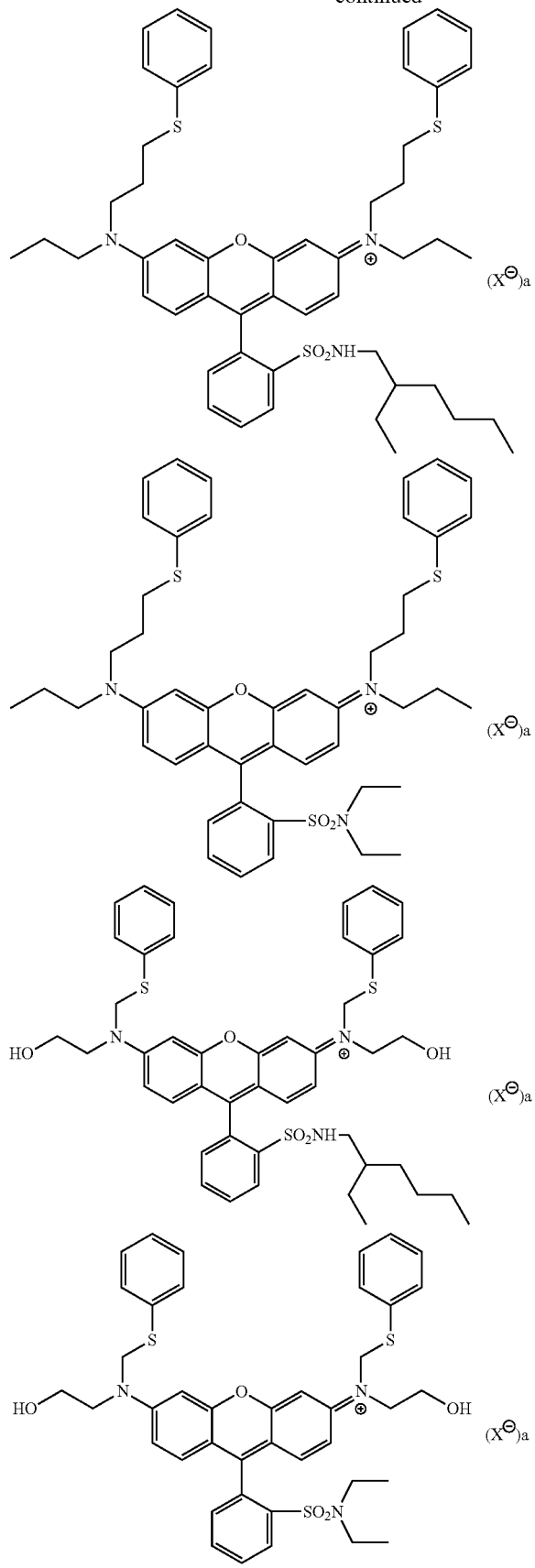

in the chemical formulae, a is an integer of 0 or 1; and

X is as defined in claim 4.

7. A colorant composition comprising the compound of claim 1.

8. The colorant composition of claim 7, further comprising at least one of a dye and a pigment.

9. The colorant composition of claim 8, wherein, the dye or the pigment are at least one compound selected from the group consisting of metal-complex-based compounds; azo-based compounds; metal azo-based compounds; quinophthalone-based compounds; isoindoline-based compounds; methine-based compounds; phthalocyanine-based compounds; metal phthalocyanine-based compounds; porphyrin-based compounds; metal porphyrin-based compounds; tetra aza porphyrin-based compounds; metal tetra aza porphyrin-based compounds; cyanine-based compounds; xanthene-based compounds; metal dipyrromethane-based compounds; boron dipyrromethane-based compounds; anthraquinone-based compounds; diketopyrrolopyrrole-based compounds; triarylmethane-based compounds; and perylene-based compounds.

10. A resin composition comprising:

the compound of claim 1;

a binder resin;

a multifunctional monomer;

a photoinitiator; and a solvent.

11. The resin composition of claim 10, wherein, based on a total weight of a solid content in the resin composition, a content of the compound represented by Chemical Formula 1 is from 5% by weight to 60% by weight, a content of the binder resin is from 1% by weight to 60% by weight, a content of the photoinitiator is from 0.1% by weight to 20% by weight, and a content of the multifunctional monomer is from 0.1% by weight to 50% by weight.

12. The resin composition of claim 10, further comprising an antioxidant.

13. A photosensitive material prepared from the resin composition of claim 10.

14. A color filter comprising the photosensitive material of claim 13.

15. A display device comprising the color filter of claim 14.

\* \* \* \* \*